(12) United States Patent
Fischer et al.

(10) Patent No.: US 8,507,537 B2
(45) Date of Patent: Aug. 13, 2013

(54) TRIFLUROMETHOXYPHENYL-SUBSTITUTED TETRAMIC ACID DERIVATIVES PESTICIDES AND/OR HERBICIDES

(75) Inventors: Reiner Fischer, Monheim (DE); Stefan Lehr, Liederbach (DE); Christian Arnold, Langenfeld (DE); Thomas Auler, Leichlingen (DE); Jan Dittgen, Frankfurt/M. (DE); Dieter Feucht, Eschborn (DE); Eva-Maria Franken, Lyon Cedex (FR); Waltraud Hempel, Liederbach (DE); Martin Jeffrey Hills, Idstein (DE); Heinz Kehne, Hofheim (DE); Peter Losel, Leverkusen (DE); Olga Malsam, Rosrath (DE); Christopher Hugh Rosinger, Hofheim (DE); Erich Sanwald, Kiel (DE); Ulrich Gorgens, Ratingen (DE); Stefan Antons, Leverkusen (DE); Wolfgang Ebenbeck, Leverkusen (DE); Axel Pleschke, Mannheim (DE); Marielouise Schneider, Leverkusen (DE); Ralf Wischnat, Bergisch Gladbach (DE)

(73) Assignee: Bayer CropScience AG, Monheim (DE)

( * ) Notice: Subject to any disclaimer, the term of this patent is extended or adjusted under 35 U.S.C. 154(b) by 718 days.

(21) Appl. No.: 12/447,037

(22) PCT Filed: Oct. 13, 2007

(86) PCT No.: PCT/EP2007/008908
§ 371 (c)(1),
(2), (4) Date: Dec. 17, 2009

(87) PCT Pub. No.: WO2008/067873
PCT Pub. Date: Jun. 12, 2008

(65) Prior Publication Data
US 2012/0015807 A1    Jan. 19, 2012

(30) Foreign Application Priority Data

Oct. 25, 2006 (DE) .......................... 10 2006 050 148

(51) Int. Cl.
| | | |
|---|---|---|
| *A01N 43/64* | (2006.01) | |
| *A61K 31/41* | (2006.01) | |
| *A01N 43/36* | (2006.01) | |
| *A01N 43/38* | (2006.01) | |
| *A01N 59/24* | (2006.01) | |
| *A01N 63/00* | (2006.01) | |
| *A61K 31/40* | (2006.01) | |
| *A61K 31/405* | (2006.01) | |
| *C07D 207/18* | (2006.01) | |
| *C07D 207/46* | (2006.01) | |
| *C07D 295/00* | (2006.01) | |
| *C07D 295/04* | (2006.01) | |
| *C07D 209/96* | (2006.01) | |
| *C07D 207/00* | (2006.01) | |
| *C07D 209/54* | (2006.01) | |

(52) U.S. Cl.
USPC ........... 514/359; 514/408; 514/409; 514/412; 514/415; 514/418; 514/425; 514/429; 548/400; 548/408; 548/541; 548/544; 548/551; 548/565; 548/570; 548/577; 504/118; 504/123; 504/124; 504/129; 504/138; 504/187; 504/188; 504/209; 504/283; 504/284

(58) Field of Classification Search
USPC ................. 504/118, 123, 124, 129, 138, 187, 504/188, 209, 283, 284; 514/359, 408, 409, 514/412, 415, 418, 425, 429; 548/400, 408, 548/541, 544, 551, 565, 570, 577
See application file for complete search history.

(56) References Cited

U.S. PATENT DOCUMENTS

| | | |
|---|---|---|
| 2,842,476 A | 7/1958 | Schreiber |
| 4,021,224 A | 5/1977 | Pallos et al. |

(Continued)

FOREIGN PATENT DOCUMENTS

| | | |
|---|---|---|
| CA | 1 162 071 A1 | 2/1984 |
| CA | 2 627 240 A1 | 5/2007 |

(Continued)

OTHER PUBLICATIONS

Uncertified English language translation of German Patent Publication DE 10 2005 059 892 A1, published Jun. 28, 2007.

(Continued)

*Primary Examiner* — Jane C Oswecki
(74) *Attorney, Agent, or Firm* — Sterne, Kessler, Goldstein & Fox P.L.L.C.

(57) ABSTRACT

The present invention relates to novel trifluoromethoxyphenyl-substituted tetramic acid derivatives of the formula (I),

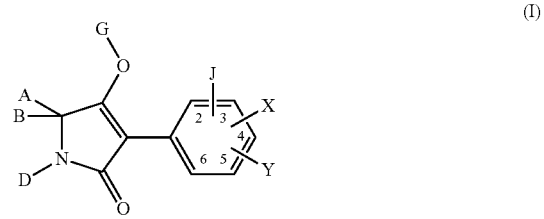

in which
J, X, Y, A, B, D and G have the meanings given above,
to a number of processes for their preparation, and to their use as pesticides and/or herbicides. The invention further provides selective herbicidal compositions which comprise, firstly, trifluoromethoxyphenyl-substituted tetramic acid derivatives and, secondly, a crop plant compatibility-improving compound.
The invention further relates to the boosting of the action of crop protection compositions comprising compounds of the formula (I) through the additions of ammonium salts or phosphonium salts and optionally penetrants.

21 Claims, No Drawings

(56) References Cited

U.S. PATENT DOCUMENTS

| | | |
|---|---|---|
| 4,186,130 A | 1/1980 | Teach |
| 4,623,727 A | 11/1986 | Hubele |
| 4,639,266 A | 1/1987 | Heubach et al. |
| 4,844,734 A | 7/1989 | Iwasaki et al. |
| 4,881,966 A | 11/1989 | Nyffeler et al. |
| 4,888,049 A | 12/1989 | Iwasaki et al. |
| 4,891,057 A | 1/1990 | Sohn et al. |
| 4,902,340 A | 2/1990 | Hubele |
| 4,925,868 A | 5/1990 | Terao et al. |
| 4,985,063 A | 1/1991 | Fischer et al. |
| 5,045,560 A | 9/1991 | Fischer et al. |
| 5,116,836 A | 5/1992 | Fischer et al. |
| 5,164,179 A | 11/1992 | Hioki et al. |
| 5,225,434 A | 7/1993 | Bertram et al. |
| 5,258,527 A | 11/1993 | Krauskopf et al. |
| 5,298,501 A | 3/1994 | Cummings |
| 5,314,863 A | 5/1994 | Loher et al. |
| 5,380,852 A | 1/1995 | Schutze et al. |
| 5,401,700 A | 3/1995 | Sohn et al. |
| 5,407,897 A | 4/1995 | Cary et al. |
| 5,462,912 A | 10/1995 | Hioki et al. |
| 5,462,913 A | 10/1995 | Fischer et al. |
| 5,504,057 A | 4/1996 | Fischer et al. |
| 5,516,750 A | 5/1996 | Willms et al. |
| 5,538,937 A * | 7/1996 | Hasebe et al. ............... 504/358 |
| 5,567,671 A | 10/1996 | Fischer et al. |
| 5,589,469 A | 12/1996 | Fischer et al. |
| 5,622,917 A | 4/1997 | Fischer et al. |
| 5,683,965 A | 11/1997 | Bachmann et al. |
| 5,700,758 A | 12/1997 | Rosch et al. |
| 5,705,476 A | 1/1998 | Hoffarth |
| 5,739,079 A | 4/1998 | Holdgrun et al. |
| 5,792,755 A | 8/1998 | Sagenmuller et al. |
| 5,811,374 A | 9/1998 | Bertram et al. |
| 5,830,826 A | 11/1998 | Fischer et al. |
| 6,075,055 A | 6/2000 | Masuda et al. |
| 6,114,374 A | 9/2000 | Lieb et al. |
| 6,133,296 A | 10/2000 | Lieb et al. |
| 6,140,358 A | 10/2000 | Lieb et al. |
| 6,200,932 B1 | 3/2001 | Fischer et al. |
| 6,235,680 B1 | 5/2001 | Ziemer et al. |
| 6,251,827 B1 | 6/2001 | Ziemer et al. |
| 6,251,830 B1 | 6/2001 | Fischer et al. |
| 6,288,102 B1 | 9/2001 | Hagemann et al. |
| 6,316,486 B1 | 11/2001 | Lieb et al. |
| 6,358,887 B1 | 3/2002 | Fischer et al. |
| 6,417,370 B1 | 7/2002 | Lieb et al. |
| 6,451,843 B1 | 9/2002 | Lieb et al. |
| 6,458,965 B1 | 10/2002 | Lieb et al. |
| 6,472,419 B1 | 10/2002 | Fischer et al. |
| 6,511,940 B1 | 1/2003 | Ziemer et al. |
| 6,511,942 B1 | 1/2003 | Lieb et al. |
| 6,589,976 B1 | 7/2003 | Fischer et al. |
| 6,602,823 B1 | 8/2003 | Rochling et al. |
| 6,608,211 B1 | 8/2003 | Hagemann et al. |
| 6,645,914 B1 | 11/2003 | Woznica et al. |
| 6,861,391 B1 | 3/2005 | Fischer et al. |
| 6,894,005 B1 * | 5/2005 | Maetzke et al. ............. 504/218 |
| 2003/0216260 A1 | 11/2003 | Ruther et al. |
| 2003/0224939 A1 | 12/2003 | Miles |
| 2005/0009880 A1 | 1/2005 | Cottrell et al. |
| 2005/0032885 A1 | 2/2005 | Fischer et al. |
| 2005/0054535 A1 | 3/2005 | Fischer et al. |
| 2005/0096386 A1 | 5/2005 | Cottrell et al. |
| 2005/0164883 A1 | 7/2005 | Maetzke et al. |
| 2006/0160847 A1 | 7/2006 | Fischer et al. |
| 2006/0166829 A1 | 7/2006 | Fischer et al. |
| 2007/0015664 A1 | 1/2007 | Fischer et al. |
| 2007/0032539 A1 | 2/2007 | Himmler |
| 2007/0129252 A1 | 6/2007 | Fischer et al. |
| 2007/0225167 A1 | 9/2007 | Fischer et al. |
| 2007/0225170 A1 | 9/2007 | Fischer et al. |
| 2007/0244007 A1 | 10/2007 | Fischer et al. |
| 2007/0275858 A1 | 11/2007 | Fischer et al. |
| 2007/0298968 A1 | 12/2007 | Bretschneider et al. |
| 2007/0298969 A1 | 12/2007 | Fischer et al. |
| 2008/0139390 A1 * | 6/2008 | Plant et al. .................... 504/103 |
| 2008/0220973 A1 | 9/2008 | Fischer et al. |
| 2008/0305955 A1 | 12/2008 | Bretschneider et al. |
| 2008/0318776 A1 | 12/2008 | Fischer et al. |
| 2009/0029858 A1 | 1/2009 | Fischer et al. |
| 2009/0099192 A1 | 4/2009 | Bretschneider et al. |
| 2009/0215624 A1 | 8/2009 | Fischer et al. |
| 2009/0298828 A1 | 12/2009 | Fischer et al. |

FOREIGN PATENT DOCUMENTS

| | | |
|---|---|---|
| CA | 2 632 892 A1 | 6/2007 |
| CA | 2 633 448 A1 | 6/2007 |
| CA | 2 633 525 A1 | 7/2007 |
| CA | 2 642 787 A1 | 8/2007 |
| CA | 2 649 552 A1 | 11/2007 |
| DE | 22 18 097 A1 | 11/1972 |
| DE | 23 50 547 A1 | 4/1974 |
| DE | 1 962 1522 A1 | 12/1997 |
| DE | 10 2005 059 892 A1 | 6/2007 |
| DE | 10 2006 007882 A1 | 8/2007 |
| DE | 10 2006 018 828 A1 | 10/2007 |
| DE | 10 2006 025 874 A1 | 12/2007 |
| EP | 0 036 106 A2 | 9/1981 |
| EP | 0 086 750 A2 | 8/1983 |
| EP | 0 094 349 A2 | 11/1983 |
| EP | 0 174 562 A2 | 3/1986 |
| EP | 0 191 736 A2 | 8/1986 |
| EP | 0 262 399 A2 | 4/1988 |
| EP | 0 269 806 A1 | 6/1988 |
| EP | 0 333 131 A1 | 9/1989 |
| EP | 0 346 620 A1 | 12/1989 |
| EP | 0 355 599 A1 | 2/1990 |
| EP | 0 377 893 A2 | 7/1990 |
| EP | 0 415 211 A2 | 3/1991 |
| EP | 0 442 073 B1 | 8/1991 |
| EP | 0 442 077 A2 | 8/1991 |
| EP | 0 453 086 A2 | 10/1991 |
| EP | 0 456 063 A2 | 11/1991 |
| EP | 0 492 366 A2 | 7/1992 |
| EP | 0 521 334 A1 | 1/1993 |
| EP | 0 582 198 A2 | 2/1994 |
| EP | 0 596 298 A2 | 5/1994 |
| EP | 0 613 618 A1 | 9/1994 |
| EP | 0 613 884 A2 | 9/1994 |
| EP | 0 613 885 A2 | 9/1994 |
| EP | 0 664 081 A2 | 7/1995 |
| EP | 0 668 267 A1 | 8/1995 |
| EP | 0 681 865 A2 | 11/1995 |
| EP | 0 809 629 A1 | 12/1997 |
| EP | 0 854 134 A1 | 7/1998 |
| EP | 0 915 846 B1 | 5/1999 |
| EP | 1 925 617 A1 | 5/2008 |
| FR | 2 600 494 A1 | 12/1987 |
| GB | 2 266 888 A | 11/1993 |
| JP | 2000 053670 A2 | 2/2000 |
| WO | WO 91/07874 A1 | 6/1991 |
| WO | WO 91/08202 A1 | 6/1991 |
| WO | WO 92/16108 A1 | 10/1992 |
| WO | WO 92/16510 A1 | 10/1992 |
| WO | WO 95/01971 A1 | 1/1995 |
| WO | WO 95/07897 A1 | 3/1995 |
| WO | WO 95/17817 A1 | 7/1995 |
| WO | WO 95/20572 A1 | 8/1995 |
| WO | WO 95/26954 A1 | 10/1995 |
| WO | WO 96/25395 A1 | 8/1996 |
| WO | WO 96/35664 A1 | 11/1996 |
| WO | WO 97/01535 A1 | 1/1997 |
| WO | WO 97/02243 A1 | 1/1997 |
| WO | WO 97/36868 A1 | 10/1997 |
| WO | WO 97/43275 A2 | 11/1997 |
| WO | WO 98/05638 A2 | 2/1998 |
| WO | WO 98/06721 A1 | 2/1998 |
| WO | WO98/35553 * | 2/1998 |
| WO | WO 98/25928 A1 | 6/1998 |
| WO | WO 98/35553 A1 | 8/1998 |
| WO | WO 99/16748 A1 | 4/1999 |
| WO | WO 99/24437 A1 | 5/1999 |
| WO | WO 99/43649 A1 | 9/1999 |

| WO | WO 99/48869 A1 | 9/1999 |
| --- | --- | --- |
| WO | WO 99/55673 A1 | 11/1999 |
| WO | WO 99/66795 A1 | 12/1999 |
| WO | WO 00/35278 A1 | 6/2000 |
| WO | WO 01/17972 A2 | 3/2001 |
| WO | WO 01/23354 A2 | 4/2001 |
| WO | WO 01/74770 A1 | 10/2001 |
| WO | WO 03/013249 A1 | 2/2003 |
| WO | WO 2004/007448 A1 | 1/2004 |
| WO | WO 2004/024688 A1 | 3/2004 |
| WO | WO 2004/065366 A1 | 8/2004 |
| WO | WO 2004/080962 A1 | 9/2004 |
| WO | WO 2004/111042 A1 | 12/2004 |
| WO | WO 2005/044791 A2 | 5/2005 |
| WO | WO 2005/044796 A1 | 5/2005 |
| WO | WO 2005/048710 A1 | 6/2005 |
| WO | WO 2005/049569 A1 | 6/2005 |
| WO | WO 2005/066125 A1 | 7/2005 |
| WO | WO 2005/092897 A2 | 10/2005 |
| WO | WO 2006/000355 A1 | 1/2006 |
| WO | WO 2006/007998 A1 | 1/2006 |
| WO | WO 2006/029799 A1 | 3/2006 |
| WO | WO 2006/056281 A1 | 6/2006 |
| WO | WO 2006/056282 A1 | 6/2006 |
| WO | WO 2006/089633 A2 | 8/2006 |
| WO | WO 2007/048545 A2 | 5/2007 |
| WO | WO 2007/059838 A1 | 5/2007 |
| WO | WO 2007/ 068427 A2 | 6/2007 |
| WO | WO 2007/ 068428 A2 | 6/2007 |
| WO | WO 2007/073856 A2 | 7/2007 |
| WO | WO 2008/009908 A1 | 1/2008 |

OTHER PUBLICATIONS

Baur, P., et al., "Polydisperse Ethoxylated Fatty Alcohol Surfactants as Accelerators of Cuticular Penetration. 1. Effects of Ethoxy Chain Length and the Size of the Penetrants," *Pestic. Sci.* 51:131-152, SCI (1997).

Bhattacharya, B., "Isoquinoline Derivatives: Part XVIII—Formation of I-Alkyl-(or alkaryl or aryl)-3-methyl-7-chloro-(or 5-chloro)-isoquinolines," *Indian J. Chem.* 6:341-345, Council of Scientific and Industrial Research (1968).

Compagnon, P.L., and Miocque, M., "Addition des Réactifs Nucléophiles sur la Triple Liaison Nitrile," *Ann. Chim.* 5:11-22, Masson (1970).

Edward, J.T., and Jitrangsri, C., "Stereochemistry of the Bucherer-Bergs and Strecker Reactions of 4-*tert*-Butylcyclohexanone," *Can J. Chem.* 53:3339-3350, NRC Research Press (1975).

Harrison, H.R., et al., "Use of molecular sieves in the methyl esterification of carboxylic acids," *Chem. Ind.*, p. 1568, Society of Chemical Industry (1968).

Munday, L., "Amino-acids of the Cyclohexane Series. Part I.," *J. Chem. Soc.*, pp. 4372-4379, Royal Society of Chemistry (1961).

Schmierer, R. and Mildenberger, H., "Cyclization of N-acylalanine and N-acylglycine Esters," *Liebigs Ann. Chem.* 1985:1095-1098, VCH Verlagsgesellschaft mbH (1985).

Sonntag, N.O.V., "The Reactions of Aliphatic Acid Chlorides," *Chem. Rev.* 52:237-416, American Chemical Society (1953).

Suzuki, S., et al., "Studies on Antiviral Agents. IV. Biological Activity of Tenuazonic Acid Derivatives," *Chem. Pharm. Bull.* 15:1120-1122, Pharmaceutical Society of Japan (1967).

International Search Report for International Application No. PCT/EP2007/008908, European Patent Office, Netherlands, mailed on Feb. 25, 2008.

Patent Abstract of Japan, English language abstract of Japanese Patent 2000-053670 (listed on accompanying PTO/SB/08A as document FP12), (2000).

Dialog File 351, Accession No. 4963457, Derwent WPI English language abstract for EP 0 346 620 A1 (listed on accompanying PTO/SB/08A as document FP14), (1989).

Dialog File 351, Accession No. 17343120, Derwent WPI English language abstract for DE 10 2005 059 892 A1 (listed on accompanying PTO/SB/08A as document FP88), (2007).

Henecka and Houben-Weyl, *Methoden der Organishchen Chemie*, 8:467-469 (1952).

CAS Registry No. 886503-16-8, [2,6-dichloro-4-(trifluoromethoxy)phenyl]acetic acid, accessed at www.chemnet.com/cas/en/886503-16-8/[2,6-dichloro-4-(trifluoromethoxy)phenyl]acetic-acid.html, accessed on Feb. 25, 2013.

* cited by examiner

TRIFLUROMETHOXYPHENYL-SUBSTITUTED TETRAMIC ACID DERIVATIVES PESTICIDES AND/OR HERBICIDES

The present invention relates to novel trifluoromethoxyphenyl-substituted tetramic acid derivatives, to a plurality of processes for their preparation and to their use as pesticides and/or herbicides. The invention also provides selective herbicidal compositions comprising, firstly, the trifluoromethoxyphenyl-substituted tetramic acid derivatives and, secondly, a crop plant compatibility-improving compound.

The present invention further relates to the boosting of the action of crop protection compositions comprising, in particular, trifluoromethoxyphenyl-substituted tetramic acid derivatives, through the addition of ammonium salts or phosphonium salts and optionally penetrants, to the corresponding compositions, to processes for producing them and to their application in crop protection as insecticides and/or acaricides and/or for preventing unwanted plant growth.

For 3-acylpyrrolidine-2,4-diones pharmaceutical properties have been previously described (S. Suzuki et al. Chem. Pharm. Bull. 15 1120 (1967)). Furthermore, N-phenylpyrrolidine-2,4-diones have been synthesized by R. Schmierer and H. Mildenberger (Liebigs Ann. Chem. 1985, 1095). Biological activity of these compounds has not been described.

EP-A-0 262 399 and GB-A-2 266 888 disclose similarly structured compounds (3-arylpyrrolidine-2,4-diones) for which, however, no herbicidal, insecticidal or acaricidal action has been disclosed. Known compounds with herbicidal, insecticidal or acaricidal action are unsubstituted, bicyclic 3-arylpyrrolidine-2,4-dione derivatives (EP-A-355 599, EP-A-415 211 and JP-A-12-053 670) and also substituted monocyclic 3-arylpyrrolidine-2,4-dione derivatives (EP-A-377 893 and EP-A-442 077).

Additionally known are polycyclic 3-arylpyrrolidine-2,4-dione derivatives (EP-A-442 073) and also 1H-arylpyrrolidinedione derivatives (EP-A-456 063, EP-A-521 334, EP-A-596 298, EP-A-613 884, EP-A-613 885, WO 94/01997, WO 95/26954, WO 95/20572, EP-A-0 668 267, WO 96/25395, WO 96/35664, WO 97/01535, WO 97/02243, WO 97/36868, WO 97/43275, WO 98/05638, WO 98/06721, WO 98/25928, WO 99/16748, WO 99/24437, WO 99/43649, WO 99/48869, WO 99/55673, WO 01/17972, WO 01/23354, WO 01/74770, WO 03/013249, WO 04/007448, WO 04/024688, WO 04/065366, WO 04/080962, WO 04/111042, WO 05/044791, WO 05/044796, WO 05/048710, WO 05/049596, WO 05/066125, WO 05/092897, WO 06/000355, WO 06/029799, WO 06/056281, WO 06/056282, WO 06/089633, WO 07/048,545, WO 07/073,856, DE-A-05/059892, DE-A-06/007882, DE-A-06/018828, DE-A-06/025874).

However, in particular at low application rates and concentrations, the activity and activity spectrum of these compounds is not always fully satisfactory. Furthermore, the compatibility of these compounds with some crop plants is not always sufficient.

This invention now provides novel compounds of the formula (I)

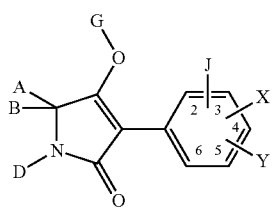

(I)

in which
J represents trifluoromethoxy,
X represents hydrogen, alkyl, halogen, haloalkyl, alkoxy or haloalkoxy,
Y represents hydrogen, alkyl, alkoxy or halogen,
with the proviso, that at least one of the radicals J, X and Y is located in the 2-position of the phenyl radical and is not hydrogen,
A represents hydrogen, in each case optionally halogen-substituted alkyl, alkenyl, alkoxyalkyl, alkylthioalkyl, saturated or unsaturated, optionally substituted cycloalkyl in which optionally at least one ring atom is replaced by a heteroatom, or in each case optionally halogen-, alkyl-, haloalkyl-, alkoxy-, haloalkoxy-, cyano- or nitro-substituted aryl, arylalkyl or hetaryl,
B represents hydrogen, alkyl or alkoxyalkyl, or
A and B together with the carbon atom to which they are attached represent a saturated or unsaturated, unsubstituted or substituted cycle which optionally contains at least one heteroatom,
D represents hydrogen or an optionally substituted radical from the group consisting of alkyl, alkenyl, alkynyl, alkoxyalkyl, saturated or unsaturated cycloalkyl in which optionally one or more ring members are replaced by heteroatoms, arylalkyl, aryl, hetarylalkyl or hetaryl or
A and D together with the atoms to which they are attached represent a saturated or unsaturated cycle which optionally contains at least one heteroatom and which is unsubstituted or substituted in the A, D moiety,
G represents hydrogen (a) or represents one of the groups

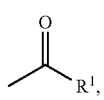
(b)

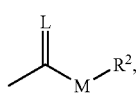
(c)

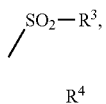
(d)

(e)

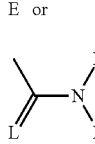
(f)

E or
(g)

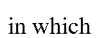

in which
E represents a metal ion equivalent or an ammonium ion,
L represents oxygen or sulphur,
M represents oxygen or sulphur,
$R^1$ represents in each case optionally halogen-substituted alkyl, alkenyl, alkoxyalkyl, alkylthioalkyl, polyalkoxyalkyl or optionally halogen-, alkyl- or alkoxy-substituted cycloalkyl which may be interrupted by at least one heteroatom, in each case optionally substituted phenyl, phenylalkyl, hetaryl, phenoxyalkyl or hetaryloxyalkyl, $R^2$ represents in each case optionally halogen-substituted alkyl, alkenyl, alkoxyalkyl, polyalkoxyalkyl or represents in each case optionally substituted cycloalkyl, phenyl or benzyl, $R^3$, $R^4$ and $R^5$ independently of one another represent in each case optionally halogen-substituted alkyl, alkoxy, alkylamino, dialkylamino, alkylthio, alkenylthio, cycloalkylthio or represent in each case optionally substituted phenyl, benzyl, phenoxy or phenylthio, $R^6$ and $R^7$ independently of one another represent hydrogen, in each case optionally halogen-substituted alkyl, cycloalkyl, alkenyl, alkoxy, alkoxyalkyl, represent optionally substituted phenyl, represent optionally substituted benzyl, or together with the nitrogen atom to which they are attached represent a cycle which is optionally interrupted by oxygen or sulphur.

Depending inter alia on the nature of the substituents, the compounds of the formula (I) may be present as geometrical and/or optical isomers or isomer mixtures of varying composition which, if appropriate, may be separated in a customary manner. The present invention provides for the pure isomers and the isomer mixtures, their preparation and use and compositions comprising them. However, for the sake of simplicity, hereinbelow only compounds of the formula (I) are referred to, although what is meant are both the pure compounds and, if appropriate, mixtures having various proportions of isomeric compounds.

Including the different meanings (a), (b), (c), (d), (e), (f) and (g) of group G, the following principal structures (I-a) to (I-g) result (I-a):

(I-b):

(I-c):

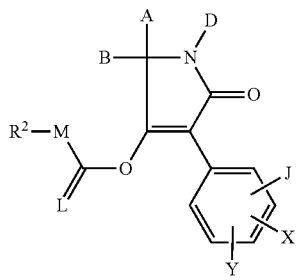

(I-d):

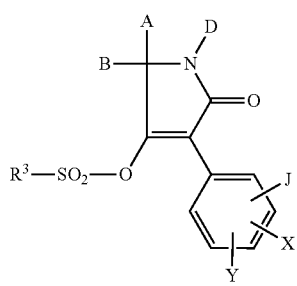

(I-e):

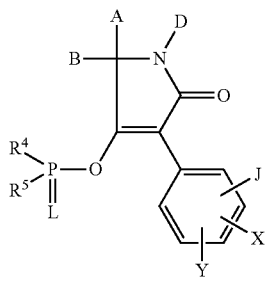

(I-f):

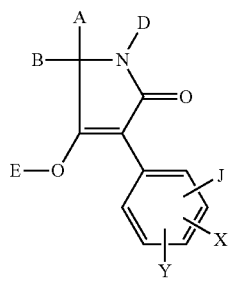

(I-g):

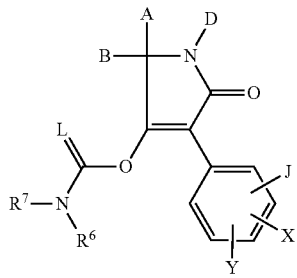

in which
A, B, D, E, J, L, M, X, Y, $R^1$, $R^2$, $R^3$, $R^4$, $R^5$, $R^6$ and $R^7$ have the meanings given above.

Furthermore, it has been found that the novel compounds of the formula (I) are obtained by one of the processes described below:

(A) Compounds of the formula (I-a)

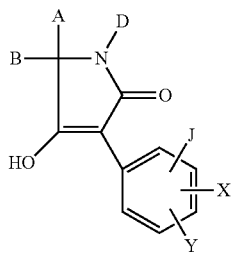

(I-a)

in which
A, B, D, J, X and Y have the meanings given above,
are obtained when
N-acylamino acid esters of the formula (II)

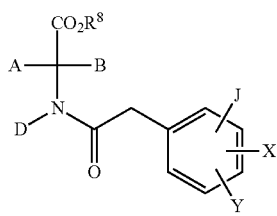

(II)

in which
A, B, D, J, X and Y have the meanings given above,
and
$R^8$ represents alkyl (preferably $C_1$-$C_6$-alkyl),
are condensed intramolecularly in the presence of a diluent and in the presence of a base.

Furthermore, it has been found
(B) that the compounds of the formula (I-b) shown above in which A, B, D, J, $R^1$, X, and Y have the meanings given above are obtained when compounds of the formula (I-a) shown above in which A, B, D, J, X and Y have the meanings given above are in each case reacted
(α) with acid halides of the formula (III)

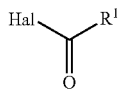

(III)

in which
$R^1$ has the meaning given above and
Hal represents halogen (in particular chlorine or bromine)
or
(β) with carboxylic anhydrides of the formula (IV)

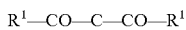 (IV)

in which
$R^1$ has the meaning given above,
optionally in the presence of a diluent and if appropriate in the presence of an acid binder;
(C) that the compounds of the formula (I-c) shown above in which A, B, D, J, $R^2$, M, X and Y have the meanings given above and L represents oxygen are obtained when compounds of the formula (I-a) shown above in which A, B, D, J, X and Y have the meanings given above are in each case reacted
with chloroformic esters or chloroformic thioesters of the formula (V)

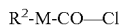 (V)

in which
$R^2$ and M have the meanings given above,
optionally in the presence of a diluent and optionally in the presence of an acid binder;
(D) that compounds of the formula (I-c) shown above in which A, B, D, J, $R^2$, M, X and Y have the meanings given above and L represents sulphur are obtained when compounds of the formula (I-a) shown above in which A, B, D, J, X and Y have the meanings given above are in each case reacted
with chlormonothioformic esters or chlordithioformic esters of the formula (VI)

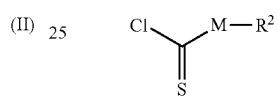

(VI)

in which
M and $R^2$ have the meanings given above,
if appropriate in the presence of a diluent and if appropriate in the presence of an acid binder
and
(E) that compounds of the formula (I-d) shown above in which A, B, D, J, $R^3$, X and Y have the meanings given above are obtained when compounds of the formula (I-a) shown above in which A, B, D, J, X and Y have the meanings given above are in each case reacted
with sulphonyl chlorides of the formula (VII)

 (VII)

in which
$R^3$ has the meaning given above,
if appropriate in the presence of a diluent and if appropriate in the presence of an acid binder,
(F) that compounds of the formula (I-e) shown above in which A, B, D, J, L, $R^4$, $R^5$, X and Y have the meanings given above are obtained when compounds of the formula (I-a) shown above in which A, B, D, J, X and Y have the meanings given above are in each case reacted
with phosphorus compounds of the formula (VIII)

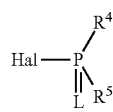

(VIII)

in which
L, $R^4$ and $R^5$ have the meanings given above and
Hal represents halogen (in particular chlorine or bromine),
if appropriate in the presence of a diluent and if appropriate in the presence of an acid binder,
(G) that compounds of the formula (I-f) shown above in which A, B, D, E, J, X and Y have the meanings given above are obtained when compounds of the formula (I-a) in which A, B, D, J, X and Y have the meanings given above are in each case reacted with metal compounds or amines of the formulae (IX) and (X), respectively,

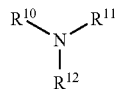
(IX)

(X)

in which

Me represents a mono- or divalent metal (preferably an alkali metal or alkaline earth metal, such as lithium, sodium, potassium, magnesium or calcium), or represents an ammonium ion

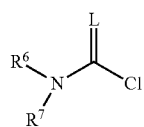

t represents the number 1 or 2 and $R^{10}$, $R^{11}$, $R^{12}$ independently of one another represent hydrogen or alkyl (preferably $C_1$-$C_8$-alkyl), if appropriate in the presence of a diluent, (H) that compounds of the formula (I-g) shown above in which A, B, D, J, L, $R^6$, $R^7$, X and Y have the meanings given above are obtained when compounds of the formula (I-a) shown above in which A, B, D, J, X and Y have the meanings given above are in each case reacted (α) with isocyanates or isothiocyanates of the formula (XI)

$R^6$—N=C=L         (XI)

in which $R^6$ and L have the meanings given above, if appropriate in the presence of a diluent and if appropriate in the presence of a catalyst, or (β) with carbamoyl chlorides or thiocarbamoyl chlorides of the formula (XII)

(XII)

in which

L, $R^6$ and $R^7$ have the meanings given above, if appropriate in the presence of a diluent and if appropriate in the presence of an acid binder.

The following compounds of the formula (I) have been disclosed in the context of the European patent examination proceedings relating to EP-A-809629 and EP-A-915846:

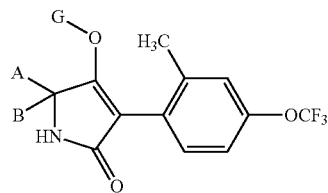

From EP-A-809629

| Ex. No. | A | B | G | Isomer |
|---|---|---|---|---|
| I-1-a-13 | —$(CH_2)_2$—$CHCH_3$—$(CH_2)_2$— | | H | β |
| I-1-a-14 | —$(CH_2)_2$—$CHOCH_3$—$(CH_2)_2$ | | H | β |
| I-1-b-14 | —$(CH_2)_2$—$CHCH_3$—$(CH_2)_2$— | | CO-i-$C_3H_7$ | β |
| I-1-b-15 | —$(CH_2)_2$—$CHCH_3$—$(CH_2)_2$— | | CO-$CH_2$-t-$C_4H_9$ | β |
| I-1-b-16 | —$(CH_2)_2$—$CHOCH_3$—$(CH_2)_2$— | | CO-i-$C_3H_7$ | β |
| I-1-b-17 | —$(CH_2)_2$—$CHOCH_3$—$(CH_2)_2$ | | CO-$CH_2$-t-$C_4H_9$ | β |
| I-1-c-9 | —$(CH_2)_2$—$CHCH_3$—$(CH_2)_2$— | | $CO_2C_2H_5$ | β |
| I-1-c-10 | —$(CH_2)_2$—$CHOCH_3$—$(CH_2)_2$ | | $CO_2C_2H_5$ | β |

From EP-A-915846

Ex. I-1-a-29

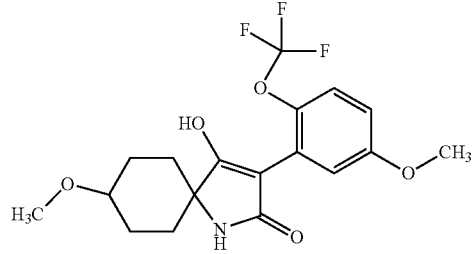

Furthermore, it has been found that the novel compounds of the formula (I) are very effective as pesticides, preferably as insecticides, acaricides and/or herbicides.

Surprisingly, it has now also been found that certain substituted cyclic ketoenols, when used together with the crop plant compatibility-improving compounds (safeners/antidotes) described below, efficiently prevent damage to the crop plants and can be used in a particularly advantageous manner as broad-spectrum combination preparations for the selective control of unwanted plants in crops of useful plants, such as, for example, in cereals, but also in maize, soya beans and rice.

The invention also provides selective herbicidal compositions comprising an effective amount of an active compound combination comprising, as components, (a') at least one trifluoromethoxyphenyl-substituted tetramic acid derivative of the formula (I) in which A, B, D, G, J, X and Y have the meaning given above
and (b') at least one crop plant compatibility-improving compound from the following group of compounds:

4-dichloroacetyl-1-oxa-4-azaspiro[4.5]decane (AD-67, MON-4660), 1-dichloroacetylhexahydro-3,3,8a-trimethylpyrrolo[1,2-a]pyrimidin-6(2H)-one (dicyclonon, BAS-145138), 4-dichloroacetyl-3,4-dihydro-3-methyl-2H-1,4-benzoxazine (benoxacor), 1-methylhexyl 5-chloroquinoline-8-oxyacetate (cloquintocet-mexyl—cf. also related compounds in EP-A-86750, EP-A-94349, EP-A-191736, EP-A-492366), 3-(2-chlorobenzyl)-1-(1-methyl-1-phenylethyl)urea (cumyluron), α-(cyanomethoximino)phenylacetonitrile (cyometrinil), 2,4-dichlorophenoxyacetic acid (2,4-D), 4-(2,4-dichlorophenoxy)butyric acid (2,4-DB), 1-(1-methyl-1-phenylethyl)-3-(4-methylphenyl)-urea (daimuron, dymron), 3,6-dichloro-2-methoxybenzoic acid (dicamba), S-1-methyl-1-phenylethyl piperidine-1-thiocarboxylate (dimepiperate), 2,2-dichloro-N-(2-oxo-2-(2-propenylamino)ethyl)-N-(2-propenyl)acetamide (DKA-24), 2,2-dichloro-N,N-di-2-propenylacetamide (dichlormid), 4,6-dichloro-2-phenylpyrimidine (fenclorim), ethyl 1-(2,4-dichlorophenyl)-5-trichloromethyl-1H-1,2,4-triazole-3-carboxylate (fenchlorazole-ethyl—cf. also related compounds in EP-A-174562 and EP-A-346620), phenylmethyl 2-chloro-4-trifluoromethylthiazole-5-carboxylate (flurazole), 4-chloro-N-(1,3-dioxolan-2-ylmethoxy)-α-trifluoroacetophenone oxime (fluxofenim), 3-dichloroacetyl-5-(2-furanyl)-2,2-dimethyloxazolidine (furilazole, MON-13900), ethyl 4,5-dihydro-5,5-diphenyl-3-isoxazolecarboxylate (isoxadifen-ethyl—cf. also related compounds in WO-A-95/07897), 1-(ethoxycarbonyl)ethyl 3,6-dichloro-2-methoxybenzoate (lactidichlor), (4-chloro-o-tolyloxy)acetic acid (MCPA), 2-(4-chloro-o-tolyloxy)propionic acid (mecoprop), diethyl 1-(2,4-dichlorophenyl)-4,5-dihydro-5-methyl-1H-pyrazole-3,5-dicarboxylate (mefenpyr-diethyl—cf. also related compounds in WO-A-91/07874) 2-dichloromethyl-2-methyl-1,3-dioxolane (MG-191), 2-propenyl-1-oxa-4-azaspiro[4.5]decane-4-carbodithioate (MG-838), 1,8-naphthalic anhydride, α-(1,3-dioxolan-2-ylmethoximino)phenylacetonitrile (oxabetrinil), 2,2-dichloro-N-(1,3-dioxolan-2-ylmethyl)-N-(2-propenyl)acetamide (PPG-1292), 3-dichloroacetyl-2,2-dimethyloxazolidine (R-28725), 3-dichloroacetyl-2,2,5-trimethyloxazolidine (R-29148), 4-(4-chloro-o-tolyl)butyric acid, 4-(4-chlorophenoxy)butyric acid, diphenylmethoxy-acetic acid, methyl diphenylmethoxyacetate, ethyl diphenylmethoxyacetate, methyl 1-(2-chloro-phenyl)-5-phenyl-1H-pyrazole-3-carboxylate, ethyl 1-(2,4-dichlorophenyl)-5-methyl-1H-pyrazole-3-carboxylate, ethyl 1-(2,4-dichlorophenyl)-5-isopropyl-1H-pyrazole-3-carboxylate, ethyl 1-(2,4-dichlorophenyl)-5-(1,1-dimethylethyl)-1H-pyrazole-3-carboxylate, ethyl 1-(2,4-dichlorophenyl)-5-phenyl-1H-pyrazole-3-carboxylate (cf. also related compounds in EP-A-269806 and EP-A-333131), ethyl 5-(2,4-dichlorobenzyl)-2-isoxazoline-3-carboxylate, ethyl 5-phenyl-2-isoxazoline-3-carboxylate, ethyl 5-(4-fluorophenyl)-5-phenyl-2-isoxazoline-3-carboxylate (cf. also related compounds in WO-A-91/08202), 1,3-dimethylbut-1-yl 5-chloroquinoline-8-oxyacetate, 4-allyloxybutyl 5-chloroquinoline-8-oxyacetate, 1-allyloxyprop-2-yl 5-chloroquinoline-8-oxyacetate, methyl 5-chloroquinoxaline-8-oxyacetate, ethyl 5-chloroquinoline-8-oxyacetate, allyl 5-chloroquinoxaline-8-oxyacetate, 2-oxoprop-1-yl 5-chloroquinoline-8-oxyacetate, diethyl 5-chloroquinoline-8-oxymalonate, diallyl 5-chloroquinoxaline-8-oxymalonate, diethyl 5-chloroquinoline-8-oxymalonate (cf. also related compounds in EP-A-582198), 4-carboxychroman-4-ylacetic acid (AC-304415, cf. EP-A-613618), 4-chlorophenoxy-acetic acid, 3,3'-dimethyl-4-methoxybenzophenone, 1-bromo-4-chloromethylsulphonylbenzene, 1-[4-(N-2-methoxybenzoylsulphamoyl)phenyl]-3-methylurea (also known as N-(2-methoxy-benzoyl)-4-[(methylaminocarbonyl)amino]benzenesulphonamide), 1-[4-(N-2-methoxybenzoylsulphamoyl)phenyl]-3,3-dimethylurea, 1-[4-(N-4,5-dimethylbenzoylsulphamoyl)phenyl]-3-methylurea, 1-[4-(N-naphthylsulphamoyl)phenyl]-3,3-dimethylurea, N-(2-methoxy-5-methyl-benzoyl)-4-(cyclopropylaminocarbonyl)benzenesulphonamide, and/or one of the following compounds, defined by general formulae
of the general formula (IIa)

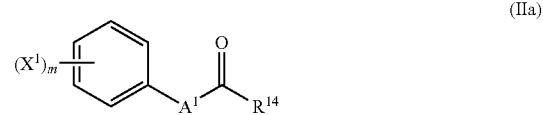

or of the general formula (IIb)

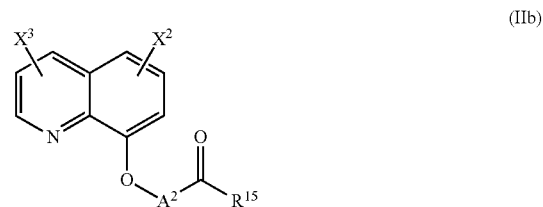

or of the formula (IIc)

where
m represents a number 0, 1, 2, 3, 4 or 5,
$A^1$ represents one of the divalent heterocyclic groupings shown below,

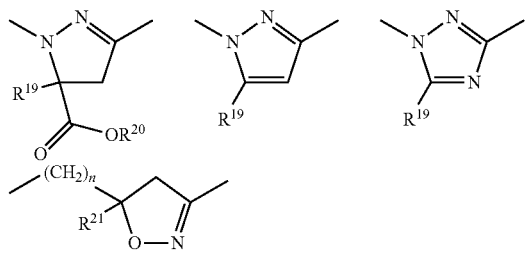

n represents a number 0, 1, 2, 3, 4 or 5,
$A^2$ represents optionally $C_1$-$C_4$-alkyl- and/or $C_1$-$C_4$-alkoxycarbonyl- and/or $C_1$-$C_4$-alkenyloxycarbonyl-substituted alkanediyl having 1 or 2 carbon atoms,
$R^{14}$ represents hydroxyl, mercapto, amino, $C_1$-$C_6$-alkoxy, $C_1$-$C_6$-alkylthio, $C_1$-$C_6$-alkylamino or di($C_1$-$C_4$-alkyl)-amino,
$R^{15}$ represents hydroxyl, mercapto, amino, $C_1$-$C_7$-alkoxy, $C_1$-$C_6$-alkenyloxy, $C_1$-$C_6$-alkenyloxy-$C_1$-$C_6$-alkoxy, $C_1$-$C_6$-alkylthio, $C_1$-$C_6$-alkylamino or di($C_1$-$C_4$-alkyl)-amino,
$R^{16}$ represents optionally fluorine-, chlorine- and/or bromine-substituted $C_1$-$C_4$-alkyl,
$R^{17}$ represents hydrogen, in each case optionally fluorine-, chlorine- and/or bromine-substituted $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or optionally fluorine-, chlorine- and/or bromine- or $C_1$-$C_4$-alkyl-substituted phenyl, $R^{18}$ represents hydrogen, in each case optionally fluorine-, chlorine- and/or bromine-substituted $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or optionally fluorine-, chlorine- and/or bromine- or $C_1$-$C_4$-alkyl-substituted phenyl, $R^{17}$ and $R^{18}$ also together represent $C_3$-$C_6$-alkanediyl or $C_2$-$C_5$-oxaalkanediyl, each of which is optionally substituted by $C_1$-$C_4$-alkyl, phenyl, furyl, a fused benzene ring or by two substituents which, together with the C atom to which they are attached, form a 5- or 6-membered carbocycle, $R^{19}$ represents hydrogen, cyano, halogen, or represents in each case optionally fluorine-, chlorine- and/or bromine-substituted $C_1$-$C_4$-alkyl, $C_3$-$C_6$-cycloalkyl or phenyl, $R^{20}$ represents hydrogen, optionally hydroxyl-, cyano-, halogen- or $C_1$-$C_4$-alkoxy-substituted $C_1$-$C_6$-alkyl, $C_3$-$C_6$-cycloalkyl or tri-($C_1$-$C_4$-alkyl)-silyl, $R^{21}$ represents hydrogen, cyano, halogen, or represents in each case optionally fluorine-, chlorine- and/or bromine-substituted $C_1$-$C_4$-alkyl, $C_3$-$C_6$-cycloalkyl or phenyl, $X^1$ represents nitro, cyano, halogen, $C_1$-$C_4$-alkyl, $C_1$-$C_4$-haloalkyl, $C_1$-$C_4$-alkoxy or $C_1$-$C_4$-haloalkoxy, $X^2$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, $X^3$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, and/or the following compounds, defined by general formulae of the general formula (IId)

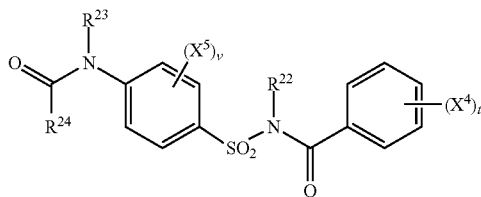

or of the general formula (IIe)

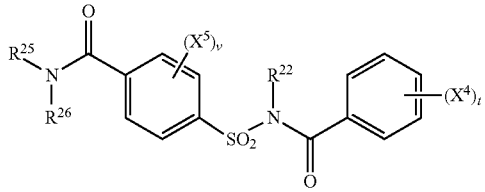

where t represents a number 0, 1, 2, 3, 4 or 5, v represents a number 0, 1, 2, 3, 4 or 5, $R^{22}$ represents hydrogen or $C_1$-$C_4$-alkyl, $R^{23}$ represents hydrogen or $C_1$-$C_4$-alkyl, $R^{24}$ represents hydrogen, in each case optionally cyano-, halogen- or $C_1$-$C_4$-alkoxy-substituted $C_1$-$C_6$-alkyl, $C_1$-$C_6$-alkoxy, $C_1$-$C_6$-alkylthio, $C_1$-$C_6$-alkylamino or di($C_1$-$C_4$-alkyl)-amino, or in each case optionally cyano-, halogen- or $C_1$-$C_4$-alkyl-substituted $C_3$-$C_6$-cycloalkyl, $C_3$-$C_6$-cycloalkyloxy, $C_3$-$C_6$-cycloalkylthio or $C_3$-$C_6$-cycloalkylamino, $R^{25}$ represents hydrogen, optionally cyano-, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, or optionally cyano-, halogen- or $C_1$-$C_4$-alkyl-substituted $C_3$-$C_6$-cycloalkyl, $R^{26}$ represents hydrogen, optionally cyano-, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, optionally cyano-, halogen- or $C_1$-$C_4$-alkyl-substituted $C_3$-$C_6$-cycloalkyl, or optionally nitro-, cyano-, halogen-, $C_1$-$C_4$-alkyl-, $C_1$-$C_4$-haloalkyl-, $C_1$-$C_4$-alkoxy- or $C_1$-$C_4$-haloalkoxy-substituted phenyl, or together with $R^{25}$ represents in each case optionally $C_1$-$C_4$-alkyl-substituted $C_2$-$C_6$-alkanediyl or $C_2$-$C_5$-oxaalkanediyl, $X^4$ represents nitro, cyano, carboxyl, carbamoyl, formyl, sulphamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy, and $X^5$ represents nitro, cyano, carboxyl, carbamoyl, formyl, sulphamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy.

The formula (I) provides a general definition of the compounds according to the invention. Preferred substituents or ranges of the radicals listed in the formulae mentioned above and below are illustrated below:

J preferably represents trifluoromethoxy,

X preferably represents hydrogen, halogen, $C_1$-$C_6$-alkyl, $C_1$-$C_4$-haloalkyl, $C_1$-$C_6$-alkoxy or $C_1$-$C_4$-haloalkoxy, Y preferably represents hydrogen, $C_1$-$C_6$-alkyl, $C_1$-$C_6$-alkoxy or halogen, with the proviso, that at least one of the radicals J, X and Y is located in the 2-position of the phenyl radical and is not hydrogen.

Here, the radicals J, X and Y, having their preferred meanings, are preferably arranged in the phenyl substitution patterns below (A)

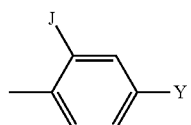

(B)

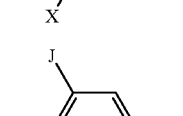

(C)

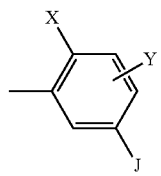

-continued

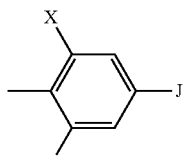
(D)

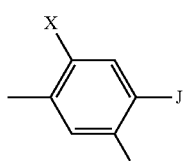
(E)

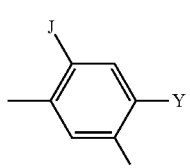
(K)

X, Y ≠ H where in the phenyl substitution patterns (C), (D) and (E) X and Y are simultaneously not hydrogen, A preferably represents hydrogen or in each case optionally halogen-substituted $C_1$-$C_{12}$-alkyl, $C_3$-$C_8$-alkenyl, $C_1$-$C_{10}$-alkoxy-$C_1$-$C_8$-alkyl, $C_1$-$C_{10}$-alkylthio-$C_1$-$C_6$-alkyl, optionally halogen-, $C_1$-$C_6$-alkyl- or $C_1$-$C_6$-alkoxy-substituted $C_3$-$C_8$-cycloalkyl in which optionally one or two not directly adjacent ring members are replaced by oxygen and/or sulphur or represents in each case optionally halogen-, $C_1$-$C_6$-alkyl-, $C_1$-$C_6$-haloalkyl-, $C_1$-$C_6$-alkoxy-, $C_1$-$C_6$-haloalkoxy-, cyano- or nitro-substituted phenyl, naphthyl, hetaryl having 5 to 6 ring atoms (for example furanyl, pyridyl, imidazolyl, triazolyl, pyrazolyl, pyrimidyl, thiazolyl or thienyl), phenyl-$C_1$-$C_6$-alkyl or naphthyl-$C_1$-$C_6$-alkyl, B preferably represents hydrogen, $C_1$-$C_{12}$-alkyl or $C_1$-$C_8$-alkoxy-$C_1$-$C_6$-alkyl or A, B and the carbon atom to which they are attached preferably represent saturated $C_3$-$C_{10}$-cycloalkyl or unsaturated $C_5$-$C_{10}$-cycloalkyl in which optionally one ring member is replaced by oxygen or sulphur and which are optionally mono- or disubstituted by $C_1$-$C_8$-alkyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl-$C_1$-$C_2$-alkoxy, $C_3$-$C_{10}$-cycloalkyl, $C_1$-$C_8$-haloalkyl, $C_1$-$C_8$-alkoxy, $C_1$-$C_8$-alkylthio, halogen or phenyl or A, B and the carbon atom to which they are attached preferably represent $C_3$-$C_6$-cycloalkyl which is substituted by an alkylenediyl group which is optionally substituted by $C_1$-$C_4$-alkyl and optionally contains one or two not directly adjacent oxygen and/or sulphur atoms, or by an alkylenedioxyl or by an alkylenedithioyl group which, together with the carbon atom to which it is attached, forms a further five- to eight-membered ring or A, B and the carbon atom to which they are attached preferably represent $C_3$-$C_8$-cycloalkyl or $C_5$-$C_8$-cycloalkenyl in which two substituents together with the carbon atoms to which they are attached represent in each case optionally $C_1$-$C_6$-alkyl-, $C_1$-$C_6$-alkoxy- or halogen-substituted $C_2$-$C_6$-alkanediyl, $C_2$-$C_6$-alkenediyl or $C_4$-$C_6$-alkanediendiyl in which optionally one methylene group is replaced by oxygen or sulphur, D preferably represents hydrogen, in each case optionally halogen-substituted $C_1$-$C_{12}$-alkyl, $C_3$-$C_8$-alkenyl, $C_3$-$C_8$-alkynyl, $C_1$-$C_{10}$-alkoxy-$C_2$-$C_8$-alkyl, optionally halogen-, $C_1$-$C_4$-alkyl-, $C_1$-$C_4$-alkoxy- or $C_1$-$C_4$-haloalkyl-substituted $C_3$-$C_8$-cycloalkyl in which optionally one ring member is replaced by oxygen or sulphur or in each case optionally halogen-, $C_1$-$C_6$-alkyl-, $C_1$-$C_6$-haloalkyl-, $C_1$-$C_6$-alkoxy-, $C_1$-$C_6$-haloalkoxy-, cyano- or nitro-substituted phenyl, hetaryl having 5 or 6 ring atoms (for example furanyl, imidazolyl, pyridyl, thiazolyl, pyrazolyl, pyrimidyl, pyrrolyl, thienyl or triazolyl), phenyl-$C_1$-$C_6$-alkyl or hetaryl-$C_1$-$C_6$-alkyl having 5 or 6 ring atoms (for example furanyl, imidazolyl, pyridyl, thiazolyl, pyrazolyl, pyrimidyl, pyrrolyl, thienyl or triazolyl) or A and D together preferably represent in each case optionally substituted $C_3$-$C_6$-alkanediyl or $C_3$-$C_6$-alkenediyl in which optionally one methylene group is replaced by a carbonyl group, oxygen or sulphur, possible substituents being in each case:

halogen, hydroxyl, mercapto or in each case optionally halogen-substituted $C_1$-$C_{10}$-alkyl, $C_1$-$C_6$-alkoxy, $C_1$-$C_6$-alkylthio, $C_3$-$C_7$-cycloalkyl, phenyl or benzyloxy, or a further $C_3$-$C_6$-alkanediyl grouping, $C_3$-$C_6$-alkenediyl grouping or a butadienyl grouping which is optionally substituted by $C_1$-$C_6$-alkyl or in which optionally two adjacent substituents together with the carbon atoms to which they are attached form a further saturated or unsaturated cycle having 5 or 6 ring atoms (in which case they represent, for example, groups AD-1 to AD-10 mentioned below) which may contain oxygen or sulphur or which optionally contains one of the following groups

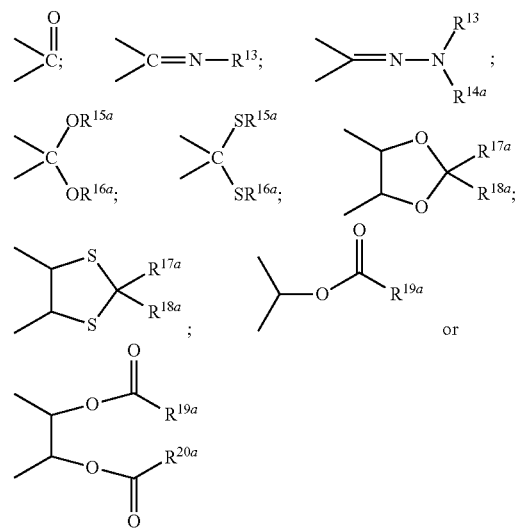

G preferably represents hydrogen (a) or represents one of the groups (b)

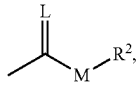
(c)

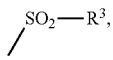
(d)

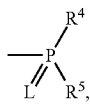
(e)

E or (f)

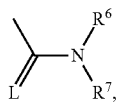
(g)

in particular (a), (b), (c) or (g)
in which
E represents a metal ion equivalent or an ammonium ion,
L represents oxygen or sulphur and
M represents oxygen or sulphur, $R^1$ preferably represents in each case optionally halogen-substituted $C_1$-$C_{20}$-alkyl, $C_2$-$C_{20}$-alkenyl, $C_1$-$C_8$-alkoxy-$C_1$-$C_8$-alkyl, $C_1$-$C_8$-alkylthio-$C_1$-$C_8$-alkyl, poly-$C_1$-$C_8$-alkoxy-$C_1$-$C_8$-alkyl or optionally halogen-, $C_1$-$C_6$-alkyl- or $C_1$-$C_6$-alkoxy-substituted $C_3$-$C_8$-cycloalkyl in which optionally one or more (preferably not more than two) not directly adjacent ring members are replaced by oxygen and/or sulphur, represents optionally halogen-, cyano-, nitro-, $C_1$-$C_6$-alkyl-, $C_1$-$C_6$-alkoxy-, $C_1$-$C_6$-haloalkyl-, $C_1$-$C_6$-haloalkoxy-, $C_1$-$C_6$-alkylthio- or $C_1$-$C_6$-alkylsulphonyl-substituted phenyl, represents optionally halogen-, nitro-, cyano-, $C_1$-$C_6$-alkyl-, $C_1$-$C_6$-alkoxy-, $C_1$-$C_6$-haloalkyl- or $C_1$-$C_6$-haloalkoxy-substituted phenyl-$C_1$-$C_6$-alkyl, represents optionally halogen- or $C_1$-$C_6$-alkyl-substituted 5- or 6-membered hetaryl (for example pyrazolyl, thiazolyl, pyridyl, pyrimidyl, furanyl or thienyl), represents optionally halogen- or $C_1$-$C_6$-alkyl-substituted phenoxy-$C_1$-$C_6$-alkyl or represents optionally halogen-, amino- or $C_1$-$C_6$-alkyl-substituted 5- or 6-membered hetaryloxy-$C_1$-$C_6$-alkyl (for example pyridyloxy-$C_1$-$C_6$-alkyl, pyrimidyloxy-$C_1$-$C_6$-alkyl or thiazolyloxy-$C_1$-$C_6$-alkyl), $R^2$ preferably represents in each case optionally halogen-substituted $C_1$-$C_{20}$-alkyl, $C_2$-$C_{20}$-alkenyl, $C_1$-$C_8$-alkoxy-$C_2$-$C_8$-alkyl, poly-$C_1$-$C_8$-alkoxy-$C_2$-$C_8$-alkyl, represents optionally halogen-, $C_1$-$C_6$-alkyl- or $C_1$-$C_6$-alkoxy-substituted $C_3$-$C_8$-cycloalkyl or represents in each case optionally halogen-, cyano-, nitro-, $C_1$-$C_6$-alkyl-, $C_1$-$C_6$-alkoxy-, $C_1$-$C_6$-haloalkyl- or $C_1$-$C_6$-haloalkoxy-substituted phenyl or benzyl, $R^3$ preferably represents optionally halogen-substituted $C_1$-$C_8$-alkyl or represents in each case optionally halogen-, $C_1$-$C_6$-alkyl-, $C_1$-$C_6$-alkoxy-, $C_1$-$C_4$-haloalkyl-, $C_1$-$C_4$-haloalkoxy-, cyano- or nitro-substituted phenyl or benzyl, $R^4$ and $R^5$ preferably independently of one another represent in each case optionally halogen-substituted $C_1$-$C_8$-alkyl, $C_1$-$C_8$-alkoxy, $C_1$-$C_8$-alkylamino, di-($C_1$-$C_8$-alkyl)amino, $C_1$-$C_8$-alkylthio, $C_2$-$C_8$-alkenylthio, $C_3$-$C_7$-cycloalkylthio or represent in each case optionally halogen-, nitro-, cyano-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkyl- or $C_1$-$C_4$-haloalkyl-substituted phenyl, phenoxy or phenylthio, $R^6$ and $R^7$ independently of one another preferably represent hydrogen, represent in each case optionally halogen-substituted $C_1$-$C_8$-alkyl, $C_3$-$C_8$-cycloalkyl, $C_1$-$C_8$-alkoxy, $C_3$-$C_8$-alkenyl, $C_1$-$C_8$-alkoxy-$C_1$-$C_8$-alkyl, represent optionally halogen-, $C_1$-$C_8$-haloalkyl-, $C_1$-$C_8$-alkyl- or $C_1$-$C_8$-alkoxy-substituted phenyl, optionally halogen-, $C_1$-$C_8$-alkyl-, $C_1$-$C_8$-haloalkyl- or $C_1$-$C_8$-alkoxy-substituted benzyl or together represent an optionally $C_1$-$C_4$-alkyl-substituted $C_3$-$C_6$-alkylene radical in which optionally one carbon atom is replaced by oxygen or sulphur, $R^{13}$ preferably represents hydrogen, represents in each case optionally halogen-substituted $C_1$-$C_8$-alkyl or $C_1$-$C_8$-alkoxy, represents optionally halogen-, $C_1$-$C_4$-alkyl- or $C_1$-$C_4$-alkoxy-substituted $C_3$-$C_8$-cycloalkyl in which optionally one methylene group is replaced by oxygen or sulphur, or represents in each case optionally halogen-, $C_1$-$C_6$-alkyl-, $C_1$-$C_6$-alkoxy-, $C_1$-$C_4$-haloalkyl-, $C_1$-$C_4$-haloalkoxy-, nitro- or cyano-substituted phenyl, phenyl-$C_1$-$C_4$-alkyl or phenyl-$C_1$-$C_4$-alkoxy, $R^{14a}$ preferably represents hydrogen or $C_1$-$C_8$-alkyl or $R^{13}$ and $R^{14a}$ together preferably represent $C_4$-$C_6$-alkanediyl, $R^{15a}$ and $R^{16a}$ are identical or different and preferably represent $C_1$-$C_6$-alkyl or $R^{15a}$ and $R^{16a}$ together preferably represent a $C_2$-$C_4$-alkanediyl radical which is optionally substituted by $C_1$-$C_6$-alkyl, $C_1$-$C_6$-haloalkyl or by optionally halogen-, $C_1$-$C_6$-alkyl-, $C_1$-$C_4$-haloalkyl-, $C_1$-$C_6$-alkoxy-, $C_1$-$C_4$-haloalkoxy-, nitro- or cyano-substituted phenyl, $R^{17a}$ and $R^{18a}$ independently of one another preferably represent hydrogen, represent optionally halogen-substituted $C_1$-$C_8$-alkyl or represent optionally halogen-, $C_1$-$C_6$-alkyl-, $C_1$-$C_6$-alkoxy-, $C_1$-$C_4$-haloalkyl-, $C_1$-$C_4$-haloalkoxy-, nitro- or cyano-substituted phenyl or $R^{17a}$ and $R^{18a}$ together with the carbon atom to which they are attached preferably represent a carbonyl group or represent optionally halogen-, $C_1$-$C_4$-alkyl- or $C_1$-$C_4$-alkoxy-substituted $C_5$-$C_7$-cycloalkyl in which optionally one methylene group is replaced by oxygen or sulphur, $R^{19a}$ and $R^{20a}$ independently of one another preferably represent $C_1$-$C_{10}$-alkyl, $C_2$-$C_{10}$-alkenyl, $C_1$-$C_{10}$-alkoxy, $C_1$-$C_{10}$-alkylamino, $C_3$-$C_{10}$-alkenylamino, di-($C_1$-$C_{10}$-alkyl)amino or di-($C_3$-$C_{10}$-alkenyl)amino.

In the radical definitions mentioned as being preferred, halogen represents fluorine, chlorine, bromine and iodine, in particular fluorine, chlorine and bromine.

J particularly preferably represents trifluoromethoxy,

X particularly preferably represents hydrogen, fluorine, chlorine, bromine, $C_1$-$C_4$-alkyl, trifluoromethyl or $C_1$-$C_4$-alkoxy, Y particularly preferably represents hydrogen, fluorine, chlorine, bromine, $C_1$-$C_4$-alkoxy or $C_1$-$C_4$-alkyl with the proviso, that at least one of the radicals J, X and Y is located in the 2-position of the phenyl radical and is not hydrogen.

Here, the radicals J, X and Y, having their particularly preferred meanings, are particularly preferably arranged in the phenyl substitution patterns below (A) 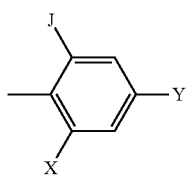

(B) 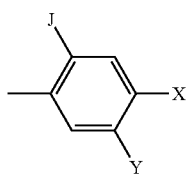

(C) 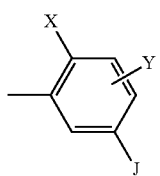

(D) 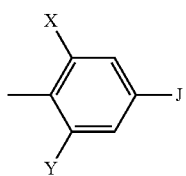

(E) 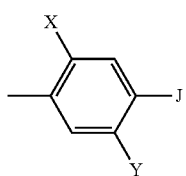

(K) 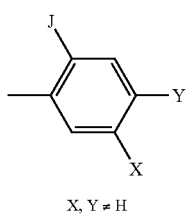

X, Y ≠ H where in the phenyl substitution patterns (C), (D) and (E) X and Y are simultaneously not hydrogen, A particularly preferably represents hydrogen, represents $C_1$-$C_6$-alkyl or $C_1$-$C_4$-alkoxy-$C_1$-$C_2$-alkyl, each of which is optionally mono- to trisubstituted by fluorine or chlorine, represents $C_3$-$C_6$-cycloalkyl which is optionally mono- or disubstituted by $C_1$-$C_2$-alkyl or $C_1$-$C_2$-alkoxy and which may optionally be interrupted by an oxygen atom, represents phenyl or benzyl, each of which is optionally mono- or disubstituted by fluorine, chlorine, bromine, $C_1$-$C_4$-alkyl, $C_1$-$C_2$-haloalkyl, $C_1$-$C_4$-alkoxy, $C_1$-$C_2$-haloalkoxy, cyano or nitro, B particularly preferably represents hydrogen, $C_1$-$C_4$-alkyl or $C_1$-$C_2$-alkoxyl-$C_1$-$C_2$-alkyl or A, B and the carbon atom to which they are attached particularly preferably represent saturated or unsaturated $C_5$-$C_7$-cycloalkyl in which optionally one ring member is replaced by oxygen or sulphur and which is optionally mono- or disubstituted by $C_1$-$C_6$-alkyl, $C_1$-$C_4$-alkoxy-$C_1$-$C_2$-alkyl, $C_1$-$C_4$-alkoxy-$C_1$-$C_2$-alkoxy, $C_3$-$C_6$-cycloalkyl-methoxy, trifluoromethyl or $C_1$-$C_6$-alkoxy, or A, B and the carbon atom to which they are attached particularly preferably represent $C_5$-$C_6$-cycloalkyl which is substituted by an alkylenediyl group which is optionally substituted by methyl or ethyl and optionally contains one or two not directly adjacent oxygen or sulphur atoms, or by an alkylenedioxyl or by an alkylenedithiol group which, together with the carbon atom to which it is attached, forms a further five- or six-membered ring, or A, B and the carbon atom to which they are attached particularly preferably represent $C_3$-$C_6$-cycloalkyl or $C_5$-$C_6$-cycloalkenyl in which two substituents together with the carbon atoms to which they are attached represent in each case optionally $C_1$-$C_2$-alkyl- or $C_1$-$C_2$-alkoxy-substituted $C_2$-$C_4$-alkanediyl, $C_2$-$C_4$-alkenediyl or butadienediyl, D particularly preferably represents hydrogen, represents $C_1$-$C_6$-alkyl, $C_3$-$C_6$-alkenyl or $C_1$-$C_4$-alkoxy-$C_2$-$C_3$-alkyl, each of which is optionally mono- to trisubstituted by fluorine, represents $C_3$-$C_6$-cycloalkyl which is optionally mono- or disubstituted by $C_1$-$C_4$-alkyl, $C_1$-$C_4$-alkoxy or $C_1$-$C_2$-haloalkyl and in which optionally one methylene group is replaced by oxygen, or A and D together particularly preferably represent $C_3$-$C_5$-alkanediyl in which one methylene group may be replaced by a carbonyl group, oxygen or sulphur and which is optionally mono- or disubstituted, possible substituents being $C_1$-$C_2$-alkyl or $C_1$-$C_2$-alkoxy or A and D together with the atoms to which they are attached represent one of the groups AD-1 to AD-10:

AD-1 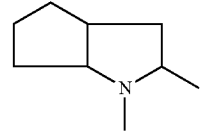

AD-2 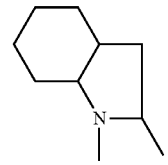

AD-3 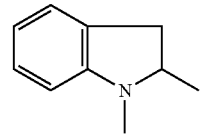

AD-4 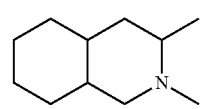

AD-5 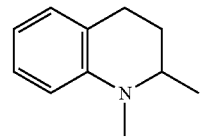

AD-6 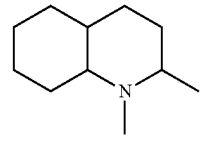

-continued

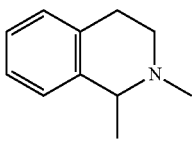
AD-7

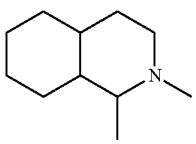
AD-8

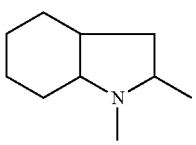
AD-9

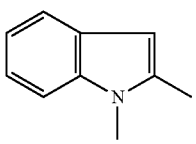
AD-10

G particularly preferably represents hydrogen (a) or represents one of the groups

(b)

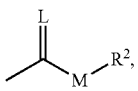
(c)

(d)

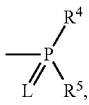
(e)

E or
(f)

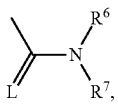
(g)

in which

E represents a metal ion equivalent or an ammonium ion,

L represents oxygen or sulphur and

M represents oxygen or sulphur, $R^1$ particularly preferably represents $C_1$-$C_8$-alkyl, $C_2$-$C_{18}$-alkenyl, $C_1$-$C_4$-alkoxy-$C_1$-$C_2$-alkyl or $C_1$-$C_4$-alkylthio-$C_1$-$C_2$-alkyl, each of which is optionally mono- to trisubstituted by fluorine or chlorine, or $C_3$-$C_6$-cycloalkyl which is optionally mono- or disubstituted by fluorine, chlorine, $C_1$-$C_2$-alkyl or $C_1$-$C_2$-alkoxy and in which optionally one or two not directly adjacent ring members are replaced by oxygen, represents phenyl which is optionally mono- or disubstituted by fluorine, chlorine, bromine, cyano, nitro, $C_1$-$C_4$-alkyl, $C_1$-$C_4$-alkoxy, $C_1$-$C_2$-haloalkyl or $C_1$-$C_2$-haloalkoxy, $R^2$ particularly preferably represents $C_1$-$C_8$-alkyl, $C_2$-$C_8$-alkenyl or $C_1$-$C_4$-alkoxy-$C_2$-$C_4$-alkyl, each of which is optionally mono- to trisubstituted by fluorine, represents $C_3$-$C_6$-cycloalkyl which is optionally monosubstituted by $C_1$-$C_2$-allyl or $C_1$-$C_2$-alkoxy or represents phenyl or benzyl, each of which is optionally mono- or disubstituted by fluorine, chlorine, bromine, cyano, nitro, $C_1$-$C_4$-alkyl, $C_1$-$C_3$-alkoxy, trifluoromethyl or trifluoromethoxy, $R^3$ particularly preferably represents $C_1$-$C_6$-alkyl which is optionally mono- to trisubstituted by fluorine or represents phenyl which is optionally monosubstituted by fluorine, chlorine, bromine, $C_1$-$C_4$-alkyl, $C_1$-$C_4$-alkoxy, trifluoromethyl, trifluoromethoxy, cyano or nitro, $R^4$ particularly preferably represents $C_1$-$C_6$-alkyl, $C_1$-$C_6$-alkoxy, $C_1$-$C_6$-alkylamino, di-($C_1$-$C_6$-alkyl)amino, $C_1$-$C_6$-alkylthio, $C_3$-$C_4$-alkenylthio, $C_3$-$C_6$-cycloalkylthio or represents phenyl, phenoxy or phenylthio, each of which is optionally monosubstituted by fluorine, chlorine, bromine, nitro, cyano, $C_1$-$C_3$-alkoxy, $C_1$-$C_3$-haloalkoxy, $C_1$-$C_3$-alkylthio, $C_1$-$C_3$-haloalkylthio, $C_1$-$C_3$-alkyl or trifluoromethyl, $R^5$ particularly preferably represents $C_1$-$C_6$-alkoxy or $C_1$-$C_6$-alkylthio, $R^6$ particularly preferably represents hydrogen, $C_1$-$C_6$-alkyl, $C_3$-$C_6$-cycloalkyl, $C_1$-$C_6$-alkoxy, $C_3$-$C_6$-alkenyl, $C_1$-$C_6$-alkoxy-$C_1$-$C_4$-alkyl, represents phenyl which is optionally monosubstituted by fluorine, chlorine, bromine, trifluoromethyl, $C_1$-$C_4$-alkyl or $C_1$-$C_4$-alkoxy, represents benzyl which is optionally monosubstituted by fluorine, chlorine, bromine, $C_1$-$C_4$-alkyl, trifluoromethyl or $C_1$-$C_4$-alkoxy, $R^7$ particularly preferably represents $C_1$-$C_6$-alkyl, $C_3$-$C_6$-alkenyl or $C_1$-$C_6$-alkoxy-$C_1$-$C_4$-alkyl, $R^6$ and $R^7$ particularly preferably together represent an optionally methyl- or ethyl-substituted $C_4$-$C_5$-alkylene radical in which optionally one methylene group is replaced by oxygen or sulphur.

In the radical definitions mentioned as being particularly preferred, halogen represents fluorine, chlorine and bromine, in particular fluorine and chlorine.

J very particularly preferably represents trifluoromethoxy,

X very particularly preferably represents hydrogen, fluorine, chlorine, bromine, methyl, ethyl, propyl, methoxy or ethoxy, Y very particularly preferably represents hydrogen, chlorine, bromine, methyl, ethyl or methoxy, with the proviso, that at least one of the radicals J, X and Y is located in the 2-position of the phenyl radical and is not hydrogen.

Here, the radicals J, X and Y, having their very particularly preferred meanings, are very particularly preferably arranged in the phenyl substitution patterns below

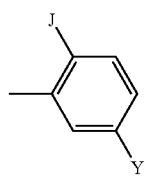
(F)

-continued

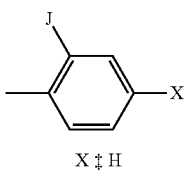

X ‡ H

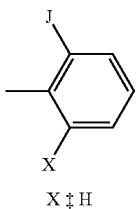

X ‡ H

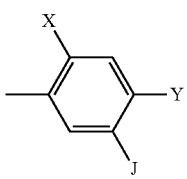

X, Y ‡ H

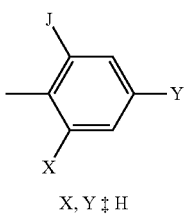

X, Y ‡ H

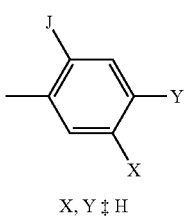

X, Y ‡ H

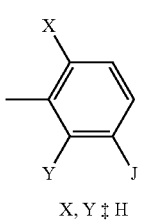

X, Y ‡ H

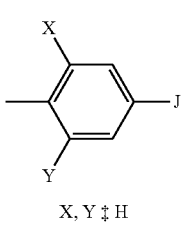

X, Y ‡ H

-continued (G)

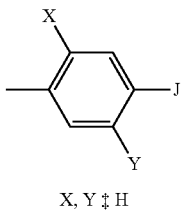

(H)

X, Y ‡ H (N)

A very particularly preferably represents hydrogen, represents $C_1$-$C_4$-alkyl or $C_1$-$C_2$-alkoxy-$C_1$-$C_2$-alkyl, each of which is optionally mono- to trisubstituted by fluorine, represents cyclopropyl, cyclopentyl or cyclohexyl, represents in each case optionally fluorine-, chlorine-, bromine-, methyl-, ethyl-, n-propyl-, isopropyl-, methoxy-, ethoxy-, trifluoromethyl-, trifluoromethoxy-, cyano- or nitro-substituted phenyl or benzyl, B very particularly preferably represents hydrogen, methyl or ethyl or A, B and the carbon atom to which they are attached very particularly preferably represent saturated $C_5$-$C_6$-cycloalkyl in which optionally one ring member is replaced by oxygen or sulphur and which is optionally monosubstituted by methyl, ethyl, propyl, isopropyl, methoxymethyl, ethoxymethyl, propoxymethyl, trifluoromethyl, methoxy, ethoxy, propoxy, butoxy, methoxyethyl, ethoxyethyl, methoxyethoxy, ethoxyethoxy, cyclopropylmethoxy, cyclopentylmethoxy or cyclohexylmethoxy, or A, B and the carbon atom to which they are attached very particularly preferably represent $C_6$-cycloalkyl which is optionally substituted by an alkylenedioxyl group which contains two not directly adjacent oxygen atoms, or A, B and the carbon atom to which they are attached very particularly preferably represent $C_5$-$C_6$-cycloalkyl or $C_5$-$C_6$-cycloalkenyl in which two substituents together with the carbon atoms to which they are attached represent $C_2$-$C_4$-alkanediyl or $C_2$-$C_4$-alkenediyl or butadienediyl, D very particularly preferably represents hydrogen, represents $C_1$-$C_4$-alkyl, $C_3$-$C_4$-alkenyl, $C_1$-$C_4$-alkoxy-$C_2$-$C_3$-alkyl, represents cyclopropyl, cyclopentyl or cyclohexyl, each of which is optionally mono- to trisubstituted by fluorine, or A and D together very particularly preferably represent $C_3$-$C_5$-alkanediyl which is optionally monosubstituted by methyl or methoxy and in which optionally one carbon atom is replaced by oxygen or sulphur, or represent the group AD-1, G very particularly preferably represents hydrogen (a) or represents one of the groups

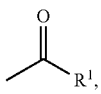

(b)

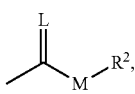

(c)

—$SO_2$—$R^3$ (d) or E (f), in particular (a), (b), (c) or (f)

in which

L represents oxygen or sulphur,

M represents oxygen or sulphur and

E represents an ammonium ion, $R^1$ very particularly preferably represents $C_1$-$C_6$-alkyl, $C_2$-$C_{17}$-alkenyl, $C_1$-$C_2$-alkoxy-$C_1$-alkyl, $C_1$-$C_2$-alkylthio-$C_1$-alkyl or represents cyclopropyl or cyclohexyl, each of which is optionally monosubstituted by fluorine, chlorine, methyl or methoxy, represents phenyl which is optionally monosubstituted by fluorine, chlorine, bromine, cyano, nitro, methyl, methoxy, trifluoromethyl or trifluoromethoxy, $R^2$ very particularly preferably represents $C_1$-$C_8$-alkyl, $C_2$-$C_6$-alkenyl or $C_1$-$C_4$-alkoxy-$C_2$-$C_3$-alkyl, phenyl or benzyl, each of which is optionally monosubstituted by fluorine, $R^3$ very particularly preferably represents $C_1$-$C_8$-alkyl.

J notably represents trifluoromethoxy,

X notably represents hydrogen, chlorine, bromine, methyl, ethyl or methoxy,

Y notably represents hydrogen, chlorine, bromine, methyl or methoxy, with the proviso, that at least one of the radicals J, X and Y is located in the 2-position of the phenyl radical and is not hydrogen.

Here, the radicals J, X and Y, having their very particularly preferred meanings, are notably arranged in the phenyl substitution patterns below

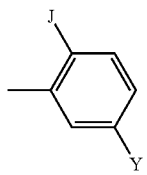
(F)

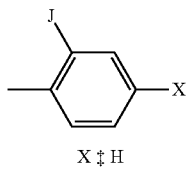
(G)
X ‡ H

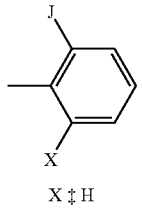
(H)
X ‡ H

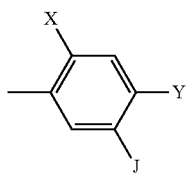
(I)

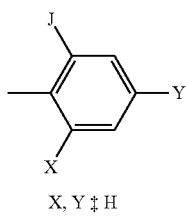
(J)
X, Y ‡ H

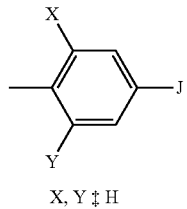
(M)
X, Y ‡ H

A notably represents $C_1$-$C_4$-alkyl or cyclopropyl,

B notably represents hydrogen or methyl,

A, B and the carbon atom to which they are attached notably represent saturated $C_5$-$C_6$-cycloalkyl in which optionally one ring member is replaced by oxygen and which is optionally monosubstituted by methoxymethyl, methoxy, ethoxy, propoxy or butoxy, or represent

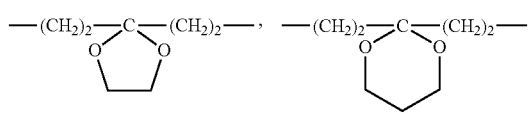

D notably represents hydrogen or cyclopropyl, or

A and D together notably represent $C_3$-$C_5$-alkanediyl,

G notably represents hydrogen (a) or represents one of the groups

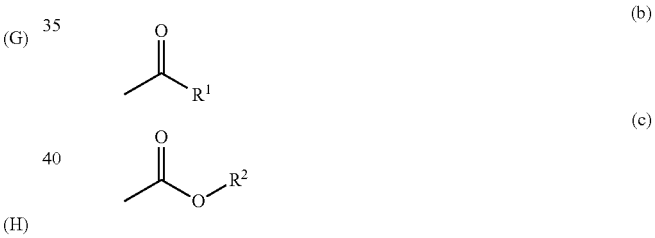

$R^1$ notably represents $C_1$-$C_6$-alkyl, $R^2$ notably represents $C_1$-$C_8$-alkyl or benzyl.

The general or preferred radical definitions or illustrations listed above can be combined with one another as desired, i.e. including combinations between the respective ranges and preferred ranges. They apply both to the end products and, correspondingly, to precursors and intermediates.

Preference according to the invention is given to the compounds of the formula (I) which contain a combination of the meanings listed above as being preferred (preferable).

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

Noteworthiness in accordance with the invention is accorded to the compounds of the formula (I) in which there is a combination of the definitions set out above as being notable.

Saturated or unsaturated hydrocarbon radicals, such as alkyl, alkanediyl or alkenyl, can in each case be straight-chain or branched as far as this is possible, including in combination with heteroatoms, such as, for example, in alkoxy.

Optionally substituted radicals can be mono- or polysubstituted unless indicated otherwise, and in the case of multiple substitutions the substituents can be identical or different.

In addition to the compounds mentioned in the Preparation Examples, the following compounds of the formula (I-1-a) may be specifically mentioned:

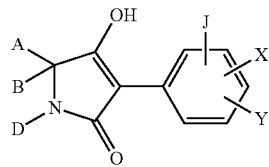

TABLE 1

| 2-OCF$_3$; X=H; Y=H. | | |
|---|---|---|
| A | B | D |
| CH$_3$ | H | H |
| C$_2$H$_5$ | H | H |
| C$_3$H$_7$ | H | H |
| i-C$_3$H$_7$ | H | H |
| C$_4$H$_9$ | H | H |
| i-C$_4$H$_9$ | H | H |
| s-C$_4$H$_9$ | H | H |
| t-C$_4$H$_9$ | H | H |
| CH$_3$ | CH$_3$ | H |
| C$_2$H$_5$ | CH$_3$ | H |
| C$_3$H$_7$ | CH$_3$ | H |
| i-C$_3$H$_7$ | CH$_3$ | H |
| C$_4$H$_9$ | CH$_3$ | H |
| i-C$_4$H$_9$ | CH$_3$ | H |
| s-C$_4$H$_9$ | CH$_3$ | H |
| t-C$_4$H$_9$ | CH$_3$ | H |
| C$_2$H$_5$ | C$_2$H$_5$ | H |
| C$_3$H$_7$ | C$_3$H$_7$ | H |
|  | CH$_3$ | H |
| 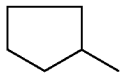 | CH$_3$ | H |
| 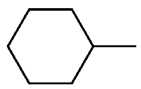 | CH$_3$ | H |
| —(CH$_2$)$_2$— | | H |
| —(CH$_2$)$_4$— | | H |
| —(CH$_2$)$_5$— | | H |
| —(CH$_2$)$_6$— | | H |
| —(CH$_2$)$_7$— | | H |
| —(CH$_2$)$_2$—O—(CH$_2$)$_2$— | | H |
| —CH$_2$—O—(CH$_2$)$_3$— | | H |
| —(CH$_2$)$_2$—S—(CH$_2$)$_2$— | | H |
| —CH$_2$—CHCH$_3$—(CH$_2$)$_3$— | | H |
| —(CH$_2$)$_2$—CHCH$_3$—(CH$_2$)$_2$— | | H |
| —(CH$_2$)$_2$—CHC$_2$H$_5$—(CH$_2$)$_2$— | | H |
| —(CH$_2$)$_2$—CHC$_3$H$_7$—(CH$_2$)$_2$— | | H |
| —(CH$_2$)$_2$—CHi-C$_3$H$_7$—(CH$_2$)$_2$— | | H |
| —CH$_2$—CHOCH$_3$—(CH$_2$)$_3$— | | H |
| —CH$_2$—CHOC$_2$H$_5$—(CH$_2$)$_3$— | | H |
| CH$_2$—CHOC$_3$H$_7$—(CH$_2$)$_3$— | | H |
| —CH$_2$—CHOC$_4$H$_9$—(CH$_2$)$_3$— | | H |
| —CH$_2$—CHO—(CH$_2$)$_2$—OCH$_3$—(CH$_2$)$_3$— | | H |

TABLE 1-continued

| | |
|---|---|
| —CH$_2$—CH(O—CH$_2$)—(CH$_2$)$_3$— | H |
|  | |
| —(CH$_2$)$_2$—CHOCH$_3$—(CH$_2$)$_2$— | H |
| —(CH$_2$)$_2$—CHOC$_2$H$_5$—(CH$_2$)$_2$- | H |
| —(CH$_2$)$_2$—CHOC$_3$H$_7$—(CH$_2$)$_2$— | H |
| —(CH$_2$)$_2$—CHO-i-C$_3$H$_7$—(CH$_2$)$_2$— | H |
| —CH$_2$—CH(CH$_2$—OCH$_3$)—(CH$_2$)$_3$— | H |
| —CH$_2$—CH(CH$_2$—CH$_2$—OCH$_3$)—(CH$_2$)$_3$— | H |
| —(CH$_2$)$_2$—CH(CH$_2$—OCH$_3$)—(CH$_2$)$_2$— | H |
| —(CH$_2$)$_2$—CH(CH$_2$—CH$_2$—OCH$_3$)—(CH$_2$)$_2$— | H |
| —(CH$_2$)$_2$—C(CH$_3$)$_2$—(CH$_2$)$_2$— | H |
| —CH$_2$—(CHCH$_3$)$_2$—(CH$_2$)$_2$— | H |
| 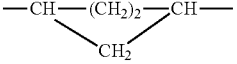 | H |
| 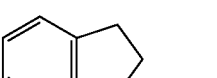 | H |
| 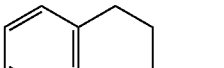 | H |
| 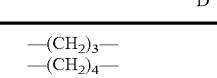 | H |
| 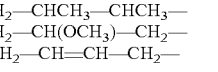 | H |

| A | D | B |
|---|---|---|
| —(CH$_2$)$_3$— | | H |
| —(CH$_2$)$_4$— | | H |
| —CH$_2$—CHCH$_3$—CH$_2$— | | H |
| —CH$_2$—CH$_2$—CHCH$_3$— | | H |
| —CH$_2$—CHCH$_3$—CHCH$_3$— | | H |
| —CH$_2$—CH(OCH$_3$)—CH$_2$— | | H |
| —CH$_2$—CH=CH—CH$_2$— | | H |
| 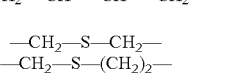 | | H |
| —CH$_2$—S—CH$_2$— | | H |
| —CH$_2$—S—(CH$_2$)$_2$— | | H |
| —(CH$_2$)$_2$—S—CH$_2$— | | H |
| 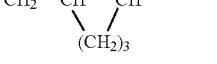 | | H |
| H | CH$_3$ | H |
| H | C$_2$H$_5$ | H |
| H | C$_3$H$_7$ | H |
| H | i-C$_3$H$_7$ | H |
| H |  | H |
| H | 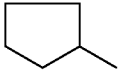 | H |
| H | 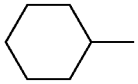 | H |

TABLE 1-continued

| | | |
|---|---|---|
| CH$_3$ | CH$_3$ | H |
| CH$_3$ | C$_2$H$_5$ | H |
| CH$_3$ | C$_3$H$_7$ | H |
| CH$_3$ | i-C$_3$H$_7$ | H |
| CH$_3$ |  | H |
| CH$_3$ |  | H |
| CH$_3$ |  | H |
| —CH$_2$—CH— | —CH— | H |
|           CH$_2$—O—CH$_2$ | | |
| C$_2$H$_5$ | CH$_3$ | H |
| C$_2$H$_5$ | C$_2$H$_5$ | H |

Table 2:
  A, B and D as Stated in Table 1
  J=2-OCF$_3$; X=4-CH$_3$; Y=H
Table 3:
  A, B and D as Stated in Table 1
  J=2-OCF$_3$; X=6-CH$_3$; Y=H.
Table 4:
  A, B and D as Stated in Table 1
  J=2-OCF$_3$; X=6-C$_2$H$_5$; Y=H.
Table 5:
  A, B and D as Stated in Table 1
  X=2-CH$_3$; Y=H; J=5-OCF$_3$.
Table 6:
  A, B and D as Stated in Table 1
  X=2-CH$_3$; Y=4-CH$_3$; J=5-OCF$_3$.
Table 7:
  A, B and D as Stated in Table 1
  J=2-OCF$_3$; X=4-CH$_3$; Y=6-CH$_3$.
Table 8:
  A, B and D as Stated in Table 1
  J=2-OCF$_3$; X=6-C$_2$H$_5$; Y=4-CH$_3$.
Table 9:
  A, B and D as Stated in Table 1
  J=2-OCF$_3$; X=6-CH$_3$; Y=4-Cl.
Table 10:
  A, B and D as Stated in Table 1
  J=2-OCF$_3$; X=6-C$_2$H$_5$; Y=4-Cl.
Table 11:
  A, B and D as Stated in Table 1
  J=2-OCF$_3$; X=6-Cl; Y=4-CH$_3$.
Table 12:
  A, B and D as Stated in Table 1
  J=2-OCF$_3$; X=5-CH$_3$; Y=4-CH$_3$.
Table 13:
  A, B and D as Stated in Table 1
  X=2-CH$_3$; J=4-OCF$_3$; Y=6-CH$_3$.
Table 14:
  A, B and D as Stated in Table 1
  X=2-C$_2$H$_5$; J=4-OCF$_3$; Y=6-CH$_3$.
Table 15:
  A, B and D as Stated in Table 1
  X=2-C$_2$H$_5$; J=4-OCF$_3$; Y=6-C$_2$H$_5$.
Table 16:
  A, B and D as Stated in Table 1
  X=2-Cl; J=4-OCF$_3$; Y=6-CH$_3$.
Table 17:
  A, B and D as Stated in Table 1
  X=2-Cl; J=4-OCF$_3$; Y=6-C$_2$H$_5$.
Table 18:
  A, B and D as Stated in Table 1
  X=2-Cl; J=4-OCF$_3$; Y=H.
Table 19:
  A, B and D as Stated in Table 1
  X=2-Br; J=4-OCF$_3$; Y=H.
Table 20:
  A, B and D as Stated in Table 1
  X=2-OCH$_3$; J=4-OCF$_3$; Y=6-Cl.
Table 21:
  A, B and D as Stated in Table 1
  X=2-OCH$_3$; J=6-OCF$_3$; Y=4-Cl.
Table 22:
  A, B and D as Stated in Table 1
  J=2-OCF$_3$; X=6-Cl; Y=4-Cl.
Table 23:
  A, B and D as Stated in Table 1
  J=2-OCF$_3$; X=6-Cl; Y=4-Br.
Table 24:
  A, B and D as Stated in Table 1
  J=2-OCF$_3$; X=6-Br; Y=4-Br.
Table 25:
  A, B and D as Stated in Table 1
  J=4-OCF$_3$; X=2-Cl; Y=6-Cl.
Table 26:
  A, B and D as Stated in Table 1
  J=4-OCF$_3$; X=2-Br; Y=6-Cl.
Table 27:
  A, B and D as Stated in Table 1
  X=2-Br; J=4-OCF$_3$; Y=6-Br.
Table 28:
  A, B and D as Stated in Table 1
  X=2-Cl; J=5-OCF$_3$; Y=H.
Table 29:
  A, B and D as Stated in Table 1
  X=2-Br; J=5-OCF$_3$; Y=H.
Table 30:
  A, B and D as Stated in Table 1
  X=H; J=2-OCF$_3$; Y=5-CH$_3$.

Preferred meanings of the groups listed above in connection with the crop plant compatibility-improving compounds ("herbicide safeners") of the formulae (IIa), (IIb), (IIc), (IId) and (IIe) are defined below.

m preferably represents the numbers 0, 1, 2, 3 or 4.

A$^1$ preferably represents one of the divalent heterocyclic groupings shown below

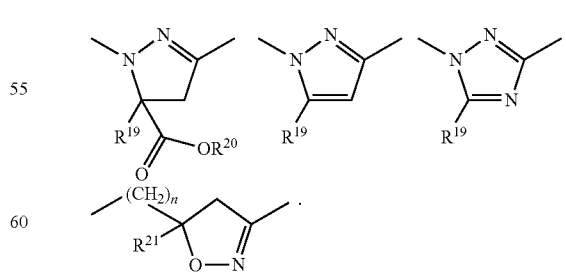

n preferably represents the numbers 0, 1, 2, 3 or 4.

A$^2$ preferably represents in each case optionally methyl-, ethyl-, methoxycarbonyl- or ethoxycarbonyl-substituted methylene or ethylene.

$R^{14}$ preferably represents hydroxyl, mercapto, amino, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino.

$R^{15}$ preferably represents hydroxyl, mercapto, amino, methoxy, ethoxy, n- or i-propoxy, n-, i-, s- or t-butoxy, 1-methylhexyloxy, allyloxy, 1-allyloxymethylethoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino.

$R^{16}$ preferably represents in each case optionally fluorine-, chlorine- and/or bromine-substituted methyl, ethyl, n- or i-propyl.

$R^{17}$ preferably represents hydrogen, in each case optionally fluorine- and/or chlorine-substituted methyl, ethyl, n- or i-propyl, n-, i-, s- or t-butyl, propenyl, butenyl, propynyl or butynyl, methoxymethyl, ethoxymethyl, methoxyethyl, ethoxyethyl, dioxolanylmethyl, furyl, furyl-methyl, thienyl, thiazolyl, piperidinyl, or optionally fluorine-, chlorine-, methyl-, ethyl-, n- or i-propyl-, n-, i-, s- or t-butyl-substituted phenyl.

$R^{18}$ preferably represents hydrogen, in each case optionally fluorine- and/or chlorine-substituted methyl, ethyl, n- or i-propyl, n-, i-, s- or t-butyl, propenyl, butenyl, propynyl or butynyl, methoxymethyl, ethoxymethyl, methoxyethyl, ethoxyethyl, dioxolanylmethyl, furyl, furyl-methyl, thienyl, thiazolyl, piperidinyl, or optionally fluorine-, chlorine-, methyl-, ethyl-, n- or i-propyl-, n-, i-, s- or t-butyl-substituted phenyl, or together with $R^{17}$ represents one of the radicals —$CH_2$—O—$CH_2$—$CH_2$— and —$CH_2$—$CH_2$—O—$CH_2$—$CH_2$— which are optionally substituted by methyl, ethyl, furyl, phenyl, a fused benzene ring or by two substituents which, together with the C atom to which they are attached, form a 5- or 6-membered carbocycle.

$R^{19}$ preferably represents hydrogen, cyano, fluorine, chlorine, bromine, or represents in each case optionally fluorine-, chlorine- and/or bromine-substituted methyl, ethyl, n- or i-propyl, cyclopropyl, cyclobutyl, cyclopentyl, cyclohexyl or phenyl.

$R^{20}$ preferably represents hydrogen, optionally hydroxyl-, cyano-, fluorine-, chlorine-, methoxy-, ethoxy-, n- or i-propoxy-substituted methyl, ethyl, n- or i-propyl, n-, i-, s- or t-butyl.

$R^{21}$ preferably represents hydrogen, cyano, fluorine, chlorine, bromine, or represents in each case optionally fluorine-, chlorine- and/or bromine-substituted methyl, ethyl, n- or i-propyl, n-, i-, s- or t-butyl, cyclopropyl, cyclobutyl, cyclopentyl, cyclohexyl or phenyl.

$X^1$ preferably represents nitro, cyano, fluorine, chlorine, bromine, methyl, ethyl, n- or i-propyl, n-, i-, s- or t-butyl, difluoromethyl, dichloromethyl, trifluoromethyl, trichloromethyl, chloro-difluoromethyl, fluorodichloromethyl, methoxy, ethoxy, n- or i-propoxy, difluoromethoxy or trifluoromethoxy.

$X^2$ preferably represents hydrogen, nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoromethoxy or trifluoromethoxy.

$X^3$ preferably represents hydrogen, nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoromethoxy or trifluoromethoxy.

t preferably represents the numbers 0, 1, 2, 3 or 4.

v preferably represents the numbers 0, 1, 2 or 3.

$R^{22}$ preferably represents hydrogen, methyl, ethyl, n- or i-propyl.

$R^{23}$ preferably represents hydrogen, methyl, ethyl, n- or i-propyl.

$R^{24}$ preferably represents hydrogen, in each case optionally cyano-, fluorine-, chlorine-, methoxy-, ethoxy-, n- or i-propoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino, or in each case optionally cyano-, fluorine-, chlorine-, bromine-, methyl-, ethyl-, n- or i-propyl-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino or cyclohexylamino.

$R^{25}$ preferably represents hydrogen, in each case optionally cyano-, hydroxyl-, fluorine-, chlorine-, methoxy-, ethoxy-, n- or i-propoxy-substituted methyl, ethyl, n- or i-propyl, n-, i- or s-butyl, in each case optionally cyano-, fluorine-, chlorine- or bromine-substituted propenyl, butenyl, propynyl or butynyl, or in each case optionally cyano-, fluorine-, chlorine-, bromine-, methyl-, ethyl-, n- or i-propyl-substituted cyclopropyl, cyclobutyl, cyclopentyl or cyclohexyl.

$R^{26}$ preferably represents hydrogen, in each case optionally cyano-, hydroxyl-, fluorine-, chlorine-, methoxy-, ethoxy-, n- or i-propoxy-substituted methyl, ethyl, n- or i-propyl, n-, i- or s-butyl, in each case optionally cyano-, fluorine-, chlorine- or bromine-substituted propenyl, butenyl, propynyl or butynyl, in each case optionally cyano-, fluorine-, chlorine-, bromine-, methyl-, ethyl-, n- or i-propyl-substituted cyclopropyl, cyclobutyl, cyclopentyl or cyclohexyl, or optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted phenyl, or together with $R^{25}$ represents in each case optionally methyl- or ethyl-substituted butane-1,4-diyl(trimethylene), pentane-1,5-diyl, 1-oxabutane-1,4-diyl or 3-oxapentane-1,5-diyl.

$X^4$ preferably represents nitro, cyano, carboxyl, carbamoyl, formyl, sulphamoyl, hydroxyl, amino, fluorine, chlorine, bromine, methyl, ethyl, n- or i-propyl, n-, i-, s- or t-butyl, trifluoromethyl, methoxy, ethoxy, n- or i-propoxy, difluoromethoxy or trifluoromethoxy.

$X^5$ preferably represents nitro, cyano, carboxyl, carbamoyl, formyl, sulphamoyl, hydroxyl, amino, fluorine, chlorine, bromine, methyl, ethyl, n- or i-propyl, n-, i-, s- or t-butyl, trifluoromethyl, methoxy, ethoxy, n- or i-propoxy, difluoromethoxy or trifluoromethoxy.

Examples of the compounds of the formula (IIa) which are very particularly preferred as herbicide safeners according to the invention are listed in the table below.

Table: Examples of the Compounds of the Formula (IIa)

| Example No. | (Positions) $(X^1)_m$ | $A^1$ | $R^{14}$ |
|---|---|---|---|
| IIa-1 | (2) Cl, (4) Cl | 1,3-dimethyl-5-methyl-4,5-dihydropyrazol-5-yl with -C(O)OCH₃ | OCH₃ |
| IIa-2 | (2) Cl, (4) Cl | 1,3-dimethyl-5-methyl-4,5-dihydropyrazol-5-yl with -C(O)OC₂H₅ | OCH₃ |
| IIa-3 | (2) Cl, (4) Cl | 1,3-dimethyl-5-methyl-4,5-dihydropyrazol-5-yl with -C(O)OCH₃ | OC₂H₅ |
| IIa-4 | (2) Cl, (4) Cl | 1,3-dimethyl-5-methyl-4,5-dihydropyrazol-5-yl with -C(O)OC₂H₅ | OC₂H₅ |
| IIa-5 | (2) Cl | 1-methyl-3-methyl-5-phenyl-pyrazol-4-yl | OCH₃ |
| IIa-6 | (2) Cl, (4) Cl | 1-methyl-3-methyl-5-phenyl-pyrazol-4-yl | OCH₃ |
| IIa-7 | (2) F | 1-methyl-3-methyl-5-phenyl-pyrazol-4-yl | OCH₃ |
| IIa-8 | (2) F | 1-methyl-3-methyl-5-(2-chlorophenyl)-pyrazol-4-yl | OCH₃ |
| IIa-9 | (2) Cl, (4) Cl | 1-methyl-3-methyl-5-(trichloromethyl)-1,2,4-triazol-4-yl | OC₂H₅ |
| IIa-10 | (2) Cl, (4) CF₃ | 1-methyl-3-methyl-5-phenyl-1,2,4-triazol-4-yl | OCH₃ |
| IIa-11 | (2) Cl | 1-methyl-3-methyl-5-(2-fluorophenyl)-pyrazol-4-yl | OCH₃ |
| IIa-12 | — | 3-methyl-5-methyl-5-phenyl-4,5-dihydroisoxazol-4-yl | OC₂H₅ |
| IIa-13 | (2) Cl, (4) Cl | 1,3-dimethyl-5-methyl-pyrazol-4-yl | OC₂H₅ |
| IIa-14 | (2) Cl, (4) Cl | 1,3-dimethyl-5-(i-C₃H₇)-pyrazol-4-yl | OC₂H₅ |
| IIa-15 | (2) Cl, (4) Cl | 1,3-dimethyl-5-(t-C₄H₉)-pyrazol-4-yl | OC₂H₅ |
| IIa-16 | (2) Cl, (4) Cl | -CH₂- linked 3-methyl-5-methyl-4,5-dihydroisoxazol-5-yl | OC₂H₅ |

-continued (IIa)

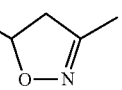

| Example No. | (Positions) $(X^1)_m$ | $A^1$ | $R^{14}$ |
|---|---|---|---|
| IIa-17 | (2) Cl, (4) Cl | 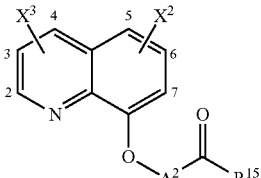 | $OC_2H_5$ |
| IIa-18 | — | 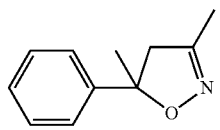 | OH |

Examples of the compounds of the formula (IIb) which are very particularly preferred as herbicide safeners according to the invention are listed in the table below.

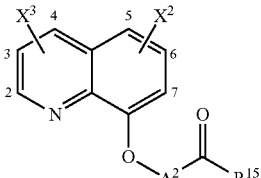

(IIb)

Table: Examples of the Compounds of the Formula (IIb)

| Example No. | (Position) $X^2$ | (Position) $X^3$ | $A^2$ | $R^{15}$ |
|---|---|---|---|---|
| IIb-1 | (5) Cl | — | $CH_2$ | OH |
| IIb-2 | (5) Cl | — | $CH_2$ | $OCH_3$ |
| IIb-3 | (5) Cl | — | $CH_2$ | $OC_2H_5$ |
| IIb-4 | (5) Cl | — | $CH_2$ | $OC_3H_7$-n |
| IIb-5 | (5) Cl | — | $CH_2$ | $OC_3H_7$-i |
| IIb-6 | (5) Cl | — | $CH_2$ | $OC_4H_9$-n |
| IIb-7 | (5) Cl | — | $CH_2$ | $OCH(CH_3)C_5H_{11}$-n |
| IIb-8 | (5) Cl | (2) F | $CH_2$ | OH |
| IIb-9 | (5) Cl | (2) Cl | $CH_2$ | OH |
| IIb-10 | (5) Cl | — | $CH_2$ | $OCH_2CH=CH_2$ |
| IIb-11 | (5) Cl | — | $CH_2$ | $OC_4H_9$-i |
| IIb-12 | (5) Cl | — | $CH_2$ | 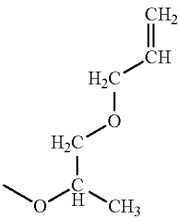 |
| IIb-13 | (5) Cl | — | 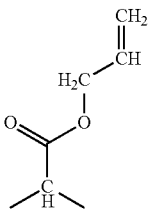 | $OCH_2CH=CH_2$ |
| IIb-14 | (5) Cl | — | 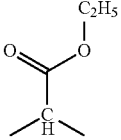 | $OC_2H_5$ |

-continued

| Example No. | (Position) $X^2$ | (Position) $X^3$ | $A^2$ | $R^{15}$ |
|---|---|---|---|---|
| IIb-15 | (5) Cl | — | (CH(CH₃)C(O)O-) | OCH₃ |

Examples of the compounds of the formula (IIc) which are very particularly preferred as herbicide safeners according to the invention are listed in the table below.

$$R^{16}-C(=O)-N(R^{17})(R^{18}) \quad (IIc)$$

Table: Examples of the Compounds of the Formula (IIc)

| Example No. | $R^{16}$ | $N(R^{17}, R^{18})$ |
|---|---|---|
| IIc-1 | CHCl₂ | N(CH₂CH=CH₂)₂ |
| IIc-2 | CHCl₂ | 2,2-dimethyl-3-methyl-oxazolidine |
| IIc-3 | CHCl₂ | 2,2-dimethyl-3-methyl-5-methyl-oxazolidine |
| IIc-4 | CHCl₂ | 1-methyl-1-aza-4-oxa-spiro[4.5]decane |
| IIc-5 | CHCl₂ | 2,2-dimethyl-3-methyl-5-phenyl-oxazolidine |
| IIc-6 | CHCl₂ | 3,4-dimethyl-3,4-dihydro-2H-1,4-benzoxazine |
| IIc-7 | CHCl₂ | 2,2-dimethyl-3-methyl-5-(furan-2-yl)-oxazolidine |

Examples of the compounds of the formula (IId) which are very particularly preferred as herbicide safeners according to the invention are listed in the table below.

(IId)

$$R^{24}-C(=O)-N(R^{23})-Ar(X^5)_v-SO_2-N(R^{22})-C(=O)-Ar(X^4)_t$$

Table: Examples of the Compounds of the Formula (IId)

| Example No. | $R^{22}$ | $R^{23}$ | $R^{24}$ | (Positions) $(X^4)_t$ | (Positions) $(X^5)_v$ |
|---|---|---|---|---|---|
| IId-1 | H | H | CH₃ | (2) OCH₃ | — |
| IId-2 | H | H | C₂H₅ | (2) OCH₃ | — |
| IId-3 | H | H | C₃H₇-n | (2) OCH₃ | — |
| IId-4 | H | H | C₃H₇-i | (2) OCH₃ | — |
| IId-5 | H | H | cyclopropyl | (2) OCH₃ | — |
| IId-6 | H | H | CH₃ | (2) OCH₃ | (5) CH₃ |
| IId-7 | H | H | C₂H₅ | (2) OCH₃ | (5) CH₃ |
| IId-8 | H | H | C₃H₇-n | (2) OCH₃ | (5) CH₃ |
| IId-9 | H | H | C₃H₇-i | (2) OCH₃ | (5) CH₃ |

-continued

| Example No. | $R^{22}$ | $R^{23}$ | $R^{24}$ | (Positions) $(X^4)_t$ | (Positions) $(X^5)_v$ |
|---|---|---|---|---|---|
| IId-10 | H | H | (cyclopropyl) | (2) OCH$_3$ (5) CH$_3$ | — |
| IId-11 | H | H | OCH$_3$ | (2) OCH$_3$ (5) CH$_3$ | — |
| IId-12 | H | H | OC$_2$H$_5$ | (2) OCH$_3$ (5) CH$_3$ | — |
| IId-13 | H | H | OC$_3$H$_7$-i | (2) OCH$_3$ (5) CH$_3$ | — |
| IId-14 | H | H | SCH$_3$ | (2) OCH$_3$ (5) CH$_3$ | — |
| IId-15 | H | H | SC$_2$H$_5$ | (2) OCH$_3$ (5) CH$_3$ | — |
| IId-16 | H | H | SC$_3$H$_7$-i | (2) OCH$_3$ (5) CH$_3$ | — |
| IId-17 | H | H | NHCH$_3$ | (2) OCH$_3$ (5) CH$_3$ | — |
| IId-18 | H | H | NHC$_2$H$_5$ | (2) OCH$_3$ (5) CH$_3$ | — |
| IId-19 | H | H | NHC$_3$H$_7$-i | (2) OCH$_3$ (5) CH$_3$ | — |
| IId-20 | H | H | NH-cyclopropyl | (2) OCH$_3$ (5) CH$_3$ | — |
| IId-21 | H | H | NHCH$_3$ | (2) OCH$_3$ | — |
| IId-22 | H | H | NHC$_3$H$_7$-i | (2) OCH$_3$ | — |
| IId-23 | H | H | N(CH$_3$)$_2$ | (2) OCH$_3$ | — |
| IId-24 | H | H | N(CH$_3$)$_2$ | (3) CH$_3$ (4) CH$_3$ | — |
| IId-25 | H | H | CH$_2$—O—CH$_3$ | (2) OCH$_3$ | — |

Examples of the compounds of the formula (IIe) which are very particularly preferred as herbicide safeners according to the invention are listed in the table below.

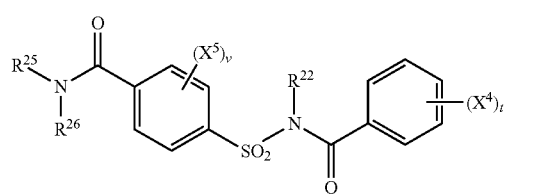

(IIe)

Table: Examples of the Compounds of the Formula (IIe)

| Example No. | $R^{22}$ | $R^{25}$ | $R^{26}$ | (Positions) $(X^4)_t$ | (Positions) $(X^5)_v$ |
|---|---|---|---|---|---|
| IIe-1 | H | H | CH$_3$ | (2) OCH$_3$ | — |
| IIe-2 | H | H | C$_2$H$_5$ | (2) OCH$_3$ | — |
| IIe-3 | H | H | C$_3$H$_7$-n | (2) OCH$_3$ | — |
| IIe-4 | H | H | C$_3$H$_7$-i | (2) OCH$_3$ | — |
| IIe-5 | H | H | (cyclopropyl) | (2) OCH$_3$ | — |
| IIe-6 | H | CH$_3$ | CH$_3$ | (2) OCH$_3$ | — |
| IIe-7 | H | H | CH$_3$ | (2) OCH$_3$ (5) CH$_3$ | — |
| IIe-8 | H | H | C$_2$H$_5$ | (2) OCH$_3$ (5) CH$_3$ | — |
| IIe-9 | H | H | C$_3$H$_7$-n | (2) OCH$_3$ (5) CH$_3$ | — |
| IIe-10 | H | H | C$_3$H$_7$-i | (2) OCH$_3$ (5) CH$_3$ | — |
| IIe-11 | H | H | (cyclopropyl) | (2) OCH$_3$ (5) CH$_3$ | — |
| IIe-12 | H | CH$_3$ | CH$_3$ | (2) OCH$_3$ (5) CH$_3$ | — |

Most preferred as crop plant compatibility-improving compound [component (b')] are cloquintocet-mexyl, fenchlorazole-ethyl, isoxadifen-ethyl, mefenpyr-diethyl, furilazole, fenclorim, cumyluron, dymron, dimepiperate and the compounds IIe-5 and IIe-11, and particular emphasis is given to cloquintocet-mexyl and mefenpyr-diethyl.

The compounds of the general formula (IIa) to be used as safeners according to the invention are known and/or can be prepared by processes known per se (cf. WO-A-91/07874, WO-A-95/07897).

The compounds of the general formula (IIb) to be used as safeners according to the invention are known and/or can be prepared by processes known per se (cf. EP-A-191736).

The compounds of the general formula (IIc) to be used as safeners according to the invention are known and/or can be prepared by processes known per se (cf. DE-A-2218097, DE-A-2350547).

The compounds of the general formula (IId) to be used as safeners according to the invention are known and/or can be prepared by processes known per se (cf. DE-A-19621522/ U.S. Pat. No. 6,235,680).

The compounds of the general formula (IIe) to be used as safeners according to the invention are known and can be prepared by processes known per se (cf. WO-A-99/66795/ U.S. Pat. No. 6,251,827).

Examples of the selective herbicidal combinations according to the invention comprising in each case one active compound of the formula (I) and one of the safeners defined above are listed in the table below.

Table: Examples of Combinations According to the Invention

| Active compounds of the formula (I) | Safener |
|---|---|
| I-a | cloquintocet-mexyl |
| I-a | fenchlorazole-ethyl |
| I-a | isoxadifen-ethyl |
| I-a | mefenpyr-diethyl |
| I-a | furilazole |
| I-a | fenclorim |
| I-a | cumyluron |
| I-a | daimuron/dymron |
| I-a | dimepiperate |
| I-a | IIe-11 |
| I-a | IIe-5 |
| I-b | cloquintocet-mexyl |
| I-b | fenchlorazole-ethyl |
| I-b | isoxadifen-ethyl |
| I-b | mefenpyr-diethyl |

-continued

| Active compounds of the formula (I) | Safener |
|---|---|
| I-b | furilazole |
| I-b | fenclorim |
| I-b | cumyluron |
| I-b | daimuron/dymron |
| I-b | dimepiperate |
| I-b | IIe-11 |
| I-b | IIe-5 |
| I-c | cloquintocet-mexyl |
| I-c | fenchlorazole-ethyl |
| I-c | isoxadifen-ethyl |
| I-c | mefenpyr-diethyl |
| I-c | furilazole |
| I-c | fenclorim |
| I-c | cumyluron |
| I-c | daimuron/dymron |
| I-c | dimepiperate |
| I-c | IIe-5 |
| I-c | IIe-11 |
| I-d | cloquintocet-mexyl |
| I-d | fenchlorazole-ethyl |
| I-d | isoxadifen-ethyl |
| I-d | mefenpyr-diethyl |
| I-d | furilazole |
| I-d | fenclorim |
| I-d | cumyluron |
| I-d | daimuron/dymron |
| I-d | dimepiperate |
| I-d | IIe-11 |
| I-d | IIe-5 |
| I-e | cloquintocet-mexyl |
| I-e | fenchlorazole-ethyl |
| I-e | isoxadifen-ethyl |
| I-e | mefenpyr-diethyl |
| I-e | furilazole |
| I-e | fenclorim |
| I-e | cumyluron |
| I-e | daimuron/dymron |
| I-e | dimepiperate |
| I-e | IIe-5 |
| I-e | IIe-11 |
| I-f | cloquintocet-mexyl |
| I-f | fenchlorazole-ethyl |
| I-f | isoxadifen-ethyl |
| I-f | mefenpyr-diethyl |
| I-f | furilazole |
| I-f | fenclorim |
| I-f | cumyluron |
| I-f | daimuron/dymron |
| I-f | dimepiperate |
| I-f | IIe-5 |
| I-f | IIe-11 |
| I-g | cloquintocet-mexyl |
| I-g | fenchlorazole-ethyl |
| I-g | isoxadifen-ethyl |
| I-g | mefenpyr-diethyl |
| I-g | furilazole |
| I-g | fenclorim |
| I-g | cumyluron |
| I-g | daimuron/dymron |
| I-g | dimepiperate |
| I-g | IIe-5 |
| I-g | IIe-11 |
| I-h | cloquintocet-mexyl |
| I-h | fenchlorazole-ethyl |
| I-h | isoxadifen-ethyl |
| I-h | mefenpyr-diethyl |
| I-h | furilazole |
| I-h | fenclorim |
| I-h | cumyluron |
| I-h | daimuron/dymron |
| I-h | dimepiperate |
| I-h | IIe-5 |
| I-h | IIe-11 |

Surprisingly, it has now been found that the active compound combinations, defined above, of trifluoromethoxyphenyl-substituted tetramic acid derivatives of the general formula (I) and safeners (antidotes) from group (b') listed above, while being very well tolerated by useful plants, have a particularly high herbicidal activity and can be used in various crops, in particular in cereals (especially wheat), but also in soya beans, potatoes, maize and rice, for the selective control of weeds.

Here, it has to be considered surprising that, from a large number of known safeners or antidotes capable of antagonizing the harmful effect of a herbicide on crop plants, those suitable are in particular the compounds of group (b') listed above which eliminate the harmful effect of substituted tetramic acid derivatives on the crop plants virtually completely without having a major adverse effect on the herbicidal activity against the weeds.

Emphasis may be given here to the particularly advantageous effect of the particularly and most preferred combination partners from group (b'), in particular with respect to sparing cereal plants, such as, for example, wheat, barley and rye, but also maize and rice, as crop plants.

In the literature it has already been described how the action of various active compounds can be boosted by addition of ammonium salts. The salts in question, however, are detersive salts (for example WO 95/017817) or salts which have relatively long alkyl substituents and/or aryl substituents and which have a permeabilizing action or which increase the active compound's solubility (for example EP-A 0 453 086, EP-A 0 664 081, FR-A 2 600 494, U.S. Pat. No. 4,844,734, U.S. Pat. No. 5,462,912, U.S. Pat. No. 5,538,937, U.S. Ser. No. 03/0224939, U.S. Ser. No. 05/0009880, U.S. Ser. No. 05/0096386). Moreover, the prior art describes the action only for particular active compounds and/or particular applications of the corresponding compositions. In other cases, in turn, the salts in question are those of sulphonic acids, where the acids themselves have a paralytic action on insects (U.S. Pat. No. 2,842,476). A boost to action by ammonium sulphate, for example, is described by way of example for the herbicides glyphosate, phosphinothricin and certain cyclic ketoenols (U.S. Pat. No. 6,645,914, EP-A2 0 036 106, WO 07/068,427). A corresponding action in the case of insecticides is described for certain cyclic ketoenols in WO 07/068,428.

The use of ammonium sulphate as a formulating assistant has also been described for certain active compounds and applications (WO 92/16108), but its purpose therein is to stabilize the formulation, not to boost the action.

It has now been found, surprisingly, that the action of insecticides and/or acaricides and/or herbicides from the class of the trifluoromethoxyphenyl-substituted tetramic acid derivatives of the formula (I) can be boosted significantly through the addition of ammonium salts or phosphonium salts to the application solution or through the incorporation of these salts into a formulation comprising trifluoromethoxyphenyl-substituted tetramic acid derivatives of the formula (I). The present invention therefore provides for the use of ammonium salts or phosphonium salts for boosting the action of crop protection compositions which comprise as their active compound herbicidal and/or insecticidal and/or acaricidal trifluoromethoxyphenyl-substituted tetramic acid derivatives of the formula (I). The invention likewise provides compositions which comprise herbicidal and/or acaricidal and/or insecticidal trifluoromethoxyphenyl-substituted tetramic acid derivatives of the formula (I) and action-boosting ammonium salts or phosphonium salts, including not only formulated active compounds but also ready-to-use compositions (spray liquors). The invention further provides, finally, for the use of these compositions for controlling insect pests and/or spider mites and/or unwanted plant growth.

The compounds of the formula (I) possess a broad insecticidal and/or acaricidal and/or herbicidal activity, but in specific cases the activity and/or plant tolerance leaves something to be desired. However, some or all of these properties can be improved by adding ammonium salts or phosphonium salts.

The active compounds can be used in the compositions according to the invention in a broad concentration range. The concentration of the active compounds in the formulation is typically 0.1%-50% by weight.

The formula (III') provides a definition of the ammonium salts and phosphonium salts which, according to the invention, boost the activity of crop protection compositions comprising an active compound from the class of the trifluoromethoxyphenyl-substituted tetramic acid derivatives of the formula (I)

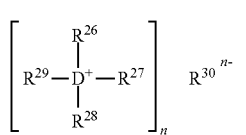

(III')

in which

D represents nitrogen or phosphorus,

D preferably represents nitrogen, $R^{26}$, $R^{27}$, $R^{28}$ and $R^{29}$ independently of one another represent hydrogen or in each case optionally substituted $C_1$-$C_8$-alkyl or mono- or polyunsaturated, optionally substituted $C_1$-$C_8$-alkylene, the substituents being selectable from halogen, nitro and cyano, $R^{26}$, $R^{27}$, $R^{28}$ and $R^{29}$ independently of one another preferably represent hydrogen or in each case optionally substituted $C_1$-$C_4$-alkyl, the substituents being selectable from halogen, nitro and cyano, $R^{26}$, $R^{27}$, $R^{28}$ and $R^{29}$ independently of one another particularly preferably represent hydrogen, methyl, ethyl, n-propyl, isopropyl, n-butyl, isobutyl, sec-butyl or tert-butyl, $R^{26}$, $R^{27}$, $R^{28}$ and $R^{29}$ very particularly preferably represent hydrogen, n represents 1, 2, 3 or 4, n preferably represents 1 or 2, $R^{30}$ represents an organic or inorganic anion, $R^{30}$ preferably represents hydrogencarbonate, tetraborate, fluoride, bromide, iodide, chloride, monohydrogenphosphate, dihydrogenphosphate, hydrogensulphate, tartrate, sulphate, nitrate, thiosulphate, thiocyanate, formate, lactate, acetate, propionate, butyrate, pentanoate or oxalate, $R^{30}$ particularly preferably represents lactate, sulphate, nitrate, thiosulphate, thiocyanate, oxalate or formate.

$R^{30}$ very particularly preferably represents sulphate.

Inventively emphasized combinations of active compound, salt and penetrant are listed in the table below. "Penetrant as per test" means here that any compound that acts as a penetrant in the cuticle penetration test (Baur et al., 1997, Pesticide Science 51, 131-152) is suitable.

The ammonium salts and phosphonium salts of the formula (III') can be used in a broad concentration range to boost the activity of crop protection compositions comprising trifluoromethoxyphenyl-substituted tetramic acid derivatives of the formula (I). In general the ammonium salts or phosphonium salts are used in the ready-to-use crop protection composition in a concentration of 0.5 to 80 mmol/l, preferably 0.75 to 37.5 mmol/l, more preferably 1.5 to 25 mmol/l. In the case of a formulated product the ammonium salt and/or phosphonium salt concentration in the formulation is chosen such that it is within these stated general, preferred or particularly preferred ranges after the formulation has been diluted to the desired active compound concentration. The concentration of the salt in the formulation is typically 1%-50% by weight.

In one preferred embodiment of the invention the activity is boosted by adding to the crop protection compositions not only an ammonium salt and/or phosphonium salt but also, additionally, a penetrant. It is considered entirely surprising that even in these cases an even greater boost to activity is observed. The present invention therefore likewise provides for the use of a combination of penetrant and ammonium salts and/or phosphonium salts to boost the activity of crop protection compositions which comprise insecticidal trifluoromethoxyphenyl-substituted tetramic acid derivatives of the formula (I) as active compound. The invention likewise provides compositions which comprise herbicidal and/or acaricidal and/or insecticidal trifluoromethoxyphenyl-substituted tetramic acid derivatives of the formula (I), penetrants and ammonium salts and/or phosphonium salts, including specifically not only formulated active compounds but also ready-to-use compositions (spray liquors). The invention additionally provides, finally, for the use of these compositions for controlling harmful insects and/or spider mites.

In the present context, suitable penetrants are all those substances which are usually employed to improve penetration of agrochemically active compounds into plants. In this context, penetrants are defined in that they penetrate from the aqueous spray liquor and/or the spray coating into the cuticles of the plant, thus increasing the mobility of active compounds in the cuticles. The method described in the literature (Baur et al., 1997, Pesticide Science 51, 131-152) can be used for determining this property.

Examples of suitable penetrants include alkanol alkoxylates. Penetrants of the invention are alkanol alkoxylates of the formula (IV')

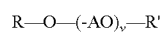

(IV')

in which

R is linear or branched alkyl having 4 to 20 carbon atoms,

R' is hydrogen, methyl, ethyl, n-propyl, isopropyl, n-butyl, isobutyl, tert-butyl, n-pentyl or n-hexyl, AO is an ethylene oxide radical, a propylene oxide radical, a butylene oxide radical or is mixtures of ethylene oxide and propylene oxide radicals or butylene oxide radicals, and v is a number from 2 to 30.

One preferred group of penetrants are alkanol alkoxylates of the formula

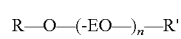

(IV'-a)

in which

R is as defined above,

R' is as defined above,

EO is —$CH_2$—$CH_2$—O—, and n is a number from 2 to 20.

A further preferred group of penetrants are alkanol alkoxylates of the formula

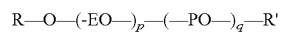

(IV'-b)

in which
R is as defined above,
R' is as defined above,
EO is —CH$_2$—CH$_2$—O—,
PO is

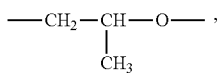

p is a number from 1 to 10, and
q is a number from 1 to 10.

A further preferred group of penetrants are alkanol alkoxylates of the formula

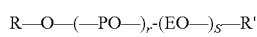 (IV'-c)

in which
R is as defined above,
R' is as defined above,
EO is —CH$_2$—CH$_2$—O—,
PO is

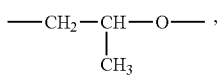

r is a number from 1 to 10, and
s is a number from 1 to 10.

A further preferred group of penetrants are alkanol alkoxylates of the formula

R—O—(-EO-)$_p$—(-EO—)$_q$—R' (IV'-d)

in which
R and R' are as defined above,
EO is CH$_2$—CH$_2$—O—,
BO is

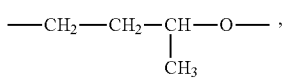

p is a number from 1 to 10 and
q is a number from 1 to 10.

A further preferred group of penetrants are alkanol alkoxylates of the formula

R—O—(—BO—)$_r$—(-EO—)$_s$—R' (IV'-e)

in which
R and R' are as defined above,
BO is

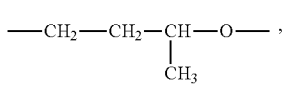

EO is CH$_2$—CH$_2$—O—,
r is a number from 1 to 10 and
s is a number from 1 to 10.

A further preferred group of penetrants are alkanol alkoxylates of the formula

CH$_3$—(CH$_2$)$_t$—CH$_2$—O—(—CH$_2$—CH$_2$—O—)$_u$—R' (IV'-f)

in which
R' is as defined above,
t is a number from 8 to 13,
u is a number from 6 to 17.

In the formulae indicated above,
R is preferably butyl, isobutyl, n-pentyl, isopentyl, neopentyl, n-hexyl, isohexyl, n-octyl, isooctyl, 2-ethylhexyl, nonyl, isononyl, decyl, n-dodecyl, isododecyl, lauryl, myristyl, isotridecyl, trimethylnonyl, palmityl, stearyl or eicosyl.

As an example of an alkanol alkoxylate of the formula (IV'-c) mention may be made of 2-ethylhexyl alkoxylate of the formula

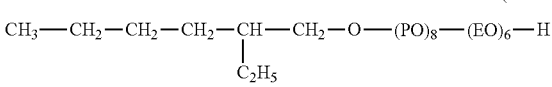 (IV'-c-1)

in which
EO is —CH$_2$—CH$_2$—O—,
PO is

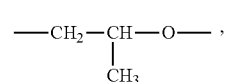

and
the numbers 8 and 6 represent average values.

As an example of an alkanol alkoxylate of the formula (IV'-d) mention may be made of the formula CH$_3$—(CH$_2$)$_{10}$—O—(-EO—)$_6$—(—BO—)$_2$—CH$_3$ (IV'-d-1)

in which
EO is CH$_2$—CH$_2$—O—,
BO is

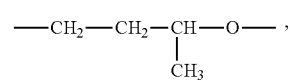

and
the numbers 10, 6 and 2 represent average values.

Particularly preferred alkanol alkoxylates of the formula (IV'-f) are compounds of this formula in which
t is a number from 9 to 12 and
u is a number from 7 to 9.

Mention may be made with very particular preference of alkanol alkoxylate of the formula (IV'-f-1)

CH$_3$—(CH$_2$)$_t$—CH$_2$—O—(—CH$_2$—CH$_2$—O—)$_u$—H (IV'-f-1)

in which
t stands for the average value 10.5 and
u stands for the average value 8.4.

A general definition of the alkanol alkoxylates is given by the formulae above. These substances are mixtures of compounds of the stated type with different chain lengths. The indices therefore have average values which may also deviate from whole numbers.

The alkanol alkoxylates of the formulae stated are known and in some cases are available commercially or can be prepared by known methods (cf. WO 98/35 553, WO 00/35 278 and EP-A 0 681 865).

Suitable penetrants also include, for example, substances which promote the availability of the compounds of the formula (I) in the spray coating. These include, for example, mineral or vegetable oils. Suitable oils are all mineral or vegetable oils—modified or otherwise—which can typically be used in agrochemical compositions. Mention may be made by way of example of sunflower oil, rapeseed oil, olive oil, castor oil, colza oil, maize seed oil, cotton seed oil and soya bean oil, or the esters of said oils. Preference is given to rapeseed oil, sunflower oil and their methyl or ethyl esters.

The concentration of penetrant in the compositions of the invention can be varied within a wide range. In the case of a formulated crop protection composition it is in general 1% to 95%, preferably 1% to 55%, more preferably 15%-40% by weight. In the ready-to-use compositions (spray liquors) the concentrations are generally between 0.1 and 10 g/l, preferably between 0.5 and 5 g/l.

Crop protection compositions of the invention may also comprise further components, examples being surfactants and/or dispersing assistants or emulsifiers.

Suitable nonionic surfactants and/or dispersing assistants include all substances of this type that can typically be used in agrochemical compositions. Preferably mention may be made of polyethylene oxide-polypropylene oxide block copolymers, polyethylene glycol ethers of linear alcohols, reaction products of fatty acids with ethylene oxide and/or propylene oxide, and also polyvinyl alcohol, polyvinylpyrrolidone, copolymers of polyvinyl alcohol and polyvinylpyrrolidone, and copolymers of (meth)acrylic acid and (meth) acrylic esters, and additionally alkyl ethoxylates and alkylaryl ethoxylates, which optionally may be phosphated and optionally may be neutralized with bases, mention being made, by way of example, of sorbitol ethoxylates, and, as well, polyoxyalkylenamine derivatives.

Suitable anionic surfactants include all substances of this type that can typically be used in agrochemical compositions. Preference is given to alkali metal salts and alkaline earth metal salts of alkylsulphonic acids or alkylarylsulphonic acids.

A further preferred group of anionic surfactants and/or dispersing assistants are the following salts that are of low solubility in plant oil: salts of polystyrenesulphonic acids, salts of polyvinylsulphonic acids, salts of naphthalenesulphonic acid-formaldehyde condensation products, salts of condensation products of naphthalenesulphonic acid, phenolsulphonic acid and formaldehyde, and salts of lignosulphonic acid.

Suitable additives which may be included in the formulations of the invention are emulsifiers, foam inhibitors, preservatives, antioxidants, colorants and inert filling materials.

Preferred emulsifiers are ethoxylated nonylphenols, reaction products of alkylphenols with ethylene oxide and/or propylene oxide, ethoxylated arylalkylphenols, and also ethoxylated and propoxylated arylalkylphenols, and also sulphated or phosphated arylalkyl ethoxylates and/or arylalkyl ethoxypropoxylates, mention being made by way of example of sorbitan derivatives, such as polyethylene oxide-sorbitan fatty acid esters, and sorbitan fatty acid esters.

Using, for example, according to process (A) ethyl N-(2, 6-dichloro-4-trifluoromethoxyphenyl-acetyl)-1-aminocyclohexanecarboxylate as starting material, the course of the process according to the invention can be represented by the reaction scheme below:

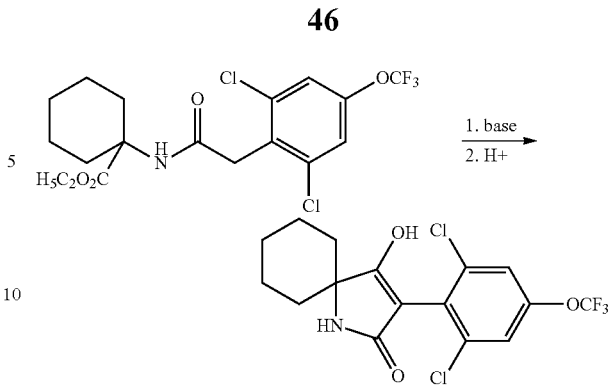

Using, for example, according to process (Bα) 3-(2-chloro-4-trifluoromethoxy-6-methoxyphenyl)-5,5-dimethylpyrrolidine-2,4-dione and pivaloyl chloride as starting materials, the course of the process according to the invention can be represented by the reaction scheme below:

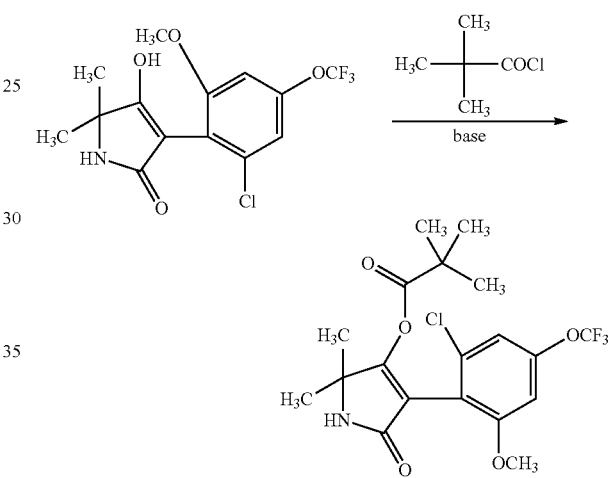

Using, for example, according to process (Bβ) 3-(2,6-dibromo-4-trifluoromethoxyphenyl)-5,5-dimethylpyrrolidine-2,4-dione and acetic anhydride as starting materials, the course of the process according to the invention can be represented by the reaction scheme below:

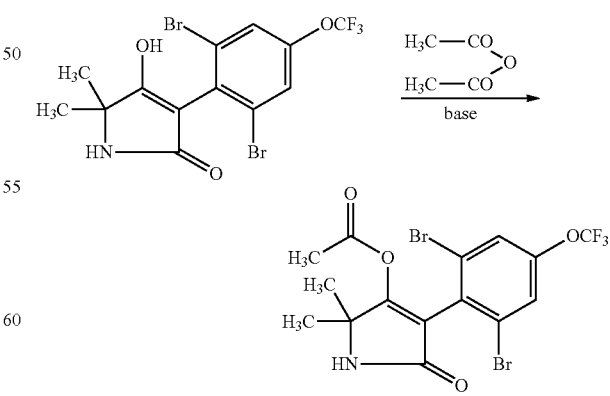

Using, for example, according to process (C) 8-[(2,6-dichloro-4-trifluoromethoxy)phenyl]-1-aza-bicyclo-(4,3,0$^{1,}$ $_6$)-nonane-7,9-dione and ethyl chloroformate as starting materials, the course of the process according to the invention can be represented by the reaction scheme below:

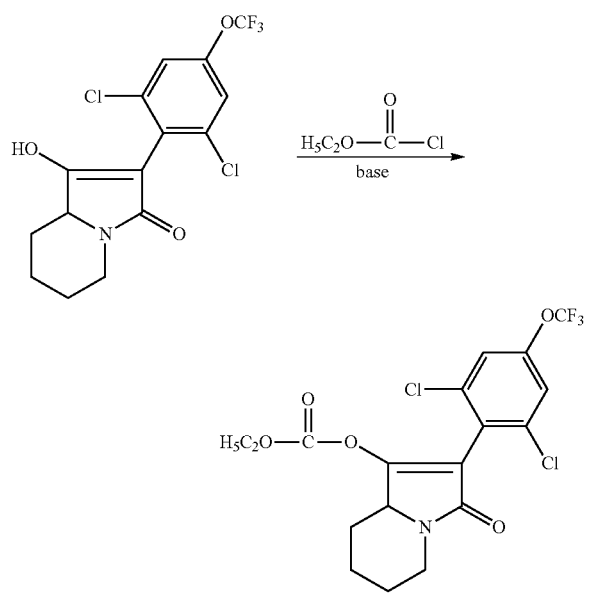

Using, for example, according to process (D) 3-(2,6-dibromo-4-trifluoromethoxyphenyl)-5,5-dimethyl-6-pyrrolidine-2,4-dione and methyl chloromonothioformate as starting materials, the course of the reaction can be represented as follows:

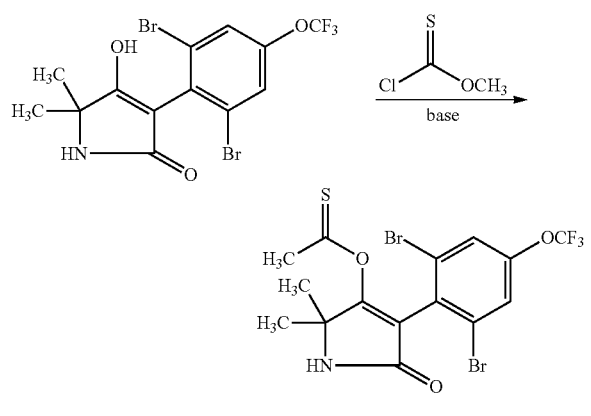

Using, for example, according to process (E) 3-(2,6-dichloro-4-trifluoromethoxyphenyl)-5,5-pentamethylenepyrrolidine-2,4-dione and methanesulphonyl chloride as starting material, the course of the reaction can be represented by the reaction scheme below:

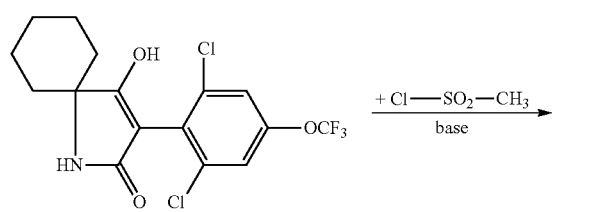

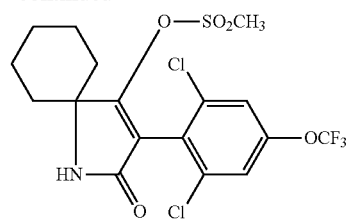

Using, for example, according to process (F) 3-(2-trifluoromethoxyphenyl)-5,5-dimethylpyrrolidine-2,4-dione and 2,2,2-trifluoroethyl methanethiophosphonyl chloride as starting materials, the course of the reaction can be represented by the reaction scheme below:

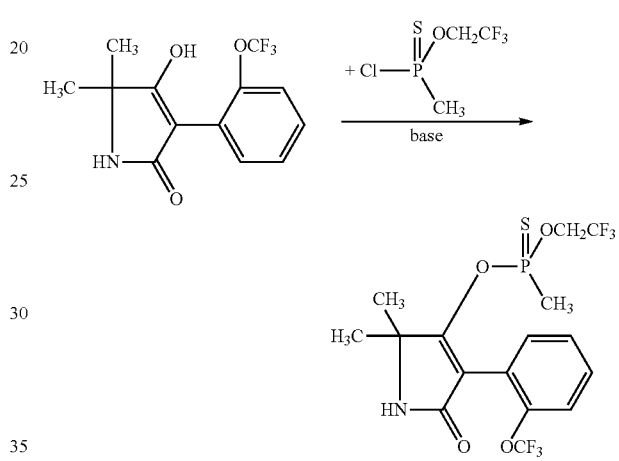

Using, for example, according to process (G) 3-(2-chloro-4-trifluoromethoxy-6-methoxyphenyl]-5-cyclopropyl-5-methylpyrrolidine-2,4-dione and NaOH as components, the course of the process according to the invention can be represented by the reaction scheme below:

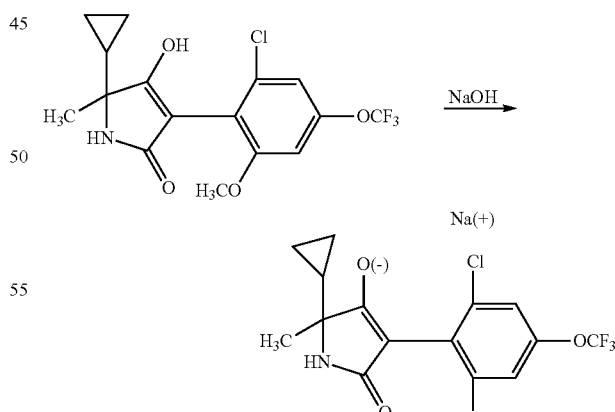

Using, for example, according to process (H) variant α 3-(2,6-dibromo-4-trifluoromethoxyphenyl)-5,5-tetramethylenepyrrolidine-2,4-dione and ethyl isocyanate as starting materials, the course of the reaction can be represented by the reaction scheme below:

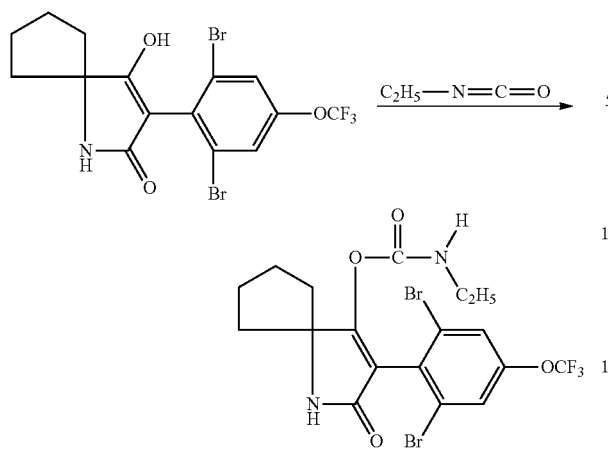

(XIII)

in which

A, B, $R^8$ and D have the meanings given above, are acylated with substituted phenylacetic acid derivatives of the formula (XIV)

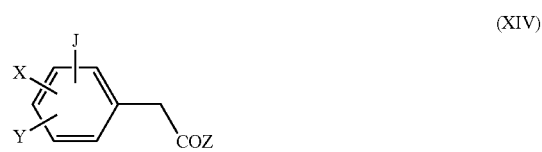

(XIV)

in which

J, X and Y have the meanings given above and

Z represents a leaving group introduced by reagents for activating carboxylic acids, such as carbonyldiimidazole, carbonyldiimides (such as, for example, dicyclohexylcarbodiimide), phosphorylating reagents (such as, for example, $POCl_3$, BOP—Cl), halogenating agents, such as, for example, thionyl chloride, oxalyl chloride, phosgene or chloroformic esters, (Chem. Reviews 52, 237-416 (1953); Bhattacharya, Indian J. Chem. 6, 341-5, 1968)

or when acylamino acids of the formula (XV)

Using, for example, according to process (H) variant β 3-(2,6-dichloro-4-trifluoromethoxyphenyl)-5,5-dimethylpyrrolidine-2,4-dione and dimethylcarbamoyl chloride as starting materials, the course of the reaction can be represented by the scheme below:

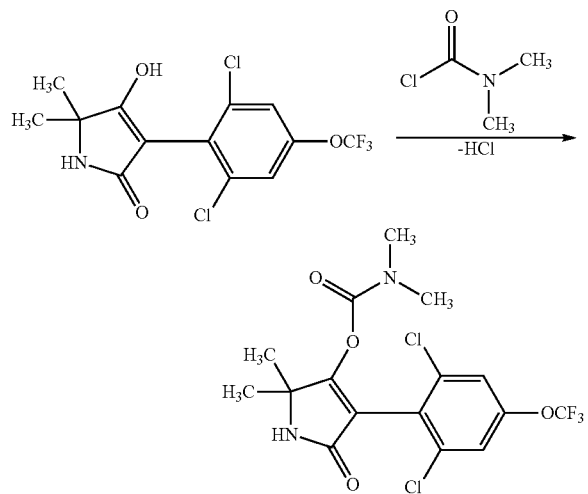

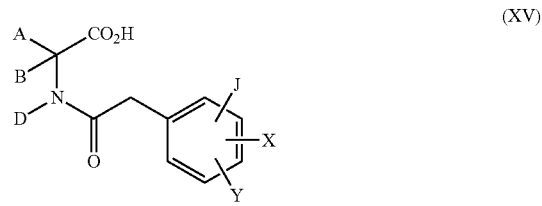

(XV)

in which

A, B, D, J, X and Y have the meanings given above, are esterified (Chem. Ind. (London) 1568 (1968)).

The compounds of the formula (XV)

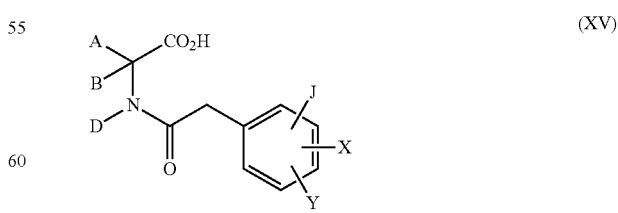

(XV)

in which

A, B, D, J, X and Y have the meanings given above, are novel.

The compounds, required as starting materials in the process (A) according to the invention, of the formula (II)

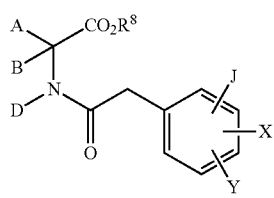

(II)

in which

A, B, D, J, X, Y and $R^8$ have the meanings given above, are novel.

The acylamino acid esters of the formula (II) are obtained, for example, when amino acid derivatives of the formula (XIII)

The compounds of the formula (XV) are obtained when amino acids of the formula (XVI)

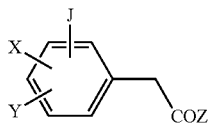
(XVI)

in which
A, B and D have the meanings given above,
are acylated, for example, according to Schotten-Baumann (Organikum, VEB Deutscher Verlag der Wissenschaften, Berlin 1977, p. 505) with substituted phenylacetic acid derivatives of the formula (XIV)

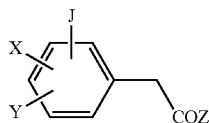
(XIV)

in which
J, X and Y have the meanings given above and
Z has the meaning given above.

The compounds of the formula (XIV) are novel. They can be obtained by methods known in principle and as shown in the examples (see, for example, H. Henecka, Houben-Weyl, Methoden der Organischen Chemie, Vol. 8, pp. 467-469 (1952)).

The compounds of the formula (XIV) are obtained, for example, when substituted phenylacetic acids of the formula (XVII)

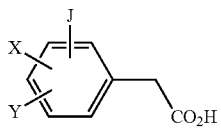
(XVII)

in which
J, X and Y have the meaning given above,
are reacted with halogenating agents (for example thionyl chloride, thionyl bromide, oxalyl chloride, phosgene, phosphorus trichloride, phosphorus tribromide or phosphorus pentachloride), phosphonylating agents (such as, for example, $POCl_3$, BOP—Cl), carbonyldiimidazole, carbonyldiimides (for example dicyclohexylcarbonyldiimide), optionally in the presence of a diluent (for example optionally chlorinated aliphatic or aromatic hydrocarbons such as toluene or methylene chloride or ethers, for example tetrahydrofuran, dioxane, methyl tert-butyl ether), at temperatures of from −20° C. to 150° C., preferably from −10° C. to 100° C.

Some of the compounds of the formula (XVII) are commercially available. Novel compounds of the formula (XVII) are described in the experimental part or can be prepared by processes known from the applications cited at the outset.

Some of the compounds of the formula (XIII) and (XVI) are known, and/or can be prepared by known processes (see, for example, Compagnon, Miocque Ann. Chim. (Paris) [14] 5, pp. 11-22, 23-27 (1970)).

The substituted cyclic aminocarboxylic acids of the formula (XVI) in which A and B form a ring can generally be obtained by the Bucherer-Bergs synthesis or by the Strecker synthesis, where they are in each case obtained in different isomeric forms. Thus, the conditions of the Bucherer-Bergs synthesis yield predominantly the isomers (hereinbelow, for the sake of simplicity, referred to as β) in which the radicals R and the carboxyl group are in equatorial positions, whereas the conditions of the Strecker synthesis yield predominantly the isomers (hereinbelow, for the sake of simplicity, referred to as α) in which the amino group and the radicals R are in equatorial positions.

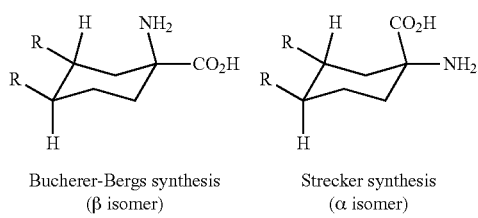

Bucherer-Bergs synthesis (β isomer)    Strecker synthesis (α isomer)

(L. Munday, J. Chem. Soc. 4372 (1961); J. T. Eward, C. Jitrangeri, Can. J. Chem. 53, 3339 (1975)).

Furthermore, the starting materials, employed in the above process (A), of the formula (II)

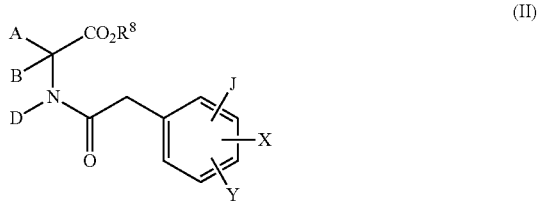
(II)

in which
A, B, D, J, X, Y and $R^8$ have the meanings given above,
can be prepared by reacting aminonitriles of the formula (XVIII)

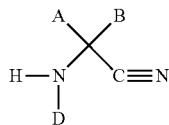
(XVIII)

in which
A, B and D have the meanings given above,
with substituted phenylacetic acid derivatives of the formula (XIV)

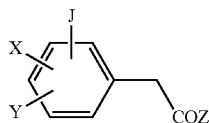
(XIV)

in which
J, X, Y and Z have the meanings given above, to give compounds of the formula (XIX)

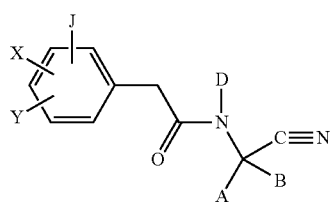

(XIX)

in which
A, B, D, J, X and Y have the meanings given above,
and then subjecting these to an acidic alcoholysis.

The compounds of the formula (XIX) are likewise novel.

The acid halides of the formula (III), carboxylic anhydrides of the formula (IV), chloroformic esters or chloroformic thioesters of the formula (V), chloromonothioformic esters or chlorodithioformic esters of the formula (VI), sulphonyl chlorides of the formula (VII), phosphorus compounds of the formula (VIII) and metal hydroxides, metal alkoxides or amines of the formulae (IX) and (X), respectively, and isocyanates of the formula (XI) and carbamoyl chlorides of the formula (XII) furthermore required as starting materials for carrying out the processes (B), (C), (D), (E), (F), (G) and (H) according to the invention are generally known compounds of organic or inorganic chemistry.

In addition, the compounds of the formulae (XIII), (XVI) and (XVIII) are known from the patent applications cited at the outset and/or can be prepared by the methods given therein.

The process (A) is characterized in that compounds of the formula (II) in which A, B, D, J, X, Y and $R^8$ have the meanings given above are subjected to an intramolecular condensation in the presence of a base.

Suitable diluents for use in the process (A) according to the invention are all inert organic solvents. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methylpyrrolidone, and also alcohols, such as methanol, ethanol, propanol, isopropanol, butanol, isobutanol and tert-butanol.

Suitable bases (deprotonating agents) for carrying out the process (A) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which may also be used in the presence of phase-transfer catalysts, such as, for example, triethylbenzylammonium chloride, tetrabutylammonium bromide, Adogen 464 (=methyltrialkyl($C_8$-$C_{10}$)ammonium chloride) or TDA 1 (=tris(methoxyethoxyethyl)amine). It is furthermore possible to use alkali metals, such as sodium or potassium. Further, it is possible to employ alkali metal and alkaline earth metal amides and hydrides, such as sodium amide, sodium hydride and calcium hydride, and additionally also alkali metal alkoxides, such as sodium methoxide, sodium ethoxide and potassium tert-butoxide.

When carrying out the process (A) according to the invention, the reaction temperatures may be varied within a relatively wide range. In general, the process is carried out at temperatures between 0° C. and 250° C., preferably between 50° C. and 150° C.

The process (A) according to the invention is generally carried out under atmospheric pressure.

When carrying out the process (A) according to the invention, the reaction components of the formula (II) and the deprotonating bases are generally employed in about doubly equimolar amounts. However, it is also possible to use a relatively large excess (up to 3 mol) of one component or the other.

The process (B-α) is characterized in that compounds of the formula (I-a) are reacted with carbonyl halides of the formula (III), if appropriate in the presence of a diluent and if appropriate in the presence of an acid binder.

Suitable diluents for use in the process (B-α) according to the invention are all solvents inert towards the acid halides. Preference is given to using hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethyl sulphoxide and sulpholane. If the acid halide is sufficiently stable to hydrolysis, the reaction can also be carried out in the presence of water.

Suitable acid binders for the reaction according to the process (B-α) according to the invention are all customary acid acceptors. Preference is given to using tertiary amines, such as triethylamine, pyridine, diazabicyclooctane (DABCO), diazabicycloundecene (DBU), diazabicyclononene (DBN), Hünig base and N,N-dimethylaniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

The reaction temperatures in the process (B-α) according to the invention can be varied within a relatively wide range. In general, the process is carried out at temperatures between −20° C. and +150° C., preferably between 0° C. and 100° C.

When carrying out the process (B-α) according to the invention, the starting materials of the formula (I-a) and the carbonyl halide of the formula (III) are generally each employed in approximately equivalent amounts. However, it is also possible to use a relatively large excess (up to 5 mol) of the carbonyl halide. Work-up is carried out by customary methods.

The process (B-β) is characterized in that compounds of the formula (I-a) are reacted with carboxylic anhydrides of the formula (IV), if appropriate in the presence of a diluent and if appropriate in the presence of an acid binder.

Suitable diluents for use in the process (B-β) according to the invention are, preferably, the diluents which are also preferred when using acid halides. Besides, excess carboxylic anhydride may simultaneously act as diluent.

Suitable acid binders, which are added, if appropriate, for process (B-β) are, preferably, the acid binders which are also preferred when using acid halides.

The reaction temperatures in the process (B-β) according to the invention may be varied within a relatively wide range. In general, the process is carried out at temperatures between −20° C. and +150° C., preferably between 0° C. and 100° C.

When carrying out the process (B-β) according to the invention, the starting materials of the formula (I-a) and the carboxylic anhydride of the formula (IV) are generally each employed in approximately equivalent amounts. However, it is also possible to use a relatively large excess (up to 5 mol) of carboxylic anhydride. Work-up is carried out by customary methods.

In general, diluent and excess carboxylic anhydride and the carboxylic acid formed are removed by distillation or by washing with an organic solvent or with water.

The process (C) is characterized in that compounds of the formula (I-a) are reacted with chloroformic esters or chloroformic thioesters of the formula (V), if appropriate in the presence of a diluent and if appropriate in the presence of an acid binder.

Suitable acid binders for the reaction according to the process (C) according to the invention are all customary acid acceptors. Preference is given to using tertiary amines, such as triethylamine, pyridine, DABCO, DBU, DBA, Hünig base and N,N-dimethylaniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

Suitable diluents for use in the process (C) according to the invention are all solvents which are inert towards the chloroformic esters or chloroformic thioesters. Preference is given to using hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethyl sulphoxide and sulpholane.

When carrying out the process (C) according to the invention, the reaction temperatures can be varied within a relatively wide range. If the process is carried out in the presence of a diluent and an acid binder, the reaction temperatures are generally between −20° C. and +100° C., preferably between 0° C. and 50° C.

The process (C) according to the invention is generally carried out under atmospheric pressure.

When carrying out the process (C) according to the invention, the starting materials of the formula (I-a) and the appropriate chloroformic ester or chloroformic thioester of the formula (V) are generally each employed in approximately equivalent amounts. However, it is also possible to use a relatively large excess (up to 2 mol) of one component or the other. Work-up is carried out by customary methods. In general, precipitated salts are removed and the reaction mixture that remains is concentrated by removing the diluent under reduced pressure.

The process (D) according to the invention is characterized in that compounds of the formula (I-a) are reacted with compounds of the formula (VI) in the presence of a diluent and, if appropriate, in the presence of an acid binder.

In preparation process (D), about 1 mol of chloromonothioformic ester or chlorodithioformic ester of the formula (VI) is employed per mole of the starting material of the formula (I-a) at from 0 to 120° C., preferably from 20 to 60° C.

Suitable diluents which are added, if appropriate, are all inert polar organic solvents, such as ethers, amides, sulphones, sulphoxides, and also halogenated alkanes.

Preference is given to using dimethyl sulphoxide, tetrahydrofuran, dimethylformamide or methylene chloride.

If, in a preferred embodiment, the enolate salt of the compounds (I-a) is prepared by addition of strong deprotonating agents, such as, for example, sodium hydride or potassium tert-butoxide, the further addition of acid binders may be dispensed with.

If acid binders are used, these are customary inorganic or organic bases; sodium hydroxide, sodium carbonate, potassium carbonate, pyridine and triethylamine may be mentioned by way of example.

The reaction may be carried out at atmospheric pressure or under elevated pressure and is preferably carried out at atmospheric pressure. Work-up is carried out by customary methods.

The process (E) according to the invention is characterized in that compounds of the formula (I-a) are reacted with sulphonyl chlorides of the formula (VII), if appropriate in the presence of a diluent and if appropriate in the presence of an acid binder.

In preparation process (E), about 1 mol of sulphonyl chloride of the formula (VII) is reacted per mole of the starting material of the formula (I-a) at from −20 to 150° C., preferably from 20 to 70° C.

Suitable diluents which are added, if appropriate, are all inert polar organic solvents, such as ethers, amides, nitriles, sulphones, sulphoxides or halogenated hydrocarbons, such as methylene chloride.

Preference is given to using dimethyl sulphoxide, tetrahydrofuran, dimethylformamide, methylene chloride.

If, in a preferred embodiment, the enolate salt of the compounds (I-a) is prepared by addition of strong deprotonating agents (such as, for example, sodium hydride or potassium tert-butoxide), the further addition of acid binders may be dispensed with.

If acid binders are used, these are customary inorganic or organic bases, for example sodium hydroxide, sodium carbonate, potassium carbonate, pyridine and triethylamine.

The reaction may be carried out at atmospheric pressure or under elevated pressure and is preferably carried out at atmospheric pressure. Work-up is carried out by customary methods.

The process (F) according to the invention is characterized in that compounds of the formula (I-a) are reacted with phosphorus compounds of the formula (VIII), if appropriate in the presence of a diluent and if appropriate in the presence of an acid binder.

In preparation process (F), to obtain compounds of the formula (I-e), from 1 to 2, preferably from 1 to 1.3, mol of the phosphorus compound of the formula (VIII) are reacted per mole of the compounds (I-a), at temperatures between −40° C. and 150° C., preferably between −10 and 110° C.

Suitable diluents which are added, if appropriate, are all inert polar organic solvents, such as ethers, amides, nitriles, alcohols, sulphides, sulphones, sulphoxides, etc.

Preference is given to using acetonitrile, dimethyl sulphoxide, tetrahydrofuran, dimethylformamide, methylene chloride.

Suitable acid binders which are added, if appropriate, are customary inorganic or organic bases, such as hydroxides, carbonates or amines. Sodium hydroxide, sodium carbonate, potassium carbonate, pyridine and triethylamine may be mentioned by way of example.

The reaction can be carried out at atmospheric pressure or under elevated pressure and is preferably carried out at atmospheric pressure. Work-up is carried out by customary methods of organic chemistry. The end products are preferably purified by crystallization, chromatographic purification or "incipient distillation", i.e. removal of the volatile components under reduced pressure.

The process (G) is characterized in that compounds of the formula (I-a) are reacted with metal hydroxides or metal alkoxides of the formula (IX) or amines of the formula (X), if appropriate in the presence of a diluent.

Suitable diluents for use in the process (G) according to the invention are, preferably, ethers, such as tetrahydrofuran, dioxane, diethyl ether, or else alcohols, such as methanol, ethanol, isopropanol, and also water.

The process (G) according to the invention is generally carried out under atmospheric pressure.

The reaction temperatures are generally between −20° C. and 100° C., preferably between 0° C. and 50° C.

The process (H) according to the invention is characterized in that compounds of the formula (I-a) are reacted with (H-α) compounds of the formula (XI), if appropriate in the presence of a diluent and if appropriate in the presence of a catalyst, or (H-β) with compounds of the formula (XII), if appropriate in the presence of a diluent and if appropriate in the presence of an acid binder.

In preparation process (H-α), about 1 mol of isocyanate of the formula (XI) is reacted per mole of starting material of the formula (I-a), at from 0 to 100° C., preferably from 20 to 50° C.

Suitable diluents which are added, if appropriate, are all inert organic solvents, such as ethers, amides, nitriles, sulphones or sulphoxides.

If appropriate, catalysts may be added to accelerate the reaction. Suitable for use as catalysts are, very advantageously, organotin compounds, such as, for example, dibutyltin dilaurate. The reaction is preferably carried out at atmospheric pressure.

In preparation process (H-β), about 1 mol of carbamoyl chloride of the formula (XII) is reacted per mole of starting compound of the formula (I-a), at from −20 to 150° C., preferably at from 0 to 70° C.

Suitable diluents which are added, if appropriate, are all inert polar organic solvents, such as ethers, amides, sulphones, sulphoxides or halogenated hydrocarbons.

Preference is given to using dimethyl sulphoxide, tetrahydrofuran, dimethylformamide or methylene chloride.

If, in a preferred embodiment, the enolate salt of the compound (I-a) is prepared by addition of strong deprotonating agents (such as, for example, sodium hydride or potassium tert-butoxide), the further addition of acid binders may be dispensed with.

If acid binders are used, these are customary inorganic or organic bases, for example sodium hydroxide, sodium carbonate, potassium carbonate, triethylamine or pyridine.

The reaction can be carried out at atmospheric pressure or under elevated pressure and is preferably carried out at atmospheric pressure. Work-up is carried out by customary methods.

The active compounds of the invention, in combination with good plant tolerance and favourable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They may be preferably employed as crop protection agents. They are active against normally sensitive and resistant species and against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici.*

From the class of the Bivalva, for example, *Dreissena* spp.

From the order of the Chilopoda, for example, *Geophilus* spp., *Scutigera* spp.

From the order of the Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.

From the order of the Collembola, for example, *Onychiurus armatus.*

From the order of the Dermaptera, for example, *Forficula auricularia.*

From the order of the Diplopoda, for example, *Blaniulus guttulatus.*

From the order of the Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahrtia* spp.

From the class of the Gastropoda, for example, *Arion* spp., *Biomphalaria* spp., *Bulinus* spp., *Deroceras* spp., *Galba* spp., *Lymnaea* spp., *Oncomelania* spp., *Succinea* spp.

From the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medin-* ensis, *Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti.*

It is furthermore possible to control protozoa, such as Eimeria.

From the order of the Heteroptera, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.

From the order of the Homoptera, for example, *Acyrthosipon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva fimbriolata, Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii.*

From the order of the Hymenoptera, for example, *Diprion* spp., *Hoplocampa* spp., *Lasius* spp., *Monomorium pharaonis, Vespa* spp.

From the order of the Isopoda, for example, *Armadillidium vulgare, Oniscus asellus, Porcellio scaber.*

From the order of the Isoptera, for example, *Reticulitermes* spp., *Odontotermes* spp.

From the order of the Lepidoptera, for example, *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Chematobia brumata, Chilo* spp., *Choristoneura fumiferana, Clysia ambiguella, Cnaphalocerus* spp., *Earias insulana, Ephestia kuehniella, Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Lithocolletis blancardella, Lithophane antennata, Loxagrotis albicosta, Lymantria* spp., *Malacosoma neustria, Mamestra brassicae, Mocis repanda, Mythimna separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrix viridana, Trichoplusia* spp.

From the order of the Orthoptera, for example, *Acheta domesticus, Blatta orientalis, Blattella germanica, Gryllotalpa* spp., *Leucophaea maderae, Locusta* spp., *Melanoplus* spp., *Periplaneta americana, Schistocerca gregaria.*

From the order of the Siphonaptera, for example, *Ceratophyllus* spp., *Xenopsylla cheopis.*

From the order of the Symphyla, for example, *Scutigerella immaculata.*

From the order of the Thysanoptera, for example, *Baliothrips biformis, Enneothrips flavens, Frankliniella* spp., *Heliothrips* spp., *Hercinothrips femoralis, Kakothrips* spp., *Rhipiphorothrips cruentatus, Scirtothrips* spp., *Taeniothrips cardamoni, Thrips* spp.

From the order of the Thysanura, for example, *Lepisma saccharina.*

The phytoparasitic nematodes include, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans, Xiphinema* spp.

If appropriate, the compounds according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (Mycoplasma-like organisms) and RLO (Rickettsia-like organisms). If appropriate, they can also be employed as intermediates or precursors for the synthesis of other active compounds.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Treatment according to the invention of the plants and plant parts with the active compounds is carried out directly or by allowing the compounds to act on the surroundings, habitat or storage space by the customary treatment methods, for example by immersion, spraying, evaporation, fogging, scattering, painting on, injection and, in the case of propagation material, in particular in the case of seeds, also by applying one or more coats.

The active compounds can be converted to the customary formulations, such as solutions, emulsions, wettable powders, water- and oil-based suspensions, powders, dusts, pastes, soluble powders, soluble granules, granules for broadcasting, suspension-emulsion concentrates, natural materials impregnated with active compound, synthetic materials impregnated with active compound, fertilizers and microencapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers. The formulations are prepared either in suitable plants or else before or during the application.

Suitable for use as auxiliaries are substances which are suitable for imparting to the composition itself and/or to preparations derived therefrom (for example spray liquors, seed dressings) particular properties such as certain technical properties and/or also particular biological properties. Typical suitable auxiliaries are: extenders, solvents and carriers.

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulphoxide, and also water.

Suitable Solid Carriers are:
for example, ammonium salts and ground natural minerals such as kaolins, clays, talc, chalk, quartz, attapulgite, montmorillonite or diatomaceous earth, and ground synthetic minerals, such as finely divided silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE and/or -POP ethers, acid and/or POP-POE esters, alkylaryl and/or POP-POE ethers, fat- and/or POP-POE adducts, POE- and/or POP-polyol derivatives, POE- and/or POP-sorbitan- or -sugar adducts, alkyl or aryl sulphates, alkyl- or arylsulphonates and alkyl or aryl phosphates or the corresponding PO-ether adducts. Furthermore, suitable oligo- or polymers, for example those derived from vinylic monomers, from acrylic acid, from EO and/or PO alone or in combination with, for example, (poly)alcohols or (poly)amines. It is also possible to employ lignin and its sulphonic acid derivatives, unmodified and modified celluloses, aromatic and/or aliphatic sulphonic acids and their adducts with formaldehyde.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Other possible additives are perfumes, mineral or vegetable, optionally modified oils, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present.

The formulations generally comprise between 0.01 and 98% by weight of active compound, preferably between 0.5 and 90%.

The active compound according to the invention can be used in its commercially available formulations and in the use forms, prepared from these formulations, as a mixture with other active compounds, such as insecticides, attractants, sterilizing agents, bactericides, acaricides, nematicides, fungicides, growth-regulating substances, herbicides, safeners, fertilizers or semiochemicals.

Particularly favourable mixing components are, for example, the following compounds:
Fungicides:
Inhibitors of Nucleic Acid Synthesis
  benalaxyl, benalaxyl-M, bupirimate, chiralaxyl, clozylacon, dimethirimol, ethirimol, furalaxyl, hymexazole, metalaxyl, metalaxyl-M, ofurace, oxadixyl, oxolinic acid
Inhibitors of Mitosis and Cell Division
  benomyl, carbendazim, diethofencarb, fuberidazole, pencycuron, thiabendazole, thiophanate-methyl, zoxamide
Inhibitors of Respiratory Chain Complex I
  diflumetorim
Inhibitors of Respiratory Chain Complex II
  boscalid, carboxin, fenfuram, flutolanil, furametpyr, mepronil, oxycarboxin, penthiopyrad, thifluzamide
Inhibitors of Respiratory Chain Complex III
  azoxystrobin, cyazofamid, dimoxystrobin, enestrobin, famoxadone, fenamidone, fluoxastrobin, kresoxim-methyl, metominostrobin, orysastrobin, pyraclostrobin, picoxystrobin, trifloxystrobin Decouplers
  dinocap, fluazinam
Inhibitors of ATP Production
  fentin acetate, fentin chloride, fentin hydroxide, silthiofam
Inhibitors of Amino Acid Biosynthesis and Protein Biosynthesis
  andoprim, blasticidin-S, cyprodinil, kasugamycin, kasugamycin hydrochloride hydrate, mepanipyrim, pyrimethanil
Inhibitors of Signal Transduction
  fenpiclonil, fludioxonil, quinoxyfen
Inhibitors of Lipid and Membrane Synthesis
  chlozolinate, iprodione, procymidone, vinclozolin
  ampropylfos, potassium-ampropylfos, edifenphos, iprobenfos (IBP), isoprothiolane, pyrazophos
  tolclofos-methyl, biphenyl
  iodocarb, propamocarb, propamocarb hydrochloride
Inhibitors of Ergosterol Biosynthesis
  fenhexamid,
  azaconazole, bitertanol, bromuconazole, cyproconazole, diclobutrazole, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole, voriconazole, imazalil, imazalil sulphate, oxpoconazole, fenarimol, flurprimidol, nuarimol, pyrifenox, triforine, pefurazoate, prochloraz, triflumizole, viniconazole,
  aldimorph, dodemorph, dodemorph acetate, fenpropimorph, tridemorph, fenpropidin, spiroxamine,
  naftifine, pyributicarb, terbinafine
Inhibitors of Cell Wall Synthesis
  benthiavalicarb, bialaphos, dimethomorph, flumorph, iprovalicarb, polyoxins, polyoxorim, validamycin A
Inhibitors of Melanin Biosynthesis
  capropamid, diclocymet, fenoxanil, phthalid, pyroquilon, tricyclazole
Resistance Inductors
  acibenzolar-S-methyl, probenazole, tiadinil
Multisite
  captafol, captan, chlorothalonil, copper salts such as: copper hydroxide, copper naphthenate, copper oxychloride, copper sulphate, copper oxide, oxine-copper and Bordeaux mixture, dichlofluanid, dithianon, dodine, dodine free base, ferbam, folpet, fluorofolpet, guazatine, guazatine acetate, iminoctadine, iminoctadine albesilate, iminoctadine triacetate, mancopper, mancozeb, maneb, metiram, metiram zinc, propineb, sulphur and sulphur preparations containing calcium polysulphide, thiram, tolylfluanid, zineb, ziram
Unknown Mechanism
  amibromdol, benthiazole, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methyl sulphate, diphenylamine, ethaboxam, ferimzone, flumetover, flusulphamide, fluopicolide, fluoroimide, hexachlorobenzene, 8-hydroxy-quinoline sulphate, irumamycin, methasulphocarb, metrafenone, methyl isothiocyanate, mildiomycin, natamycin, nickel dimethyl dithiocarbamate, nitrothal-isopropyl, octhilinone, oxamocarb, oxyfenthiin, pentachlorophenol and salts, 2-phenylphenol and salts, piperalin, propanosine-sodium, proquinazid, pyrrolnitrin, quintozene, tecloftalam, tecnazene, triazoxide, trichlamide, zarilamid and 2,3,5,6-tetrachloro-4-(methylsulphonyl)pyridine, N-(4-chloro-2-nitrophenyl)-N-ethyl-4-methylbenzenesulphonamide, 2-amino-4-methyl-N-phenyl-5-thiazolecarboxamide, 2-chloro-N-(2,3-dihydro-1,1,3-trimethyl-1H-inden-4-yl)-3-pyridinecarboxamide, 3-[5-(4-chlorophenyl)-2,3-dimethylisoxazolidin-3-yl] pyridine, cis-1-(4-chlorophenyl)-2-(1H-1,2,4-triazol-1-yl)cycloheptanol, 2,4-dihydro-5-methoxy-2-methyl-4-[[[[1-[3-(trifluoromethyl)phenyl]ethylidene]amino] oxy]methyl]phenyl]-3H-1,2,3-triazol-3-one (185336-79-2), methyl 1-(2,3-dihydro-2,2-dimethyl-1H-inden-1-yl)-1H-imidazole-5-carboxylate, 3,4,5-trichloro-2,6-pyridinedicarbonitrile, methyl 2-[[[cyclopropyl[(4-methoxyphenyl)imino]methyl]thio]methyl]-.alpha.-(methoxymethylene)benzacetate, 4-chloro-alpha-propynyloxy-N-[2-[3-methoxy-4-(2-propynyloxy) phenyl]ethyl]benzacet-amide, (2S)—N-[2-[4-[[3-(4-chlorophenyl)-2-propynyl]oxy]-3-methoxyphenyl] ethyl]-3-methyl-2-[(methylsulphonyl)amino] butanamide, 5-chloro-7-(4-methylpiperidin-1-yl)-6-(2,4,6-trifluorophenyl)[1,2,4]triazolo[1,5-a]pyrimidine, 5-chloro-6-(2,4,6-trifluorophenyl)-N-[(1R)-1,2,2-trimethylpropyl][1,2,4]triazolo[1,5-a]pyrimidin-7-amine, 5-chloro-N-[(1R)-1,2-dimethylpropyl]-6-(2,4,6-trifluorophenyl)[1,2,4]triazolo[1,5-a]pyrimidin-7-amine, N-[1-(5-bromo-3-chloropyridin-2-yl)ethyl]-2,4-dichloronicotinamide, N-(5-bromo-3-chloropyridin-2-yl)methyl-2,4-dichloronicotinamide, 2-butoxy-6-iodo-3-propylbenzopyranon-4-one, N-{(Z)-[(cyclopropylmethoxy)imino][6-(difluoromethoxy)-2,3-difluorophenyl]-methyl}-2-benzacetamide, N-(3-ethyl-3,5,5-trimethylcyclohexyl)-3-formylamino-2-hydroxybenzamide, 2-[[[[1-[3(1-fluoro-2-phenylethyl) oxy]phenyl]ethylidene]amino]oxy]-methyl]-alpha-(methoxyimino)-N-methyl-alphaE-benzacetamide, N-{2-[3-chloro-5-(trifluoromethyl)pyridin-2-yl]ethyl}-2-(trifluoromethyl)benzamide, N-(3',4'-dichloro-5-fluoro-biphenyl-2-yl)-3-(difluoromethyl)-1-methyl-1H-pyrazole-4-carboxamide, N-(6-methoxy-3-pyridinyl)cyclopropanecarboxamide, 1-[(4-methoxyphenoxy)methyl]-2,2-dimethylpropyl-1H-imidazole-1-carboxylic acid, O-[1-[(4-methoxyphenoxy)methyl]-2,2-dimethylpropyl]-1H-imidazole-1-carbothioic acid, 2-(2-{[6-(3-chloro-2-methylphenoxy)-5-fluoropyrimidin-4-yl]oxy}phenyl)-2-(methoxyimino)-N-methylacetamide
Bactericides:
bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.
Insecticides/Acaricides/Nematicides:
  Acetylcholine Esterase (AChE) Inhibitors
  carbamates,
    for example alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulphan, cloethocarb, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, trimethacarb, XMC, xylylcarb, triazamate
  organophosphates,
    for example acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-S-methyl, demeton-S-methylsulphone, dialifos, diazinon, dichlofenthion, dichlorvos/DDVP, dicrotophos, dimethoate, dimethylvinphos, dioxabenzofos, disulphoton, EPN, ethion, ethoprophos, etrimfos, famphur, fenamiphos, fenitrothion, fensulphothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulphotep, sulprofos, tebupirimfos, temephos, terbufos, tetrachlorvinphos, thiometon, triazophos, triclorfon, vamidothion Sodium Channel Modulators/Voltage-Dependent Sodium Channel Blockers pyrethroids,
for example acrinathrin, allethrin (d-cis-trans, d-trans), beta-cyfluthrin, bifenthrin, bioallethrin, bioallethrin-S-cyclopentyl isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermethrin (alpha-, beta-, theta-, zeta-), cyphenothrin, deltamethrin, empenthrin (1R isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R-trans isomer), prallethrin, profluthrin, protrifenbute, pyresmethrin, resmethrin, RU 15525, silafluofen, tau-fluvalinate, tefluthrin, teralethrin, tetramethrin (1R isomer), tralomethrin, transfluthrin, ZXI 8901, pyrethrins (pyrethrum)

DDT oxadiazines,
for example indoxacarb semicarbazones,
for example metaflumizone (BAS3201)

Acetylcholine Receptor Agonists/Antagonists chloronicotinyls,
for example acetamiprid, clothianidin, dinotefuran, imidacloprid, nitenpyram, nithiazine, thiacloprid, thiamethoxam
nicotine, bensultap, cartap Acetylcholine Receptor Modulators spinosyns,
for example spinosad GABA-Controlled Chloride Channel Antagonists organochlorines,
for example camphechlor, chlordane, endosulphan, gamma-HCH, HCH, heptachlor, lindane, methoxychlor fiprols,
for example acetoprole, ethiprole, fipronil, pyrafluprole, pyriprole, vaniliprole Chloride Channel Activators mectins,
for example abamectin, emamectin, emamectin-benzoate, ivermectin, lepimectin, milbemycin Juvenile Hormone Mimetics,
for example diofenolan, epofenonane, fenoxycarb, hydroprene, kinoprene, methoprene, pyriproxifen, triprene Ecdysone Agonists/Disruptors diacylhydrazines,
for example chromafenozide, halofenozide, methoxyfenozide, tebufenozide Chitin Biosynthesis Inhibitors benzoylureas,
for example bistrifluoron, chlofluazuron, diflubenzuron, fluazuron, flucycloxuron, flufenoxuron, hexaflumuron, lufenuron, novaluron, noviflumuron, penfluoron, teflubenzuron, triflumuron buprofezin cyromazine Oxidative Phosphorylation Inhibitors, ATP Disruptors diafenthiuron organotin compounds,
for example azocyclotin, cyhexatin, fenbutatin-oxide Oxidative Phosphorylation Decouplers Acting by Interrupting the H-Proton Gradient pyrroles,
for example chlorfenapyr dinitrophenols,
for example binapacyrl, dinobuton, dinocap, DNOC, meptyldinocap Site-I Electron Transport Inhibitors METI's,
for example fenazaquin, fenpyroximate, pyrimidifen, pyridaben, tebufenpyrad, tolfenpyrad hydramethylnon dicofol Site-II Electron Transport Inhibitors rotenone Site-III Electron Transport Inhibitors acequinocyl, fluacrypyrim Microbial Disruptors of the Insect Gut Membrane

*Bacillus thuringiensis* strains

Lipid Synthesis Inhibitors tetronic acids,
for example spirodiclofen, spiromesifen tetramic acids,
for example spirotetramate, cis-3-(2,5-dimethylphenyl)-4-hydroxy-8-methoxy-1-azaspiro[4.5]dec-3-en-2-one carboxamides,
for example flonicamid octopaminergic agonists,
for example amitraz Inhibitors of Magnesium-Stimulated ATPase, propargite nereistoxin analogues,
for example thiocyclam hydrogen oxalate, thiosultap-sodium Ryanodine Receptor Agonists, benzodicarboxamides,
for example flubendiamide anthranilamides,
for example rynaxypyr (3-bromo-N-{4-chloro-2-methyl-6-[(methylamino)carbonyl]-phenyl}-1-(3-chloropyridin-2-yl)-1H-pyrazole-5-carboxamide)

Biologicals, Hormones or Pheromones azadirachtin, *Bacillus* spec., *Beauveria* spec., *codlemone*, *Metarrhizium* spec., *Paecilomyces* spec., *thuringiensin*, *Verticillium* spec.

Active Compounds with Unknown or Unspecific Mechanisms of Action fumigants, for example aluminium phosphide, methyl bromide, sulphuryl fluoride antifeedants, for example cryolite, flonicamid, pymetrozine mite growth inhibitors, for example clofentezine, etoxazole, hexythiazox amidoflumet, benclothiaz, benzoximate, bifenazate, bromopropylate, buprofezin, chinomethionat, chlordimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyridalyl, sulphluramid, tetradifon, tetrasul, triarathene, verbutin A mixture with other known active compounds, such as herbicides, fertilizers, growth regulators, safeners, semiochemicals, or else with agents for improving the plant properties, is also possible.

When used as insecticides, the active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

When used as insecticides, the active compounds according to the invention can furthermore be present in their commercially available formulations and in the use forms, prepared from these formulations, as a mixture with inhibitors which reduce degradation of the active compound after use in the environment of the plant, on the surface of parts of plants or in plant tissues.

The active compound content of the use forms prepared from the commercially available formulations can vary within wide limits. The active compound concentration of the use forms can be from 0.00000001 to 95% by weight of active compound, preferably between 0.00001 and 1% by weight.

The compounds are employed in a customary manner appropriate for the use forms.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (Genetically Modified Organisms), and parts thereof are treated. The terms "parts", "parts of plants" and "plant parts" have been explained above.

Particularly preferably, plants of the plant cultivars which are in each case commercially available or in use are treated according to the invention. Plant cultivars are to be understood as meaning plants having novel properties ("traits") which have been obtained by conventional breeding, by mutagenesis or by recombinant DNA techniques. These can be cultivars, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The preferred transgenic plants or plant cultivars (obtained by genetic engineering) which are to be treated according to the invention include all plants which, by virtue of the genetic modification, received genetic material which imparts particular advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products. Further and particularly emphasized examples of such traits are a better defense of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, sugar beet, tomatoes, peas and other vegetable varieties, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized are in particular increased defense of the plants against insects, arachnids, nematodes and slugs and snails by virtue of toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (referred to hereinbelow as "Bt plants"). Traits that are also particularly emphasized are the increased defense of plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of plants to certain herbicidally active compounds, for example imidazolinones, sulphonylureas, glyphosate or phosphinothricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinothricin, for example oilseed rape), IMP® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plant cultivars will be developed and/or marketed in the future.

The plants listed can be treated according to the invention in a particularly advantageous manner with the compounds of the general formula I and/or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The active compounds according to the invention act not only against plant, hygiene and stored product pests, but also in the veterinary medicine sector against animal parasites (ecto- and endoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp., *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.

From the order of the Siphonapterida, for example, *Pulex* spp., *Ctenocephalides* spp., *Xenopsylla* spp., *Ceratophyllus* spp.

From the order of the Heteropterida, for example, *Cimex* spp., *Triatoma* spp., *Rhodnius* spp., *Panstrongylus* spp.

From the order of the Blattarida, for example, *Blatta orientalis, Periplaneta americana, Blattela germanica, Supella* spp.

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp., *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reductions in productivity (for meat, milk, wool, hides, eggs, honey etc.) should be diminished, so that more economic and easier animal husbandry is possible by use of the active compounds according to the invention.

The active compounds according to the invention are used in the veterinary sector and in animal husbandry in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, pets and the like, the active compounds of the formula (I) can be used as formulations (for example powders, emulsions, free-flowing compositions), which comprise the active compounds in an amount of 1 to 80% by weight, directly or after 100- to 10 000-fold dilution, or they can be used as a chemical bath.

It has furthermore been found that the compounds according to the invention also have a strong insecticidal action against insects which destroy industrial materials.

The following insects may be mentioned as examples and as preferred—but without any limitation:

Beetles, such as *Hylotrupes bajulus, Chlorophorus pilosis, Anobium punctatum, Xestobium rufovillosum, Ptilinus pectinicornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus minutus;*

Hymenopterons, such as *Sirex juvencus, Urocerus gigas, Urocerus gigas taignus, Urocerus augur;*

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;*

Bristletails, such as *Lepisma saccharina*.

Industrial materials in the present connection are to be understood as meaning non-living materials, such as, preferably, plastics, adhesives, sizes, papers and cardboards, leather, wood and processed wood products and coating compositions.

The ready-to-use compositions may, if appropriate, comprise further insecticides and, if appropriate, one or more fungicides.

With respect to possible additional additives, reference may be made to the insecticides and fungicides mentioned above.

The compounds according to the invention can likewise be employed for protecting objects which come into contact with saltwater or brackish water, in particular hulls, screens, nets, buildings, moorings and signalling systems, against fouling.

Furthermore, the compounds according to the invention, alone or in combinations with other active compounds, may be employed as antifouling agents.

In domestic, hygiene and stored-product protection, the active compounds are also suitable for controlling animal pests, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all developmental stages. These pests include:

From the order of the Scorpionidea, for example, *Buthus occitanus*.

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order of the Araneae, for example, Aviculariidae, Araneidae.

From the order of the Opiliones, for example, *Pseudoscorpiones chelifer, Pseudoscorpiones cheiridium, Opiliones phalangium*.

From the order of the Isopoda, for example, *Oniscus asellus, Porcellio scaber*.

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus*.

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa*.

From the order of the Saltatoria, for example, *Acheta domesticus*.

From the order of the Dermaptera, for example, *Forficula auricularia*.

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa*.

From the order of the Lepidoptera, for example, *Achroia grisella, Galleria mellonella, Plodia interpunctella, Tinea cloacella, Tinea pellionella, Tineola bisselliella*.

From the order of the Siphonaptera, for example, *Ctenocephalides canis, Ctenocephalides felis, Pulex irritans, Tunga penetrans, Xenopsylla cheopis*.

From the order of the Hymenoptera, for example, *Camponotus herculeanus, Lasius fuliginosus, Lasius niger, Lasius umbratus, Monomorium pharaonis, Paravespula* spp., *Tetramorium caespitum*.

From the order of the Anoplura, for example, *Pediculus humanus capitis, Pediculus humanus corporis, Pemphigus* spp., *Phylloera vastatrix, Phthirus pubis*.

From the order of the Heteroptera, for example, *Cimex hemipterus, Cimex lectularius, Rhodinus prolixus, Triatoma infestans*.

In the field of household insecticides, they are used alone or in combination with other suitable active compounds, such as phosphoric esters, carbamates, pyrethroids, neonicotinoids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

The active compounds according to the invention can also be used as defoliants, desiccants, haulm killers and, in particular, as weed killers. Weeds in the broadest sense are understood as meaning all plants which grow at locations where they are undesired. Whether the substances according to the invention act as nonselective or selective herbicides depends essentially on the application rate.

The active compounds according to the invention can be used for example in the following plants:

Dicotyledonous weeds of the genera: *Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium*.

Dicotyledonous crops of the genera: *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia*.

Monocotyledonous weeds of the genera: *Aegilops, Agropyron, Agrostis, Alopecurus, Apera, Avena, Brachiaria, Bromus, Cenchrus, Commelina, Cynodon, Cyperus, Dactyloctenium, Digi-taria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum*.

Monocotyledonous crops of the genera: *Allium, Ananas, Asparagus, Avena, Hordeum, Oryza, Panicum, Saccharum, Secale, Sorghum, Triticale, Triticum, Zea*.

However, the use of the active compounds according to the invention is in no way restricted to these genera, but extends in the same manner to other plants.

Depending on the concentration, the active compounds according to the invention are suitable for the nonselective weed control on, for example, industrial terrains and railway tracks and on paths and locations with and without trees. Likewise the active compounds according to the invention can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantings and hop fields, on lawns, turf and pastureland, and for the selective control of weeds in annual crops.

The active compounds according to the invention have strong herbicidal activity and a broad activity spectrum when used on the soil and on aerial plant parts. To a certain extent, they are also suitable for the selective control of monocotyledonous and dicotyledonous weeds in monocotyledonous and dicotyledonous crops, both pre- and post-emergence.

At certain concentrations or application rates, the active compounds according to the invention can also be employed for controlling animal pests and fungal or bacterial plant diseases. If appropriate, they can also be used as intermediates or precursors for the synthesis of other active compounds.

The active compounds can be converted into the customary formulations, such as solutions, emulsions, wettable powders, suspensions, powders, dusts, pastes, soluble powders, granules, suspoemulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers.

If the extender used is water, it is also possible to use, for example, organic solvents as auxiliary solvents. Suitable liquid solvents are essentially: aromatics, such as xylene, toluene or alkyl-naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulphoxide, and also water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates, suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, and also natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 percent by weight of active compound, preferably between 0.5 and 90%.

The active compounds according to the invention, as such or in their formulations, can also be used for weed control purposes as a mixture with known herbicides and/or with substances which improve crop plant tolerance ("safeners"), ready mixes or tank mixes being possible. Mixtures with herbicide products which contain one or more known herbicides and a safener are hence also possible.

Herbicides which are suitable for the mixtures are known herbicides, for example 2-chloro-5-[2,6-dioxo-4-(trifluoromethyl)-3,6-dihydropyrimidin-1(2H)-yl]-4-fluoro-N-[methyl(1-methylethyl)sulphamoyl]benzamide, acetochlor, acifluorfen (-sodium), aclonifen, alachlor, alloxydim (-sodium), ametryne, amicarbazone, amidochlor, amidosulphuron, aminopyralid, anilofos, asulam, atrazine, azafenidin, azimsulphuron, beflubutamid, benazolin (-ethyl), bencarbazone, benfuresate, bensulphuron (-methyl), bentazone, benzfendizone, benzobicyclon, benzofenap, benzoylprop (-ethyl), bialaphos, bifenox, bispyribac (-sodium), bromobutide, bromofenoxim, bromoxynil, butachlor, butafenacil (-allyl), butroxydim, butylate, cafenstrole, caloxydim, carbetamide, carfentrazone (-ethyl), chlomethoxyfen, chloramben, chloridazon, chlorimuron (-ethyl), chlornitrofen, chlorsulphuron, chlortoluron, cinidon (-ethyl), cinmethylin, cinosulphuron, clefoxydim, clethodim, clodinafop (-propargyl), clomazone, clomeprop, clopyralid, clopyrasulphuron (-methyl), cloransulam (-methyl), cumyluron, cyanazine, cybutryne, cycloate, cyclosulfamuron, cycloxydim, cyhalofop (-butyl), 2,4-D, 2,4-DB, desmedipham, diallate, dicamba, dichlorprop (-P), diclofop (-methyl), diclosulam, diethatyl (-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epropodan, EPTC, esprocarb, ethalfluralin, ethametsulphuron (-methyl), ethofumesate, ethoxyfen, ethoxysulphuron, etobenzanid, fenoxaprop (-P-ethyl), fentrazamide, flamprop (-isopropyl, -isopropyl-L, -methyl), flazasulphuron, florasulam, fluazifop (-P-butyl), fluazolate, flucarbazone (-sodium), flufenacet, flumetsulam, flumiclorac (-pentyl), flumioxazin, flumipropyn, flumetsulam, fluometuron, fluorochloridone, fluoroglycofen (-ethyl), flupoxam, flupropacil, flurpyrsulphuron (-methyl, -sodium), flurenol (-butyl), fluridone, fluoroxypyr (-butoxypropyl, -meptyl), flurprimidol, flurtamone, fluthiacet (-methyl), fluthiamide, fomesafen, foramsulphuron, glufosinate (-ammonium), glyphosate (-isopropylammonium), halosafen, haloxyfop (-ethoxyethyl, -P-methyl), hexazinone, HOK-201, imazamethabenz (-methyl), imazamethapyr, imazamox, imazapic, imazapyr, imazaquin, imazethapyr, imazosulphuron, iodosulphuron (-methyl, -sodium), ioxynil, isopropalin, isoproturon, isouron, isoxaben, isoxachlortole, isoxaflutole, isoxapyrifop, lactofen, lenacil, linuron, MCPA, mecoprop, mefenacet, mesosulphurone, mesotrione, metamifop, metamitron, metazachlor, methabenzthiazuron, metobenzuron, metobromuron, (alpha-)metolachlor, metosulam, metoxuron, metribuzin, metsulphuron (-methyl), molinate, monolinuron, naproanilide, napropamide, neburon, nicosulphuron, norflurazon, orbencarb, orthosulfamuron, oryzalin, oxadiargyl, oxadiazon, oxasulphuron, oxaziclomefone, oxyfluorfen, paraquat, pelargonic acid, pendimethalin, pendralin, penoxsulam, pentoxazone, phenmedipham, picolinafen, pinoxaden, piperophos, pretilachlor, primisulphuron (-methyl), profluazol, prometryn, propachlor, propanil, propaquizafop, propisochlor, propoxycarbazone (-sodium), propyzamide, prosulfocarb, prosulphuron, pyraflufen (-ethyl), pyrasulfotole, pyrazogyl, pyrazolate, pyrazosulphuron (-ethyl), pyrazoxyfen, pyribenzoxim, pyributicarb, pyridate, pyridatol, pyriftalide, pyriminobac (-methyl), pyrimisulfan, pyrithiobac (-sodium), pyroxasulfone, quinchlorac, quinmerac, quinoclamine, quizalofop (-P-ethyl, -P-tefuryl), rimsulphuron, sethoxydim, simazine, simetryn, sulcotrione, sulfentrazone, sulfometuron (-methyl), sulfosate, sulfosulphuron, tebutam, tebuthiuron, tembotrione, tepraloxydim, terbuthylazine, terbutryn, thenylchlor, thiafluamide, thiazopyr, thidiazimin, thifensulphuron (-methyl), thiobencarb, tiocarbazil, topramezone, tralkoxydim, triallate, triasulphuron, tribenuron (-methyl), triclopyr, tridiphane, trifluralin, trifloxysulphuron, triflusulphuron (-methyl), tritosulphuron and

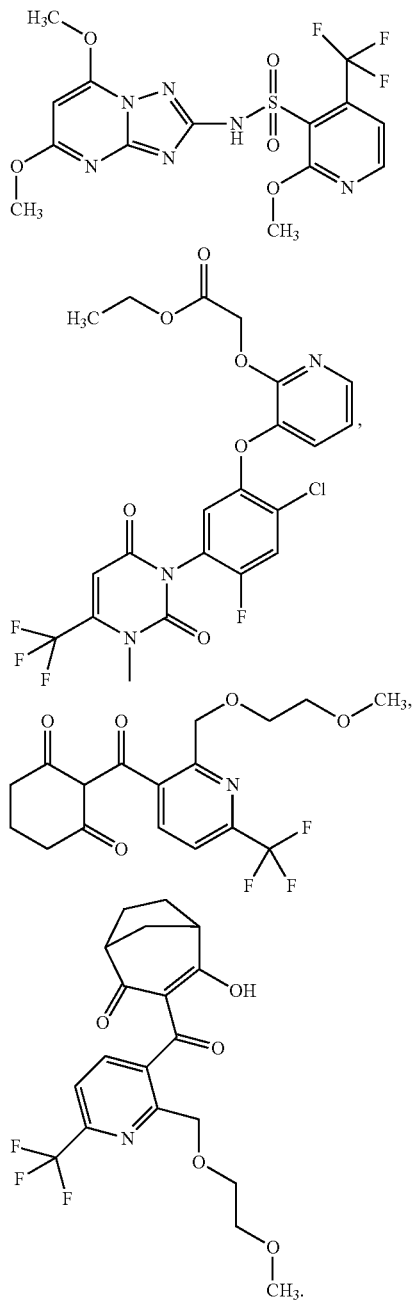

A mixture with other known active compounds, such as fungicides, insectides, acaricides, nematicides, bird repellents, plant nutrients and soil conditioners, is also possible.

The active compounds or active compound combinations can be applied as such, in the form of their formulations or the use forms prepared therefrom by further dilution, such as ready-to-use solutions, suspensions, emulsions, powders, pastes and granules. They are applied in the customary manner, for example by watering, spraying, atomizing, spreading.

The active compounds or active compound combinations according to the invention can be applied both before and after plant emergence. They can also be incorporated into the soil prior to planting.

The application rate of active compound can vary within a substantial range. Essentially, it depends on the nature of the desired effect. In general, the application rates are between 1 g and 10 kg of active compound per hectare of soil area, preferably between 5 g and 5 kg per ha.

The advantageous effect of the compatibility with crop plants of the active compound combinations according to the invention is particularly pronounced at certain concentration ratios. However, the weight ratios of the active compounds in the active compound combinations can be varied within relatively wide ranges. In general, from 0.001 to 1000 parts by weight, preferably from 0.01 to 100 parts by weight, particularly preferably 0.05 to 20 parts by weight, of one of the compounds which improves crop plant compatibility (antidotes/safeners) mentioned above under (b') are present per part by weight of active compound of the formula (I).

The active compound combinations according to the invention are generally applied in the form of finished formulations. However, the active compounds contained in the active compound combinations can, as individual formulations, also be mixed during use, i.e. be applied in the form of tank mixes.

For certain applications, in particular by the post-emergence method, it may furthermore be advantageous to include, as further additives in the formulations, mineral or vegetable oils which are tolerated by plants (for example the commercial preparation "Rako Binol"), or ammonium salts, such as, for example, ammonium sulphate or ammonium thiocyanate.

The novel active compound combinations can be used as such, in the form of their formulations or the use forms prepared therefrom by further dilution, such as ready-to-use solutions, suspensions, emulsions, powders, pastes and granules. Application is in the customary mariner, for example by watering, spraying, atomizing, dusting or scattering.

The application rates of the active compound combinations according to the invention can be varied within a certain range; they depend, inter alia, on the weather and on soil factors. In general, the application rates are between 0.001 and 5 kg per ha, preferably between 0.005 and 2 kg per ha, particularly preferably between 0.01 and 0.5 kg per ha.

The active compound combinations according to the invention can be applied before and after emergence of the plants, that is to say by the pre-emergence and post-emergence method.

Depending on their properties, the safeners to be used according to the invention can be used for pretreating the seed of the crop plant (seed dressing) or can be introduced into the seed furrows prior to sowing or be used separately prior to the herbicide or together with the herbicide, before or after emergence of the plants.

Examples of plants which may be mentioned are important crop plants, such as cereals (wheat, barley, rice), maize, soya beans, potatoes, cotton, oilseed rape, beet, sugar cane and also fruit plants (with the fruits apples, pears, citrus fruits and grapes), particular emphasis being given to cereals, maize, soya beans, potatoes, cotton and oilseed rape.

The term "active compounds" always also includes the active compound combinations mentioned here.

Preparation and use of the active compounds according to the invention is illustrated by the examples below.

USE EXAMPLES

Example I-a-1

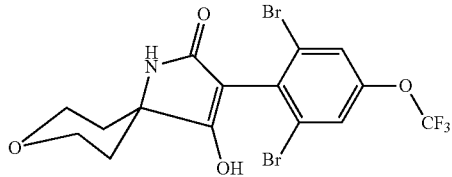 [SMILES: O=C1NC2(CCOCC2)C(O)=C1c1c(Br)cc(OC(F)(F)F)cc1Br]

Under argon, 4.26 g of potassium tertbutoxide (36 mmol) are initially charged in 10 ml of dimethylacetamide. At −20 to −30° C., 8.5 g (16.4 mmol) of the compound according to Example II-1 in 15 ml of dimethylacetamide are added dropwise. The mixture is stirred at 20° C. for 1 hour (the reaction is monitored by thin-layer chromatography). After the reaction has ended, the reaction solution is stirred into 100 ml of ice-water, the pH is adjusted to 2 using concentrated hydrochloric acid and the precipitate is filtered off with suction. The precipitate is redissolved in 40 ml of dichloromethane, and 20 ml of a 0.5 N solution of NaOH are added dropwise. The mixture is stirred at 20° C. for 1 hour. The aqueous phase is adjusted to pH 2 and the precipitate is filtered off with suction.

The product is purified by column chromatography on silica gel (dichloromethane:ethyl acetate=5:3).

Yield: 4.2 g (51% of theory), m.p. 259° C.

Analogously to Example (I-a-1) and in accordance with the general statements on the preparation, the following compounds of the formula (I-a) are obtained:

(I-a)

| Ex. No. | J | X | Y | D | A | B | m.p. °C. | Isomer |
|---|---|---|---|---|---|---|---|---|
| I-a-2 | 2-OCF$_3$ | H | H | H | —(CH$_2$)$_2$—CHOCH$_3$—(CH$_2$)$_2$— | | 228 | β |
| I-a-3 | 5-OCF$_3$ | 2-Br | H | H | —(CH$_2$)$_2$—CHOCH$_3$—(CH$_2$)$_2$— | | 258 | β |
| I-a-4 | 5-OCF$_3$ | 2-Br | H | H | —(CH$_2$)$_2$—O—(CH$_2$)$_2$— | | 138 | — |
| I-a-5 | 5-OCF$_3$ | 2-Br | H | H | —(CH$_2$)$_2$—C(O—)(—O)—(CH$_2$)$_2$— (1,3-dioxolane spiro) | | 230 | — |
| I-a-6 | 5-OCF$_3$ | 2-Br | H | H | —(CH$_2$)$_2$—CHOC$_2$H$_5$—(CH$_2$)$_2$— | | 96 | β |
| I-a-7 | 4-OCF$_3$ | 2-Br | 6-Br | H | —CH$_2$—CHOCH$_3$—(CH$_2$)$_3$— | | 372 | α |
| I-a-8 | 4-OCF$_3$ | 2-Br | 6-CH$_3$ | H | —(CH$_2$)$_2$—O—(CH$_2$)$_2$— | | *1.46-1.57 (m, 2H, CH$_2$); 2.20 (s, 3H, Ar—CH$_3$); 3.73-3.79 (m, 2H, OCH$_2$); 3.99-4.03 (m, 2H, OCH$_2$); 7.42-7.43 (d, 1H, ArH) | |
| I-a-9 | 4-OCF$_3$ | 2-Br | 6-Br | H | —(CH$_2$)$_2$—CHOC$_2$H$_5$—(CH$_2$)$_2$— | | 170 | β |
| I-a-10 | 4-OCF$_3$ | 2-Br | 6-Cl | H | CH$_3$ | CH$_3$ | 108-111 | — |
| I-a-11 | 4-OCF$_3$ | 2-Br | 6-Cl | H | —CH$_2$—CHOC$_4$H$_9$—(CH$_2$)$_3$— | | 110-112 | β |
| I-a-12 | 4-OCF$_3$ | 2-Br | 6-Cl | —(CH$_2$)$_3$— | | H | 220-221 | — |
| I-a-13 | 4-OCF$_3$ | 2-Br | 6-Cl | cyclopropyl | CH$_3$ | H | 100-102 | — |
| I-a-14 | 4-OCF$_3$ | 2-Br | 6-Br | H | —CH$_2$—CHOC$_4$H$_9$—(CH$_2$)$_3$— | | 106-110 | β |
| I-a-15 | 4-OCF$_3$ | 2-Br | 6-Br | —(CH$_2$)$_3$— | | H | 229-231 | — |
| I-a-16 | 4-OCF$_3$ | 2-Br | 6-Br | cyclopropyl | CH$_3$ | H | 108-112 | — |
| I-a-17 | 4-OCF$_3$ | 2-Br | 6-Br | H | cyclopropyl | CH$_3$ | 98-100 | — |
| I-a-18 | 4-OCF$_3$ | 2-Br | 6-Br | H | C$_2$H$_5$ | CH$_3$ | 85-87 | — |
| I-a-19 | 4-OCF$_3$ | 2-Br | 6-Cl | H | cyclopropyl | CH$_3$ | 221-225 | — |
| I-a-20 | 4-OCF$_3$ | 2-Br | 6-Cl | H | C$_2$H$_5$ | CH$_3$ | 209-212 | — |
| I-a-21 | 4-OCF$_3$ | 2-OCH$_3$ | 6-Br | H | CH$_3$ | CH$_3$ | | — |

(I-a)

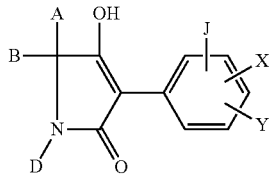

| Ex. No. | J | X | Y | D | A | B | m. p. °C. | Isomer |
|---|---|---|---|---|---|---|---|---|
| I-a-22 | 4-OCF$_3$ | 2-OCH$_3$ | 6-Br | H | —(CH$_2$)$_2$—CHOCH$_3$—(CH$_2$)$_2$— | | 104-106 | β |
| I-a-23 | 4-OCF$_3$ | 2-OCH$_3$ | 6-Cl | H | CH$_3$ | CH$_3$ | 133-136 | — |
| I-a-24 | 4-OCF$_3$ | 2-OCH$_3$ | 6-Cl | H | —CH$_2$—CHOC$_4$H$_9$—(CH$_2$)$_3$— | | 93-96 | β |
| I-a-25 | 4-OCF$_3$ | 2-OCH$_3$ | 6-Cl | | —(CH$_2$)$_3$— | H | 170-172 | — |
| I-a-26 | 4-OCF$_3$ | 2-OCH$_3$ | 6-Cl | H | —(CH$_2$)$_2$—CHOCH$_3$—(CH$_2$)$_2$— | | 170-173 | β |
| I-a-27 | 4-OCF$_3$ | 2-OCH$_3$ | 6-Cl | H | (cyclopropyl) | CH$_3$ | 79-82 | — |
| I-a-28 | 4-OCF$_3$ | 2-OCH$_3$ | 6-Cl | H | —(CH$_2$)$_2$—O—(CH$_2$)$_2$— | | 121 | — |
| I-a-29 | 4-OCF$_3$ | 2-Cl | 6-Cl | H | —(CH$_2$)$_2$—CHOCH$_3$—(CH$_2$)$_2$— | | 282 | β |
| I-a-30 | 4-OCF$_3$ | 2-Cl | 6-Cl | H | —(CH$_2$)$_2$—O—(CH$_2$)$_2$— | | 251 | — |
| I-a-31 | 4-OCF$_3$ | 2-Br | 6-Br | H | CH$_3$ | CH$_3$ | 216 | — |
| I-a-32 | 4-OCF$_3$ | 2-Br | 6-Br | H | —(CH$_2$)$_2$—CHOCH$_3$—(CH$_2$)$_2$— | | 280 | β |
| I-a-33 | 4-OCF$_3$ | 2-Br | 6-Br | H | —CH$_2$—CHOCH$_3$—(CH$_2$)$_3$— | | wax | β |
| I-a-34 | 5-OCF$_3$ | 2-Br | H | H | —CH$_2$—CH(CH$_2$OCH$_3$)—(CH$_2$)$_2$— | | 125 | β |
| I-a-35 | 5-OCF$_3$ | 2-Br | H | H | —(CH$_2$)$_2$—CH(CH$_2$OCH$_3$)—(CH$_2$)$_2$— | | 189 | β |
| I-a-36 | 4-OCF$_3$ | 2-OCH$_3$ | 6-OCH$_3$ | H | —(CH$_2$)$_2$—CHOCH$_3$—(CH$_2$)$_2$— | | ***3.32 (m, 1H, CHOCH$_3$); 6.40 (s, 2H, ArH) | β |
| I-a-37 | 4-OCF$_3$ | 2-CH$_3$ | 6-CH$_3$ | H | —CH$_2$—CHOC$_2$H$_5$—(CH$_2$)$_3$— | | 109-112 | β |
| I-a-38 | 4-OCF$_3$ | 2-CH$_3$ | 6-CH$_3$ | H | —(CH$_2$)$_2$—CHOCH$_3$—(CH$_2$)$_2$— | | 263-265 | β |
| I-a-39 | 4-OCF$_3$ | 2-Cl | 6-CH$_3$ | H | —(CH$_2$)$_2$—CHOCH$_3$—(CH$_2$)$_2$— | | 270 | β |
| I-a-40 | 4-OCF$_3$ | 2-Cl | 6-CH$_3$ | H | —CH$_2$—CHOCH$_3$—(CH$_2$)$_2$— | | 202-206 | cis |
| I-a-41 | 4-OCF$_3$ | 2-Cl | 6-CH$_3$ | H | —CH$_2$—CHOCH$_3$—(CH$_2$)$_2$— | | 75-95 | trans |
| I-a-42 | 4-OCF$_3$ | 2-OCH$_3$ | 6-Cl | H | —(CH$_2$)$_2$—C(OCH$_2$CH$_2$O)—(CH$_2$)$_2$— (spiro dioxolane) | | decomposition | — |
| I-a-43 | 4-OCF$_3$ | 2-Cl | 6-Cl | H | —(CH$_2$)$_2$—C(OCH$_2$CH$_2$O)—(CH$_2$)$_2$— (spiro dioxolane) | | 272 | — |
| I-a-44 | 4-OCF$_3$ | 2-Br | 6-Br | H | —(CH$_2$)$_2$—CH(CH$_2$OCH$_3$)—(CH$_2$)$_2$— | | 240 | β |
| I-a-45 | 4-OCF$_3$ | 2-Br | 6-Br | H | —(CH$_2$)$_2$—C(OCH$_2$CH$_2$O)—(CH$_2$)$_2$— (spiro dioxolane) | | 291 | — |
| I-a-46 | 2-OCF$_3$ | 4-Br | H | H | —(CH$_2$)$_2$—CHOCH$_3$—(CH$_2$)$_2$— | | 253 | β |
| I-a-47 | 2-OCF$_3$ | 4-Cl | H | H | —(CH$_2$)$_2$—O—(CH$_2$)$_2$— | | 245 | — |
| I-a-48 | 2-OCF$_3$ | 6-Cl | 4-Br | H | —(CH$_2$)$_2$—O—(CH$_2$)$_2$— | | 258 | — |
| I-a-49 | 2-OCF$_3$ | 6-CH$_3$ | 4-CH$_3$ | H | —(CH$_2$)$_2$—CHOCH$_3$—(CH$_2$)$_2$— | | 216-219 | β |
| I-a-50 | 2-OCF$_3$ | 6-CH$_3$ | 4-CH$_3$ | H | —CH$_2$—CHOCH$_3$—(CH$_2$)$_2$— | | 189-192 | β |
| I-a-51 | 2-OCF$_3$ | 6-OCH$_3$ | 4-Br | H | —(CH$_2$)$_2$—O—(CH$_2$)$_2$— | | 208 | — |
| I-a-52 | 2-OCF$_3$ | 4-Cl | H | H | —(CH$_2$)$_2$—CHOCH$_3$—(CH$_2$)$_2$— | | 239 | β |
| I-a-53 | 2-OCF$_3$ | 6-Br | 4-Cl | H | —(CH$_2$)$_2$—O—(CH$_2$)$_2$— | | 275 | — |
| I-a-54 | 2-OCF$_3$ | 6-OCH$_3$ | 4-Cl | H | —(CH$_2$)$_2$—O—(CH$_2$)$_2$— | | 224 | — |

-continued (I-a)

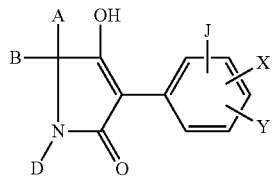

| Ex. No. | J | X | Y | D | A | B | m. p. °C. | Isomer |
|---|---|---|---|---|---|---|---|---|
| I-a-55 | 2-OCF$_3$ | 6-Cl | 4-CH$_3$ | H | —(CH$_2$)$_2$—O—(CH$_2$)$_2$— | | **1.2-1.34 (m, 2H, CH$_2$) - 2.37 (s, 3H-ArCH$_3$ 3.83-3.88 (m, 2H, OCH$_2$), 7.14, 7.34 (2s, 2H, ArH) | — |
| I-a-56 | 2-OCF$_3$ | 4-Br | H | H | —(CH$_2$)$_2$—O—(CH$_2$)$_2$— | | 246 | — |
| I-a-57 | 2-OCF$_3$ | 6-Cl | H | H | —(CH$_2$)$_2$—CHOCH$_3$—(CH$_2$)$_2$— | | 254 | β |
| I-a-58 | 2-OCF$_3$ | 6-Br | 4-Cl | H | —(CH$_2$)$_2$—CHOCH$_3$—(CH$_2$)$_2$— | | 280 | β |
| I-a-59 | 2-OCF$_3$ | 6-Br | 4-Br | H | —(CH$_2$)$_2$—CHOCH$_3$—(CH$_2$)$_2$— | | 280 | β |
| I-a-60 | 2-OCF$_3$ | 6-Cl | 4-Br | H | —CH$_2$—CHOC$_2$H$_5$—(CH$_2$)$_3$— | | 73 | β |
| I-a-61 | 2-OCF$_3$ | 6-OCH$_3$ | 4-Cl | H | —(CH$_2$)$_2$—CHOCH$_3$—(CH$_2$)$_2$— | | 196-198 | β |
| I-a-62 | 2-OCF$_3$ | 6-Cl | 4-CH$_3$ | H | —(CH$_2$)$_2$—CHOCH$_3$—(CH$_2$)$_2$— | | 209-210 | β |
| I-a-63 | 2-OCF$_3$ | 6-Cl | 4-CH$_3$ | H | —CH$_2$—CHOC$_2$H$_5$—(CH$_2$)$_3$— | | 189-192 | β |
| I-a-64 | 2-OCF$_3$ | 6-Cl | 4-CH$_3$ | H | —CH$_2$—CHOC$_3$H$_7$—(CH$_2$)$_3$— | | 105-108 | β |
| I-a-65 | 2-OCF$_3$ | 6-OCH$_3$ | 4-Cl | H | —CH$_2$—CHOC$_2$H$_5$—(CH$_2$)$_3$— | | 89-91 | β |
| I-a-66 | 2-OCF$_3$ | 6-C$_2$H$_5$ | 4-Cl | H | —(CH$_2$)$_2$—CHOCH$_3$—(CH$_2$)$_2$— | | 237-240 | β |
| I-a-67 | 2-OCF$_3$ | 6-C$_2$H$_5$ | 4-Cl | H | —(CH$_2$)$_2$—CH(CH$_2$—OCH$_3$)—(CH$_2$)$_2$— | | 201-204 | β |
| I-a-68 | 2-OCF$_3$ | 6-CH$_3$ | 4-Cl | H | —CH$_2$—CHOC$_2$H$_5$—(CH$_2$)$_3$— | | 222-223 | β |
| I-a-69 | 2-OCF$_3$ | 6-CH$_3$ | 4-Cl | H | —(CH$_2$)$_2$—CHOCH$_3$—(CH$_2$)$_2$— | | 280-282 | β |
| I-a-70 | 2-OCF$_3$ | 6-Cl | 4-Br | H | —(CH$_2$)$_2$—C(OCH$_2$CH$_2$O)—(CH$_2$)$_2$— | | 209 | — |
| I-a-71 | 2-OCF$_3$ | 6-Cl | 4-Br | H | CH$_3$ | CH$_3$ | 181 | — |
| I-a-72 | 2-OCF$_3$ | 6-Cl | 4-Br | H | —(CH$_2$)$_2$—C(OCH$_2$CH$_2$CH$_2$O)—(CH$_2$)$_2$— | | 257 | — |
| I-a-73 | 2-OCF$_3$ | 6-C$_2$H$_5$ | 4-Cl | | —(CH$_2$)$_3$— | H | 217-220 | |

*$^1$H-NMR (400 MHz, d$_4$-methanol): shifts δ in ppm
**$^1$H-NMR (400 MHz, d$_6$-DMSO): shifts δ in ppm
***$^1$H-NMR (400 MHz, CDCl$_3$): shifts δ in ppm Example I-b-1

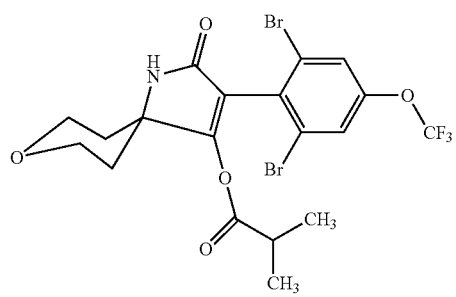 [SMILES: CC(C)C(=O)OC1=C(c2c(Br)cc(OC(F)(F)F)cc2Br)C(=O)NC12CCOCC2]

Under argon, 0.5 g (1 mmol) of the compound according to Ex. I-a-1 are initially charged in ethyl acetate, 0.14 ml of triethylamine plus 10 mg of Steglich base are added and 0.1 ml of 2-methyl-propionyl chloride dissolved in 5 ml of ethyl acetate are added dropwise at reflux, and the mixture is then stirred under reflux.

After the reaction has ended (the reaction is monitored by thin-layer chromatography), the mixture is separated by RP column chromatography (water/acetonitrile:50/50→10/90).

Yield: 0.23 g (40% of theory), m.p. 219° C.

Analogously to Example (I-b-1) and in accordance with the general statements on the preparation, the following compounds of the formula (I-b) are obtained:

(I-b)

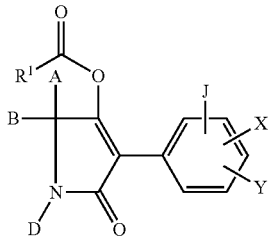

| Ex. No. | J | X | Y | D | A | B | R¹ | m.p. °C. | Isomer |
|---|---|---|---|---|---|---|---|---|---|
| I-b-2 | 5-OCF₃ | 2-Br | H | H | —(CH₂)₂—CHOCH₃—(CH₂)₂— | | i-C₃H₇ | 165 | β |
| I-b-3 | 5-OCF₃ | 2-Br | H | H | —(CH₂)₂—CH(CH₂OCH₃)—(CH₂)₂— | | i-C₃H₇ | 156 | β |
| I-b-4 | 4-OCF₃ | 2-Br | 6-Cl | ▷ | CH₃ | H | i-C₃H₇ | oil, *1) | — |
| I-b-5 | 4-OCF₃ | 2-Br | 6-Br | H | —CH₂—CHOC₄H₉—(CH₂)₃— | | i-C₃H₇ | 182-185 | β |
| I-b-6 | 4-OCF₃ | 2-Br | 6-Cl | H | ▷ | CH₃ | i-C₃H₇ | 156-159 | — |
| I-b-7 | 4-OCF₃ | 2-Br | 6-Br | H | ▷ | CH₃ | i-C₃H₇ | 150-156 | — |
| I-b-8 | 4-OCF₃ | 2-Br | 6-Br | H | C₂H₅ | CH₃ | i-C₃H₇ | 129-132 | — |
| I-b-9 | 4-OCF₃ | 2-Br | 6-Cl | H | —CH₂—CHOC₄H₉—(CH₂)₃— | | i-C₃H₇ | 183-186 | β |
| I-b-10 | 4-OCF₃ | 2-Br | 6-Br | H | —(CH₂)₃— | H | i-C₃H₇ | ** 2) | — |
| I-b-11 | 4-OCF₃ | 2-Br | 6-Cl | ▷ | CH₃ | H | i-C₃H₇ | ** 3) | — |
| I-b-12 | 4-OCF₃ | 2-Br | 6-Cl | H | C₂H₅ | CH₃ | i-C₃H₇ | 135-141 | — |
| I-b-13 | 4-OCF₃ | 2-OCH₃ | 6-Br | H | —(CH₂)₂—CHOCH₃—(CH₂)₂— | | i-C₃H₇ | 204 | β |
| I-b-14 | 4-OCF₃ | 2-Br | 6-Cl | H | —(CH₂)₃— | H | i-C₃H₇ | ** 4) | — |
| I-b-15 | 4-OCF₃ | 2-OCH₃ | 6-Cl | H | —CH₂—CHOC₄H₉—(CH₂)₃— | | i-C₃H₇ | 178-186 | β |
| I-b-16 | 4-OCF₃ | 2-OCH₃ | 6-Cl | H | —(CH₂)₃— | H | i-C₃H₇ | ** 5) | — |
| I-b-17 | 4-OCF₃ | 2-OCH₃ | 6-Cl | H | —(CH₂)₂—CHOCH₃—(CH₂)₂— | | i-C₃H₇ | 198 | β |
| I-b-18 | 4-OCF₃ | 2-OCH₃ | 6-Cl | H | ▷ | CH₃ | i-C₃H₇ | 153-174 | — |
| I-b-19 | 4-OCF₃ | 2-OCH₃ | 6-Cl | H | CH₃ | CH₃ | i-C₃H₇ | 110-118 | — |
| I-b-20 | 4-OCF₃ | 2-Cl | 6-Cl | H | —(CH₂)₂—CHOCH₃—(CH₂)₂— | | i-C₃H₇ | 190 | β |
| I-b-21 | 4-OCF₃ | 2-Cl | 6-CH₃ | H | —(CH₂)₂—CHOCH₃—(CH₂)₂— | | CH₃ | 212 | β |
| I-b-22 | 4-OCF₃ | 2-Cl | 6-CH₃ | H | —(CH₂)₂—CHOCH₃—(CH₂)₂— | | i-C₃H₇ | 159-161 | β |
| I-b-23 | 4-OCF₃ | 2-Br | 6-Br | H | —(CH₂)₂—CH(CH₂OCH₃)—(CH₂)₂— | | i-C₃H₇ | 204 | β |
| I-b-24 | 2-OCF₃ | 6-CH₃ | 4-CH₃ | H | —CH₂—CHOC₂H₅—(CH₂)₃— | | CH₃ | 228-230 | β |
| I-b-25 | 2-OCF₃ | 6-CH₃ | 4-CH₃ | H | —(CH₂)₂—CHOCH₃—(CH₂)₂— | | CH₃ | 202-205 | β |

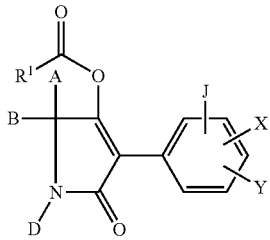

(I-b)

| Ex. No. | J | X | Y | D | A | B | R¹ | m.p. °C | Isomer |
|---|---|---|---|---|---|---|---|---|---|
| I-b-26 | 2-OCF₃ | 6-CH₃ | 4-CH₃ | H | —(CH₂)₂—CHOCH₃—(CH₂)₂— | | i-C₃H₇ | 207 | β |
| I-b-27 | 2-OCF₃ | 6-C₂H₅ | 4-Cl | H | —(CH₂)₂—CH—(CH₂)₂—  \|  CH₂—OCH₃ | | i-C₃H₇ | * 6) | β |
| I-b-28 | 2-OCF₃ | 6-CH₃ | 4-Cl | H | —(CH₂)₂—CHOCH₃—(CH₂)₂— | | CH₃ | * 7) | β |

1) 2.61 (m, 1H, CH (C5)); 2.70 (m, 1H (CH (CH₃)₂); 7.31, 7.44 (in each case dd, 1H, ArH)
2) 2.70 (m, 1H, CH (CH₃)₂); 4.79 (m, 1H, CH(C5)); 7.47 (dd, 2-H, ArH)
3) 2.62 (m, 1H, CH(C5); 2.70 (m, 1H, CH(CH₃)₂); 7.47 (dd, 1H ArH)
4) 2.67 (m, 1H, CH( CH₃)₂; 4.75 (m, 1H, CH(C5); 7.31, 7.43 (in each case dd, 1H, ArH)
5) 2.66 (m, 1H, CH (CH₃)₂; 4.70 (m, 1H, CH(C5); 6.68, 6.96 (in each case dd, 1H, ArH)
6) 2.62 (m, 1H, CH(CH₃)₂); 2.71 (m, 2H, Ar CH₂(CH₃); 3.36 (s, 3H, OCH₃)
7) 2.1 (s, 3H, COCH₃); 2.33 (s, 3H, ArCH₃); 3.40 (s, 3H, OCH₃)
*¹H-NMR (400 MHz, CDCl₃): shift δ in ppm
**¹H-NMR (300 MHz, CDCl₃): shift δ in ppm Example I-c-1

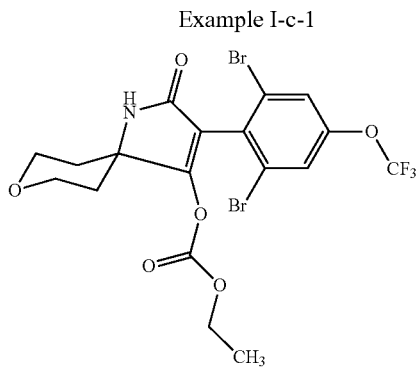

Under argon, 0.5 g (1 mmol) of the compound according to Ex. I-a-1 is initially charged in methylene chloride, 0.14 ml of triethylamine is added, at about 20° C. the chloroformic ester (0.1 ml), dissolved in 5 ml of dichloromethane, is added dropwise and the mixture is stirred at from 20 to 30° C.

After the reaction has ended (the reaction is monitored by thin-layer chromatography), the mixture is separated by RP column chromatography (water/acetonitrile:50/50→10/90).

Yield: 0.415 g (74% of theory), m.p. 194° C.

Analogously to Example (I-c-1) and in accordance with the general statements on the preparation, the following compounds of the formula (I-c) are obtained:

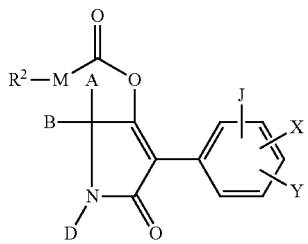

(I-c)

| Ex. No. | J | X | Y | D | A | B | M | R² | m.p. °C | Isomer |
|---|---|---|---|---|---|---|---|---|---|---|
| I-c-2 | 5-OCF₃ | 2-Br | H | H | —(CH₂)₂—CHOCH₃—(CH₂)₂— | | O | C₂H₅ | 161 | β |
| I-c-3 | 5-OCF₃ | 2-Br | H | H | —(CH₂)₂—C(O-CH₂-CH₂-O)—(CH₂)₂— | | O | C₂H₅ | 201 | — |

-continued

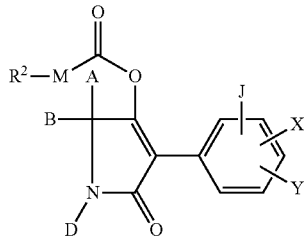

(I-c)

| Ex. No. | J | X | Y | D | A | B | M | R² | m.p. °C. | Isomer |
|---|---|---|---|---|---|---|---|---|---|---|
| I-c-4 | 5-OCF₃ | 2-Br | H | H | —(CH₂)₂—CH(CH₂OCH₃)—(CH₂)₂— | | O | C₂H₅ | 182 | β |
| I-c-5 | 4-OCF₃ | 2-Br | 6-Br | H | —(CH₂)₂—CHOCH₃—(CH₂)₂— | | O | C₂H₅ | 166 | β |
| I-c-6 | 4-OCF₃ | 2-Br | 6-Cl | H | —CH₂—CHOC₄H₉—(CH₂)₃— | | O | C₂H₅ | 184 | β |
| I-c-7 | 4-OCF₃ | 2-Br | 6-Cl | H | —(CH₂)₃— | H | O | C₂H₅ | * 1) | — |
| I-c-8 | 4-OCF₃ | 2-Br | 6-Cl | ▷ | CH₃ | H | O | C₂H₅ | viscous oil * 2) | — |
| I-c-9 | 4-OCF₃ | 2-Br | 6-Br | H | —CH₂—CHOC₄H₉—(CH₂)₃— | | O | C₂H₅ | 201 | β |
| I-c-10 | 4-OCF₃ | 2-Br | 6-Br | H | —(CH₂)₃— | H | O | C₂H₅ | viscous oil * 3) | — |
| I-c-11 | 4-OCF₃ | 2-Br | 6-Br | ▷ | CH₃ | H | O | C₂H₅ | viscous oil * 4) | — |
| I-c-12 | 4-OCF₃ | 2-Br | 6-Cl | H | ▷ | CH₃ | O | C₂H₅ | 143 | — |
| I-c-13 | 4-OCF₃ | 2-Br | 6-Br | H | ▷ | CH₃ | O | C₂H₅ | 126-130 | — |
| I-c-14 | 4-OCF₃ | 2-Br | 6-Br | H | C₂H₅ | CH₃ | O | C₂H₅ | 110-114 | — |
| I-c-15 | 4-OCF₃ | 2-Br | 6-Cl | H | C₂H₅ | CH₃ | O | C₂H₅ | 130-131 | — |
| I-c-16 | 4-OCF₃ | 2-OCH₃ | 6-Br | H | —(CH₂)₂—CHOCH₃—(CH₂)₂— | | O | C₂H₅ | 177-179 | β |
| I-c-17 | 4-OCF₃ | 2-OCH₃ | 6-Cl | H | —CH₂—CHOC₄H₉—(CH₂)₃— | | O | C₂H₅ | 188-190 | β |
| I-c-18 | 4-OCF₃ | 2-OCH₃ | 6-Cl | H | —(CH₂)₂—CHOCH₃—(CH₂)₂— | | O | C₂H₅ | 147-150 | β |
| I-c-19 | 4-OCF₃ | 2-OCH₃ | 6-Cl | H | —(CH₂)₃— | H | O | C₂H₅ | *1.30 (m, 3H, O—CH, CH₃), 4.67 (m, 1H, 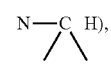 N—CH), 6.52, 6.92 (2d, in each case 1H, Ar—H) | — |
| I-c-20 | 4-OCF₃ | 2-Cl | 6-Cl | H | —(CH₂)₂—CHOCH₃—(CH₂)₂— | | O | C₂H₅ | 164 | β |
| I-c-21 | 4-OCF₃ | 2-Cl | 6-Cl | H | —(CH₂)₂—O—(CH₂)₂— | | O | C₂H₅ | 212 | — |
| I-c-22 | 4-OCF₃ | 2-CH₃ | 6-CH₃ | H | —(CH₂)₂—CHOCH₃—(CH₂)₂— | | O | C₂H₅ | 182-183 | β |
| I-c-23 | 4-OCF₃ | 2-CH₃ | 6-CH₃ | H | —CH₂—CHOC₂H₅—(CH₂)₃— | | O | C₂H₅ | 205-206 | β |
| I-c-24 | 4-OCF₃ | 2-Cl | 6-CH₃ | H | —CH₂—CHOCH₃—(CH₂)₂— | | O | C₂H₅ | 86-89 | cis |

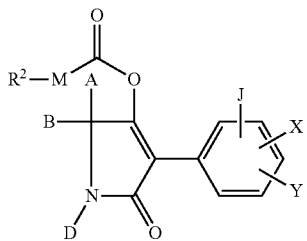

(I-c)

| Ex. No. | J | X | Y | D | A | B | M | R² | m.p. °C | Isomer |
|---|---|---|---|---|---|---|---|---|---|---|
| I-c-25 | 4-OCF₃ | 2-Cl | 6-CH₃ | H | —CH₂—CHOCH₃—(CH₂)₂— | | O | C₂H₅ | 146-149 | trans |
| I-c-26 | 4-OCF₃ | 2-Cl | 6-CH₃ | H | —(CH₂)₂—CHOCH₃—(CH₂)₂— | | O | C₂H₅ | 163-165 | β |
| I-c-27 | 4-OCF₃ | 2-Br | 6-Br | H | —(CH₂)₂—CH(CH₂OCH₃)—(CH₂)₂— | | O | C₂H₅ | 201 | β |
| I-c-28 | 2-OCF₃ | 6-C₂H₅ | 4-Cl | | —(CH₂)₃— | H | O | CH₂—C₆H₅ | * 5) | — |
| I-c-29 | 2-OCF₃ | 6-CH₃ | 4-CH₃ | H | —(CH₂)₂—CHOCH₃—(CH₂)₂— | | O | C₂H₅ | 210-212 | β |
| I-c-30 | 2-OCF₃ | 6-CH₃ | 4-CH₃ | H | —CH₂—CHOC₂H₅—(CH₂)₃— | | O | C₂H₅ | 203 | β |
| I-c-31 | 2-OCF₃ | 6-OCH₃ | 4-Cl | H | —(CH₂)₂—CHOCH₃—(CH₂)₂— | | O | C₂H₅ | 168-170 | β |
| I-c-32 | 2-OCF₃ | 6-C₂H₅ | 4-Cl | H | —(CH₂)₂—CHOCH₃—(CH₂)₂— | | O | C₂H₅ | 139-141 | β |
| I-c-33 | 2-OCF₃ | 6-C₂H₅ | 4-Cl | H | —(CH₂)₂—CH(CH₂OCH₃)—(CH₂)₂— | | O | C₂H₅ | 160-162 | β |
| I-c-34 | 2-OCF₃ | 6-CH₃ | 4-Cl | H | —CH₂—CHOC₂H₅—(CH₂)₃— | | O | C₂H₅ | 186-188 | β |
| I-c-35 | 2-OCF₃ | 6-OCH₃ | 4-Cl | H | —CH₂—CHOC₂H₅—(CH₂)₃— | | O | C₂H₅ | 186-187 | β |
| I-c-36 | 2-OCF₃ | 6-Cl | 4-CH₃ | H | —(CH₂)₂—CHOCH₃—(CH₂)₂— | | O | C₂H₅ | 227-228 | β |
| I-c-37 | 2-OCF₃ | 6-Cl | 4-CH₃ | H | —CH₂—CHOC₂H₅—(CH₂)₃— | | O | C₂H₅ | 144-145 | β |
| I-c-38 | 2-OCF₃ | 6-CH₃ | 4-Cl | H | —(CH₂)₂—CHOCH₃—(CH₂)₂— | | O | C₂H₅ | * 6 | β |
| I-c-39 | 2-OCF₃ | 6-C₂H₅ | 4-Cl | H | —(CH₂)₂—CHOCH₃—(CH₂)₂— | | O | CH₃ | * 7 | β |

1) 4.29 (m, 2H, OCH₂—CH₃); 4.81 (m, 1H, CH (C5)); 7.33, 7.47 (in each case dd, 1H, ArH)

2) 2.62 (m, 1H, CH (C5)); 4.26 (m, 2H, OCH₂CH₃); 7.32, 7.45 (in each case dd, 1H, ArH)

3) 4.27 (q, 2H, OCH₂); 4.80 (m, 1H, CH (C5);7.47 (dd, 2H, ArH)

4) 2.62 (m, 1H, CH (C5); 4.26 (m, 2H, OCH₂); 7.47 (d, 2H, ArH)

5) 1.08 (m, 3H, Ar—CH₂—CH₃); 4.76 (m, 1H, CH (C5); 5.2 (d, 2H, O—CH₂)

6) 2.33 (s, 3H, Ar CH₃); 3.38 (s, 3H, OCH₃); 4.08 (q, 2 H, OCH₂)

7) 2.67 (m, 2H, Ar—CH₂—CH₃); 3.37 (s, 3H, OCH₃); 3.69 (s, 3H CO₂CH₃)

*¹H-NMR (400 MHz, CDCl₃): shift δ in ppm

**¹H-NMR (300 MHz, CDCl₃): shift δ in ppm:

Example I-d-1

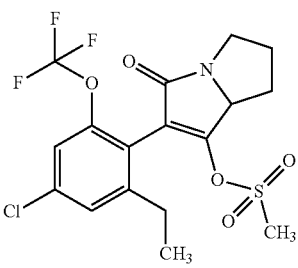 [SMILES: CCc1cc(Cl)cc(OC(F)(F)F)c1C1=C(OS(C)(=O)=O)C2CCCN2C1=O]

0.15 g (0.41 mmol) of the compound according to Example (I-a-73), 0.05 g of triethylamine and mg of 4-N,N'-dimethylaminopyridine are initially charged in 5 ml of chloroform. After 10 min of stirring, 0.05 g (0.45 mmol) of methanesulphonyl chloride are added, and the mixture is stirred further at room temperature overnight. The mixture is added to 5 ml of 5% strength sodium bicarbonate solution and stirred at room temperature for 10 min, and the organic phase is separated off, dried over sodium sulphate and concentrated using a rotary evaporator. This is followed by chromatographic purification on silica gel on a Biotage separating unit using a gradient (ethyl acetate:n-heptane 1:4 to 4:1). Yield: 0.052 g (28% of theory)

$^1$H-NMR (300 MHz, CDCl$_3$): δ=3.04 (s, 3H, SOCH$_3$), 4.64 (m, 1H, CH(C5), 7.16, 7.22 (in each case dd, 1H, Ar—H) ppm.

Example I-f-1

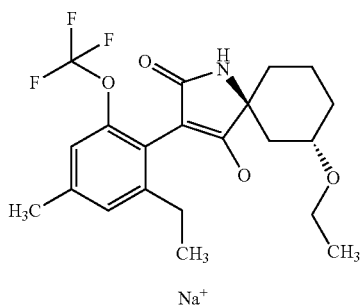 [SMILES: CCO[C@H]1CCC[C@@]2(C1)NC(=O)C(c1c(CC)cc(C)cc1OC(F)(F)F)=C2O ; [Na+]]

0.15 g (0.38 mmol) of the compound according to Example (I-a-50) are initially charged in 6 ml of methanol, and 0.07 ml of a 30% strength sodium methoxide solution is added. After 2 h of stirring at room temperature, the mixture is concentrated and the residue is dried under high vacuum. This gives 0.155 g (=97% of theory) of a solid.

$^1$H-NMR (400 MHz, D$_2$O): δ=3.67 (m, 3H, O—CH and O—CH$_2$), 7.05, 7.13 (in each case d, 1H, ArH) ppm.

Analogously to Example (I-f-1) and in accordance with the general statements on the preparation, the following compounds of the formula (I-f) are obtained:

(I-f)

| Ex.-No. | J | X | Y | D | A | B | E | NMR | Isomer |
|---|---|---|---|---|---|---|---|---|---|
| I-f-2 | 2-OCF$_3$ | 6-C$_2$H$_5$ | 4-Cl | H | —(CH$_2$)$_2$—CHOCH$_3$—(CH$_2$)$_2$— | | Na$^+$ | *1) | β |
| I-f-3 | 2-OCF$_3$ | 4-CH$_3$ | 6-CH$_3$ | H | —(CH$_2$)$_2$—CHOCH$_3$—(CH$_2$)$_2$— | | Na$^+$ | *2) | β |

1) 3.23 (s, 3H, OCH$_3$); 6.98, 7.11 (in each case d, 1H, ArH)
2) 3.16 (s, 3H, OCH$_3$); 6.72, 7.85 (in each case d, 1H, Ar—H)
*$^1$H-NMR (400 MHz, d$_6$-DMSO): shift δ in ppm

Example II-1

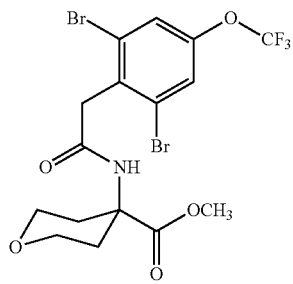 [SMILES: COC(=O)C1(NC(=O)Cc2c(Br)cc(OC(F)(F)F)cc2Br)CCOCC1]

Under argon, 4.3 g (22 mmol) of methyl 1-aminotetrahydropyranylcarboxylate×HCl are initially charged in 40 ml of anhydrous tetrahydrofuran, and 6.2 ml (44 mmol) of triethylamine are added. The mixture is stirred for 5 min, and 7.6 g of 2,6-dibromo-4-trifluoromethoxyphenylacetic acid are added, the mixture is stirred at room temperature for another 15 min, 4.4 ml of triethylamine are added and 1.2 ml of phosphorus oxychloride are immediately added dropwise such that the solution is boiling gently. The mixture is stirred under reflux for 30 min. The reaction mixture is concentrated under reduced pressure and the residue is purified by column chromatography on silica gel (dichloromethane/ethyl acetate=3:1).

Yield: 8.5 g (79% of theory), m.p.: 212° C.

Example II-19

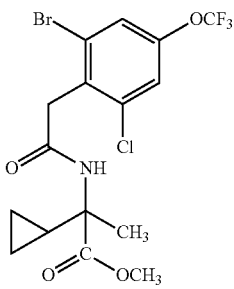 [SMILES: COC(=O)C(C)(NC(=O)Cc1c(Cl)cc(OC(F)(F)F)cc1Br)C1CC1]

3.46 g (8.13 mmol) of the compound according to Example XIX-1 in 10 ml of dichloromethane are added to 2.513 ml of sulphuric acid. The mixture is stirred at 35° C. for 3 h, and 20 ml of methanol are added. The mixture is stirred at 60° for 4 h and then stirred at room temperature overnight. A further 2 ml of sulphuric acid are added, since there is still some starting material left. The mixture is stirred at 60° C. for 4 h. The mixture is checked for conversion by thin-layer chromatography, the reaction solution is then added to 100 ml of water and the organic phase is separated off and dried over sodium sulphate. The solvent is then removed on a rotary evaporator.

Yield: 3.31 g (88% of theory)

Analogously to Examples (II-1) and (II-19) and according to the general statements on the preparation, the following compounds of the formula (II) are obtained:

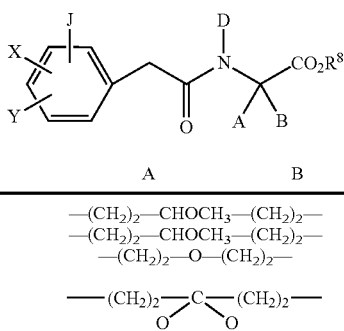

(II)

| Ex. No. | J | X | Y | D | A | B | $R^8$ | m.p. ° C. | Isomer |
|---|---|---|---|---|---|---|---|---|---|
| II-2 | 2-OCF$_3$ | H | H | H | —(CH$_2$)$_2$—CHOCH$_3$—(CH$_2$)$_2$— | | CH$_3$ | 105 | β |
| II-3 | 5-OCF$_3$ | 2-Br | H | H | —(CH$_2$)$_2$—CHOCH$_3$—(CH$_2$)$_2$— | | CH$_3$ | oil | β |
| II-4 | 5-OCF$_3$ | 2-Br | H | H | —(CH$_2$)$_2$—O—(CH$_2$)$_2$— | | CH$_3$ | 125 | — |
| II-5 | 5-OCF$_3$ | 2-Br | H | H | —(CH$_2$)$_2$—C(OCH$_2$CH$_2$O)—(CH$_2$)$_2$— | | CH$_3$ | 138 | — |
| II-6 | 5-OCF$_3$ | 2-Br | H | H | —(CH$_2$)$_2$—CHOC$_2$H$_5$—(CH$_2$)$_2$— | | CH$_3$ | 100 | β |
| II-7 | 4-OCF$_3$ | 2-Br | 6-Br | H | —CH$_2$—CHOCH$_3$—(CH$_2$)$_3$— | | CH$_3$ | 102 | β |
| II-8 | 5-OCF$_3$ | 2-Br | H | H | —(CH$_2$)$_2$—CH(CH$_2$—OCH$_3$)—(CH$_2$)$_2$— | | CH$_3$ | Wax | β |
| II-9 | 4-OCF$_3$ | 2-Br | 6-Br | H | —(CH$_2$)$_2$—CHOC$_2$H$_5$—(CH$_2$)$_2$— | | CH$_3$ | 186 | β |
| II-10 | 4-OCF$_3$ | 2-Br | 6-Cl | H | CH$_3$ | CH$_3$ | CH$_3$ | 127-129 | — |
| II-11 | 4-OCF$_3$ | 2-Br | 6-Cl | H | —CH$_2$—CHOC$_4$H$_9$—(CH$_2$)$_3$— | | CH$_3$ | *0.89 (t, 3H, CH$_3$), 3.97 (d, 2H, Ar—CH$_2$), 7.32 and 7.44 (in each case s, 1H, Ar—H) | trans |
| II-12 | 4-OCF$_3$ | 2-Br | 6-Cl | | —(CH$_2$)$_3$— | H | CH$_3$ | *4.02 (d, 2H, Ar—CH$_2$) 7.26 and 7.38 (in each case s, 1H, Ar—H), 4.53 (m, 1H, C(2)-H) | — |
| II-13 | 4-OCF$_3$ | 2-Br | 6-Cl | cyclopropyl | CH$_3$ | H | CH$_3$ | *1.51 (d, 3H, CH$_3$) 4.24 (s, 2H, Ar—CH$_2$) 7.26 and 7.38 (in each case s, 1H, Ar—H) | — |
| II-14 | 4-OCF$_3$ | 2-Br | 6-Br | H | —CH$_2$—CHOC$_4$H$_9$—(CH$_2$)$_3$— | | CH$_3$ | *0.91 (t, 3H, CH$_3$) 4.03 (s, 2H, Ar—CH$_2$) 7.51 (s, 2H, Ar—H) | β |
| II-15 | 4-OCF3 | 2-Br | 6-Br | | —(CH$_2$)$_3$— | H | CH$_3$ | *4.53 (m, 1H, C(2)-H, 4.09 (d, 2H, Ar—CH$_2$) 7.44 (s, 2H, Ar—H) | — |
| II-16 | 4-OCF$_3$ | 2-Br | 6-Br | cyclopropyl | CH$_3$ | H | CH$_3$ | *1.51 (d, 3H, CH$_3$) 4.31 (s, 2H, Ar—CH$_2$) 7.44 (s, 2H, Ar—H) | — |
| II-17 | 4-OCF$_3$ | 2-Br | 6-Br | H | cyclopropyl | CH$_3$ | CH$_3$ | **1.29 (m, 1H, CH-cyclopropyl), 3.98 (d, 2H, Ar—CH$_2$) 7.47 (s, 2H, Ar—H) | — |

-continued

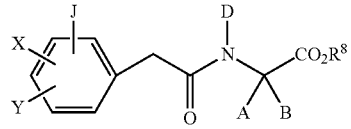

(II)

| Ex. No. | J | X | Y | D | A | B | R⁸ | m.p. ° C. | Isomer |
|---|---|---|---|---|---|---|---|---|---|
| II-18 | 4-OCF₃ | 2-Br | 6-Br | H | C₂H₅ | CH₃ | CH₃ | **1.60 (s, 3H, CH₃—) 4.01 (d, 2H, Ar—CH₂) 7.47 (s, 2H, Ar—H) | — |
| II-19 | 4-OCF₃ | 2-Br | 6-Cl | H | ▷— | CH₃ | CH₃ | **1.46 (s, 3H, CH₃)—, 3.94 (d, 2H, Ar—CH₂) 7.30 and 7.43 (in each case s, 1H, Ar—H) | — |
| II-20 | 4-OCF₃ | 2-Br | 6-Cl | H | C₂H₅ | CH₃ | CH₃ | **1.59 (s, 3H, CH₃) 3.97 (d, 2H, Ar—CH₂) 7.30 and 7.43 (in each case s, 1H, Ar—H) | — |
| II-21 | 4-OCF₃ | 2-OCH₃ | 6-Br | H | CH₃ | CH₃ | CH₃ | 110° C. | — |
| II-22 | 4-OCF₃ | 2-OCH₃ | 6-Br | H | —(CH₂)₂—CHOCH₃—(CH₂)₂— | | CH₃ | **3.33 (s, 3H, CH—OCH₃) 6.72 and 7.11 (in each case s, 1H, Ar—H) | β |
| II-23 | 5-OCF₃ | 2-Br | H | H | —CH₂—CH—(CH₂)₃— \| CH₂—OCH₃ | | CH₃ | 117 | β |
| II-24 | 4-OCF₃ | 2-OCH₃ | 6-Cl | H | —CH₂—CHOC₄H₉—(CH₂)₃— | | CH₃ | **0.93 (t, 3H, CH₃) 3.91 (d, 2H, Ar—CH₂) 6.71 and 6.98 (in each case s, 1H, Ar—H) | β |
| II-25 | 4-OCF₃ | 2-OCH₃ | 6-Cl | H | —(CH₂)₃— | H | CH₃ | **3.68 (s, 3H, Ar—OCH₃) 4.53 (m, 1H, C(2)-H) 6.63 and 6.91 (in each case s, 1H, Ar—H) | — |
| II-26 | 4-OCF₃ | 2-OCH₃ | 6-Cl | H | —(CH₂)₂—CHOCH₃—(CH₂)₂— | | CH₃ | **3.33 (s, 3H, CH—OCH₃) 6.84 and 6.96 (s, 1H, Ar—H) | β |
| II-27 | 4-OCF₃ | 2-OCH₃ | 6-Cl | H | —(CH₂)₂—O—(CH₂)₂— | | CH₃ | 170 | — |
| II-28 | 4-OCF₃ | 2-Cl | 6-Cl | H | —(CH₂)₂—CHOCH₃—(CH₂)₂— | | CH₃ | 168 | β |
| II-29 | 4-OCF₃ | 2-Cl | 6-Cl | H | —(CH₂)₂—O—(CH₂)₂— | | CH₃ | 182 | — |
| II-30 | 4-OCF₃ | 2-Br | 6-Br | H | CH₃ | CH₃ | CH₃ | 170 | — |
| II-31 | 4-OCF₃ | 2-Br | 6-Br | H | —(CH₂)₂—CHOCH₃—(CH₂)₂— | | CH₃ | 180 | β |
| II-32 | 4-OCF₃ | 2-Br | 6-Br | H | —CH₂—CHOCH₃—(CH₂)₃— | | CH₃ | oil | α |
| II-34 | 4-OCF₃ | 2-OCH₃ | 6-OCH₃ | H | —(CH₂)₂—CHOCH₃—(CH₂)₂— | | CH₃ | 137-139 | β |
| II-35 | 4-OCF₃ | 2-CH₃ | 6-CH₃ | H | —(CH₂)₂—CHOCH₃—(CH₂)₂— | | CH₃ | 164-168 | β |
| II-36 | 4-OCF₃ | 2-CH₃ | 6-CH₃ | H | —CH₂—CHOC₂H₅—(CH₂)₃— | | CH₃ | 141-144 | β |
| II-37 | 4-OCF₃ | 2-Cl | 6-CH₃ | H | —CH₂—CHOCH₃—(CH₂)₂— | | C₂H₅ | ** 1) | mixture about 1:1 |
| II-38 | 4-OCF₃ | 2-Cl | 6-CH₃ | H | —(CH₂)₂—CHOCH₃—(CH₂)₂— | | CH₃ | 164 | β |
| II-39 | 4-OCF₃ | 2-Br | 6-Br | H | —(CH₂)₂—C(OCH₂CH₂O)—(CH₂)₂— | | CH₃ | 180 | — |
| II-40 | 4-OCF₃ | 2-OCH₃ | 6-Cl | H | —(CH₂)₂—C(OCH₂CH₂O)—(CH₂)₂— | | CH₃ | 143 | — |
| II-41 | 4-OCF₃ | 2-Cl | 6-Cl | H | —(CH₂)₂—C(OCH₂CH₂O)—(CH₂)₂— | | CH₃ | 160 | — |
| II-42 | 4-OCF₃ | 2-Br | 6-Br | H | —(CH₂)₂—CH—(CH₂)₂— \| CH₂—OCH₃ | | CH₃ | 173 | β |
| II-43 | 2-OCF₃ | 4-Br | H | H | —(CH₂)₂—CHOCH₃—(CH₂)₂— | | CH₃ | 134 | β |
| II-44 | 2-OCF₃ | 4-Cl | H | H | —(CH₂)₂—O—(CH₂)₂— | | CH₃ | 132 | — |

(II)

Structure: Aryl group with substituents X, Y, J connected via CH2-C(=O)-N(D)-C(A)(B)-CO2R8

| Ex. No. | J | X | Y | D | A | B | R⁸ | m.p. °C. | Isomer |
|---|---|---|---|---|---|---|---|---|---|
| II-45 | 2-OCF₃ | 6-Cl | 4-Br | H | —(CH₂)₂—O—(CH₂)₂— | | CH₃ | 144 | — |
| II-46 | 2-OCF₃ | 4-Cl | H | H | —(CH₂)₂—CHOCH₃—(CH₂)₂— | | CH₃ | 133 | β |
| II-47 | 2-OCF₃ | 6-CH₃ | 4-CH₃ | H | —(CH₂)₂—CHOCH₃—(CH₂)₂— | | CH₃ | 138 | β |
| II-48 | 2-OCF₃ | 6-CH₃ | 4-CH₃ | H | —CH₂—(CHOC₂H₅—(CH₂)₃— | | CH₃ | ** 2) | β |
| II-49 | 2-OCF₃ | 4-Br | H | H | —(CH₂)₂O—(CH₂)₂— | | CH₃ | 142 | — |
| II-50 | 2-OCF₃ | 6-OCH₃ | 4-Br | H | —(CH₂)₂—O—(CH₂)₂— | | CH₃ | 182 | — |
| II-51 | 2-OCF₃ | 6-Br | 4-Cl | H | —(CH₂)₂—O—(CH₂)₂— | | CH₃ | 160 | — |
| II-52 | 2-OCF₃ | 6-OCH₃ | 4-Cl | H | —(CH₂)₂—O—(CH₂)₂— | | CH₃ | 181 | — |
| II-53 | 2-OCF₃ | 6-Cl | 4-Br | H | —(CH₂)₂—CHOCH₃—(CH₂)₂— | | CH₃ | 131 | β |
| II-54 | 2-OCF₃ | 6-Cl | 4-Br | H | —CH₂—CHOC₂H₅—(CH₂)₃— | | CH₃ | 128 | β |
| II-55 | 2-OCF₃ | 6-Br | 4-Cl | H | —(CH₂)₂—CHOCH₃—(CH₂)₂— | | CH₃ | 144 | β |
| II-56 | 2-OCF₃ | 6-Br | 4-Br | H | —(CH₂)₂—CHOCH₃—(CH₂)₂— | | CH₃ | 138 | β |
| II-57 | 2-OCF₃ | 6-Cl | 4-Br | H | —(CH₂)₂—C(OCH₂CH₂O)—(CH₂)₂— (dioxolane) | | CH₃ | 155 | — |
| II-58 | 2-OCF₃ | 6-Cl | 4-Br | H | CH₃ | CH₃ | CH₃ | 129 | — |
| II-59 | 2-OCF₃ | 6-OCH₃ | 4-Cl | H | —(CH₂)₂—CHOCH₃—(CH₂)₂— | | CH₃ | ** 3 | β |
| II-60 | 2-OCF₃ | 6-Cl | 4-CH₃ | H | —(CH₂)₂—CHOCH₃—(CH₂)₂— | | CH₃ | 150-151 | β |
| II-61 | 2-OCF₃ | 6-Cl | 4-CH₃ | H | —CH₂—CHOC₂H₅—(CH₂)₃— | | CH₃ | 120-123 | β |
| II-62 | 2-OCF₃ | 6-Cl | 4-CH₃ | H | —CH₂—CHOC₃H₇—(CH₂)₃— | | CH₃ | *** 4 | β |
| II-63 | 2-OCF₃ | 6-CH₃ | 4-Cl | H | —CH₂—CHOC₂H₅—(CH₂)₃— | | CH₃ | *** 5 | β |
| II-64 | 2-OCF₃ | 6-OCH₃ | 4-Cl | H | —CH₂—CHOC₂H₅—(CH₂)₃— | | CH₃ | ** 6 | β |
| II-65 | 2-OCF₃ | 6-C₂H₅ | 4-Cl | H | —(CH₂)₂—CHOCH₃—(CH₂)₂— | | CH₃ | ** 7 | β |
| II-66 | 2-OCF₃ | 6-C₂H₅ | 4-Cl | H | —(CH₂)₂—CH(CH₂—OCH₃)—(CH₂)₂— | | CH₃ | ** 8 | β |

1) 3.11, 3.29 (in each case s, together 3H, OCH₃); 4.16 (m, 2H, OCH₂CH₃)
2) 3.08 (m, 1H, OCH); 3.63(s, 2H, CH₂); 3.68(s, 3H, OCH₃)
3) 3.19 (m, 1H, OCH); 3.68(s, 3H, OCH₃); 3.90(s, 3H, Ar OCH₃)
4) 3.21(m, 1H, OCH); 3.68(s, 3H, OCH₃); 3.76(s, 2H, CH₂)
5) 3.11 (m, 1H, OCH); 3.62(s, 3H, OCH₃); 3.76(s, 2H, CH₂)
6) 3.15 (m, 1H, OCH); 3.60(s, 2H, CH₂); 3.67(s, 3H, OCH₃)
7) 3.15(m, 1H, OCH); 3.63(s, 2H, CH₂); 3.66(s, 3H, OCH₃)
8) 3.31(s, 3H, CH₂—OCH₃); 3.63(s, 2H, CH₂); 3.66(s, 3H, OCH₃)
*¹H-NMR (500 MHz, CDCl₃): shifts δ in ppm
**¹H-NMR (400 MHz, CDCl₃): shifts δ in ppm
***¹H-NMR (300 MHz, CDCl₃): shifts δ in ppm

Example XIX-1

(XIX-1)

3 g (9 mmol) of the compound according to Ex. XVII-2 are initially charged, 1 drop of DMF is added, 3.21 g (27 mmol) of thionyl chloride are added. The mixture is stirred until the evolution of gas has ceased, the SOCl₂ is removed on a rotary evaporator, the residue is taken up in 3 ml of dichloromethane (=solution 1).

2.62 ml of triethylamine are initially charged in 10 ml of dichloromethane, solution 1 is slowly added dropwise at 0° C. The mixture is stirred overnight at room temperature until all the starting material has been consumed, 10 ml of water are added, the mixture is stirred at room temperature for 10 min and then extracted, the organic phase is dried over sodium sulphate and concentrated using a rotary evaporator.

The product is reacted further without purification.

Yield: 3.46 g (90% of theory)

1.79 (s 3H, CH₃)

3.98 (s, 2H, Ar—CH₂)

7.32 and 7.44 (in each case s, 1H, Ar—H)

*¹H-NMR (500 MHz, CDCl₃) shift δ in ppm.

Analogously to Example (XIX-1) and according to the general statements on the preparation, the following compounds of the formula (XIX) are obtained:

(XIX)

| Ex. No. | J | X | Y | A | B | m.p. °C. |
|---|---|---|---|---|---|---|
| XIX-2 | 4-OCF$_3$ | 2-Br | 6-Cl | C$_2$H$_5$ | CH$_3$ | *1.67 (s, 3H, CH$_3$) 3.97 (s, 2H, Ar—CH$_2$) 7.31 and 7.43 (in each case s, 1H, Ar—H) |
| XIX-3 | 4-OCF$_3$ | 2-Br | 6-Br | ▷ | CH$_3$ | *1.80 (s, 3H, CH$_3$) 4.02 (s, 2H, Ar—CH$_2$) 7.49 (s, 2H, Ar—H) |
| XIX-4 | 4-OCF$_3$ | 2-Br | 6-Br | C$_2$H$_5$ | CH$_3$ | 130-132 | where D = H
*$^1$H-NMR (500 MHz, CDCl$_3$) shift δ in ppm.

Example XVII-1

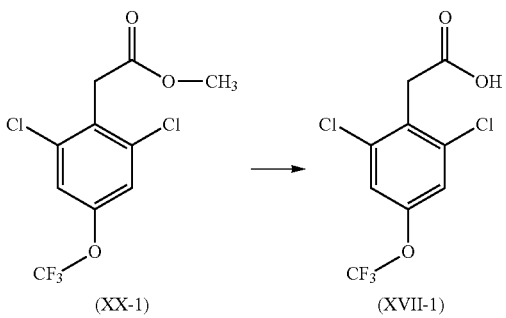

465 g (1.53 mol) of the compound according to Ex. No. XX-1 are initially charged in 10% strength NaOH (1795.87 g=4.49 mmol) at room temperature, and heated to 40° C. The mixture is stirred at 40° C. (the reaction is monitored by thin-layer chromatography). After the reaction has ended, 250 ml of dichloromethane are added, the organic phase is removed, the aqueous phase is acidified with conc. HCl and the precipitate is filtered off with suction.

Yield: 278 g (59% of theory)

Analogously to Example (XVII-1) and according to the general statements on the preparation, the following compounds of the formula (XVII) are obtained:

(XVII)

| Ex. No. | J | X | Y | m.p. °C. |
|---|---|---|---|---|
| XVII-2 | 4-OCF$_3$ | 2-Br | 6-Cl | 144-145 |
| XVII-3 | 4-OCF$_3$ | 2-Br | 6-Br | 165-166 |
| XVII-4 | 4-OCF$_3$ | 2-OCH$_3$ | 6-Br | 149-150 |
| XVII-5 | 4-OCF$_3$ | 2-OCH$_3$ | 6-Cl | 135-137 |
| XVII-6 | 4-OCF$_3$ | 2-Cl | 6-Cl | 124 |
| XVII-7 | 4-OCF$_3$ | 2-OCH$_3$ | 6-Cl | 136-137 |
| XVII-8 | 4-OCF$_3$ | 2-OCH$_3$ | 6-Br | 148-149 |
| XVII-9 | 4-OCF$_3$ | 2-CH$_3$ | 6-CH$_3$ | 144-147 |
| XVII-10 | 4-OCF$_3$ | 2-Cl | 6-CH$_3$ | 116-120 |
| XVII-11 | 2-OCF$_3$ | 2-Cl | 4-Br | 130 |
| XVII-12 | 2-OCF$_3$ | 6-CH$_3$ | 4-CH$_3$ | 140 |
| XVII-13 | 2-OCF$_3$ | 6-OCH$_3$ | 4-Cl | 138-140 |
| XVII-14 | 2-OCF$_3$ | 6-Cl | 4-CH$_3$ | 121-124 |
| XVII-15 | 2-OCF$_3$ | 6-C$_2$H$_5$ | 4-Cl | 107-108 |

Example XX-1

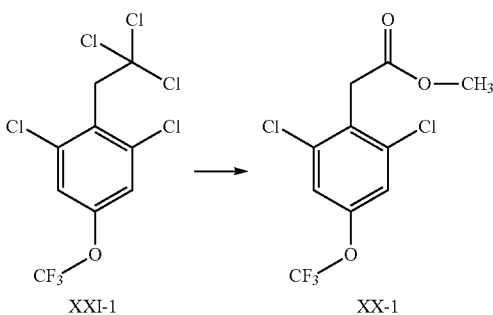

423.98 g of potassium hydroxide are initially charged in 2000 ml of methanol, the mixture is heated at 50° C., the compound according to Ex. XXI-1 is dissolved in 1474 ml of methanol and added dropwise. The mixture is stirred at about 55° C. overnight and then cooled, the pH is adjusted to 3 using conc. sulphuric acid and the mixture is stirred under reflux for 1 hour.

The solvent is distilled off and the precipitate is taken up in 500 ml of dichloromethane and 500 ml of water. The organic phase is separated off and the solvent is distilled off.

Yield: 465 g (52% of theory)

The compound XX-1 is used further without further purification to prepare compound XVII-1.

Example XX-5

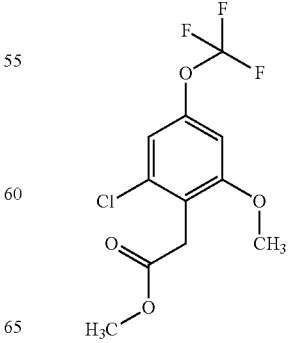

A reaction mixture consisting of 1 g (2.88 mmol) of the compound according to Example (XX-2), 1.56 g (8.6 mmol) of 30% strength sodium methoxide solution, 0.083 g (0.57 mmol) of copper(I) bromide and 0.78 g (10.5 mmol) of methyl acetate is stirred at a bath temperature of 120° C. for about 7 h. The mixture is taken up in water and filtered, and the filtrate is adjusted with 1N HCl to pH 1 and extracted with ethyl acetate (EA), dried over sodium sulphate and concentrated using a rotary evaporator. Purification is carried out by column chromatography on silica gel using EA/n-heptane 1:1

Yield: 0.6 g (=69% of theory)

For spectroscopic data see table with examples of the formula (XX).

Example XX-13

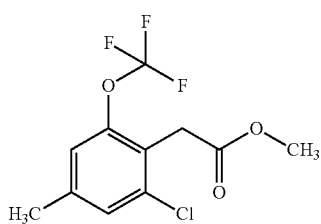

2 g (5.7 mmol) of the compound according to Example (XX-14) are initially charged in 40 ml of dioxane and 4 ml of water, and 1.11 g (8 mmol) of potassium carbonate, 1.98 g (1.7 mmol) of tetrakistriphenylphosphinepalladium and 1.08 g (8.6 mmol) of trimethylboroxine are added. The reaction mixture is stirred under reflux for 4 hours and then concentrated, taken up in 50 ml of 1N HCl and extracted twice with 20 ml of ethyl acetate (EA), and the organic phase is dried over sodium sulphate and concentrated using a rotary evaporator. The residue is purified on silica gel using EA/n-heptane 1:9.

Yield: 1 g (=61% of theory)

For spectroscopic data see table with examples of the formula (XX).

Analogously to Examples (XX-1), (XX-5) and (XX-13), it is possible to prepare the following compounds of the formula (XX):

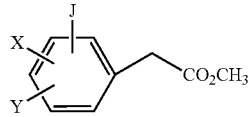

(XX)

| Ex. No. | J | X | Y | $^1$H-NMR data |
|---|---|---|---|---|
| XX-2 | 4-OCF$_3$ | 2-Br | 6-Cl | direct conversion into XVII-2 |
| XX-3 | 4-OCF$_3$ | 2-Br | 6-Br | direct conversion into XVII-3 |
| XX-4 | 4-OCF$_3$ | 2-OCH$_3$ | 6-Br | *3.71 (s, 3H, OCH$_3$) 3.81 (s, 3H, CO$_2$CH$_3$) 3.84 (s, 2H, Ar—CH$_2$) 6.68, 7.09 (2s, 2H—Ar—H) |
| XX-5 | 4-OCF$_3$ | 2-OCH$_3$ | 6-Cl | *3.68 (s, 3H, OCH$_3$) 6.63, 6.91 (2s, 2H, Ar—H) |
| XX-6 | 4-OCF$_3$ | 2-CH$_3$ | 6-CH$_3$ | m.p. 47° C. |
| XX-7 | 4-OCF$_3$ | 2-Br | 6-Cl | **3.74 (s, 3H, OCH$_3$) 4.05 (s, 2H, CH$_2$) 7.28, 7.41 (in each case s, 1H, ArH) |
| XX-8 | 4-OCF$_3$ | 2-Cl | 6-CH$_3$ | **3.71 (s, 3H, OCH$_3$) 3.83 (s, 2H, CH$_2$) 6.99, 7.14 (in each case s, 1H, ArH) |
| XX-9 | 2-OCF$_3$ | 6-Br | 4-Br | **3.72 (s, 3H, OCH$_3$) 3.87 (s, 2H, CH$_2$) 7.41, 7.71 (in each case s, 1H, ArH) |
| XX-10 | 2-OCF$_3$ | 6-CH$_3$ | 4-CH$_3$ | **3.68 (s, 3H, OCH$_3$) 3.70 (s, 2H, CH$_2$) 6.92, 6.96 (in each case s, 1H, ArH) |
| XX-11 | 2-OCF$_3$ | 6-OCH$_3$ | 4-Cl | **3.67 (s, 2H, CH$_2$) 3.70 (s, 3H, OCH$_3$) 3.85 (s, 3H, ArOCH$_3$) 6.84, 6.95 (in each case s, 1H, ArH) |
| XX-12 | 2-OCF$_3$ | 6-CH$_3$ | 4-Cl | ***3.71 (pseudo s, 5H, CH$_2$ and OCH$_3$) 7.16 (s, 2H, ArH) |
| XX-13 | 2-OCF$_3$ | 6-Cl | 4-CH$_3$ | ***3.71 (s, 3H, OCH$_3$) 3.84 (s, 2H, CH$_2$) 7.03, 7.21 (in each case s, 1H, ArH) |
| XX-14 | 2-OCF$_3$ | 6-Cl | 4-Br | *3.71 (s, 3H, OCH$_3$) 3.83 (s, 3H, CH$_2$) 7.37, 7.54 (in each case 2d, 1H, ArH) |

*$^1$H-NMR (500 MHz, CDCl$_3$): shifts δ in ppm
**$^1$H-NMR (300 MHz, CDCl$_3$): shifts δ in ppm
***$^1$H-NMR (400 MHz, CDCl$_3$): shifts δ in ppm Example XXI-1

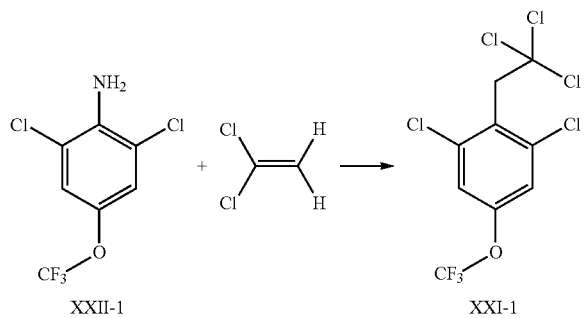

At room temperature, tert-butyl nitrite (229.9 g=2.23 mol) and copper(II) chloride (233.9 g=1.74 mol) are initially charged in 1500 ml of acetonitrile. Vinylidene chloride (733.6 g=7.57 mmol) is added over a period of 40 min, and 2,6-dichloro-4-trifluoromethoxyaniline (400 g=1.3 mmol) in 1350 ml of acetonitrile is then added dropwise over a period of 5 h at about 40° C. (slightly exothermic, immediate evolution of gas). After the evolution of gas has ended, the temperature is increased to 60° C. and the mixture is stirred for about 18 hours.

The reaction mixture is added to 4 liters of a 1N HCl solution, the organic phase is separated off, the aqueous phase is extracted with 300 ml of methyl tert-butyl ether, the organic phases are washed with 2 liters of a 1N HCl solution and the organic phase is separated off. The solvent is distilled off.

Yield: 573 g (53% of theory)

Analogously to Example (XXI-1), it is possible to prepare the following compounds of the formula (XXI):

(XXI)

| Ex. No. | J | X | Y |
|---------|---|---|---|
| XXI-2 | 4-OCF$_3$ | 2-Br | 6-Cl |
| XXI-3 | 4-OCF$_3$ | 2-Br | 6-Br |

Without further purification, the compounds of the formula XXI are used for preparing the compounds of the formula XX.

Example No. 1

Myzus Test

MYZUPE Spray Treatment

Solvents:
    78 parts by weight of acetone
    1.5 parts by weight of dimethylformamide
Emulsifier:
    0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration.

Discs of Chinese cabbage (*Brassica pekinensis*) which are infested by all stages of the green peach aphid (*Myzus persicae*) are sprayed with an active compound preparation of the desired concentration.

After the desired period of time, the effect in % is determined. 100% means that all aphids have been killed; 0% means that none of the aphids have been killed.

In this test, for example, the following compounds of the Preparation Examples show, at an application rate of 100 g/ha, an efficacy of ≧80%:
Ex. No. I-c-5

In this test, for example, the following compounds of the Preparation Examples show, at an application rate of 500 g/ha, an efficacy of ≧80%:
Ex. No. I-a-1, I-a-2, I-a-4, I-a-5, I-a-6, I-a-7, I-a-8, I-a-9, I-a-11, I-a-14, I-a-22, I-a-26, I-a-28, I-a-29, I-a-30, I-a-33, I-a-34, I-a-35, I-a-37, I-a-38, I-a-39, I-a-40, I-a-42, I-a-43, I-a-44, I-a-45, I-a-46, I-a-48, I-a-49, I-a-50, I-a-52, I-a-53, I-a-54, I-a-55, I-a-57, I-a-58, I-a-59, I-a-60, I-a-62, I-a-63, I-a-66, I-a-67, I-a-70, I-b-2, I-b-3, I-b-10, I-b-13, I-b-17, I-b-20, I-b-21, I-b-22, I-b-23, I-b-24, I-b-25, I-b-26, I-c-1, I-c-2, I-c-3, I-c-4, I-c-16, I-c-18, I-c-20, I-c-22, I-c-24, I-c-25, I-c-26, I-c-27, I-c-30, I-c-31, I-c-33, I-c-36

Example No. 2

*Tetranychus* Test; OP Resistant

TETRUR Spray Treatment

Solvents:
    78 parts by weight of acetone
    1.5 parts by weight of dimethylformamide
Emulsifier:
    0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration.

Discs of bean leaves (*Phaseolus vulgaris*) which are infested by all stages of the greenhouse red spider mite (*Tetranychus urticae*) are sprayed with an active compound preparation of the desired concentration.

After the desired period of time, the effect in % is determined. 100% means that all spider mites have been killed; 0% means that none of the spider mites have been killed.

In this test, for example, the following compounds of the Preparation Examples show, at an application rate of 20 g/ha, an efficacy of ≧80%:
Ex. No. I-a-38, I-b-22, I-c-26

In this test, for example, the following compounds of the Preparation Examples show, at an application rate of 100 g/ha, an efficacy of ≧80%:
Ex. No. I-a-1, I-a-7, I-a-8, I-a-9, I-a-10, I-a-18, I-a-19, I-a-22 I-a-26-I-a-28, I-a-29, I-a-31, I-a-33, I-a-35, I-a-37, I-a-39, I-a-40, I-a-41, I-a-43, I-a-44, I-a-47, I-a-48, I-a-49, I-a-51, I-a-52, I-a-53, I-a-54, I-a-55, I-a-56, I-a-57, I-a-60, I-a-61, I-a-62, I-a-63, I-a-66, I-a-67, I-a-70, I-b-2, I-b-3, I-b-6, I-b-7, I-b-8, I-b-12, I-b-13, I-b-17, I-b-20, I-b-21, I-b-23, I-b-24, I-b-25, I-b-26, I-b-10, I-c-11, I-c-12, I-c-13, I-c-14, I-c-15, I-c-16, I-c-17, I-c-20, I-c-24, I-c-27, I-c-31, I-c-36

Example No. 3

Phaedon Test

PHAECO Spray Treatment

Solvents:
    78 parts by weight of acetone
    1.5 parts by weight of dimethylformamide
Emulsifier:
    0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration.

Discs of Chinese cabbage (*Brassica pekinensis*) are sprayed with an active compound preparation of the desired concentration and, after drying, populated with larvae of the mustard beetle (*Phaedon cochleariae*).

After the desired period of time, the effect in % is determined. 100% means that all beetle larvae have been killed; 0% means that none of the beetle larvae have been killed.

In this test, for example, the following compounds of the Preparation Examples show, at an application rate of 500 g/ha, an efficacy of ≧80%:
Ex. No. I-a-4, I-a-6, I-a-11, I-a-14, I-a-29, I-a-30, I-a-34, I-a-35, I-c-4, I-b-2, I-b-3, I-b-21, I-b-23, I-b-25, I-a-27, I-a-41, I-a-44, I-a-49, I-a-50, I-c-2, I-c-13, I-c-25, I-c-27, I-c-29, I-c-33

Example No. 4

*Nilaparvata lugens* Test

NILALU Hydroponic Treatment

Solvents:
  78 parts by weight of acetone
  1.5 parts by weight of dimethylformamide
Emulsifier:
  0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration.

The active compound preparation is pipetted into water. The stated concentration refers to the amount of active compound per volume unit of water (mg/l=ppm); the infection with the rice brown planthopper (*Nilaparvata lugens*) is then carried out.

After the desired period of time, the effect in % is determined. 100% means that all rice planthoppers have been killed; 0% means that none of the rice planthoppers have been killed.

In this test, for example, the following compounds of the Preparation Examples show, at a concentration of 500 ppm after 7 d, an efficacy of ≧80%: I-a-4.

Example No. 5

*Spodoptera frugiperda* Test

SPODFR Spray Treatment

Solvents:
  78 parts by weight of acetone
  1.5 parts by weight of dimethylformamide
Emulsifier:
  0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration.

Discs of maize leaves (*Zea mays*) are sprayed with an active compound preparation of the desired concentration and, after drying, populated with caterpillars of the armyworm (*Spodoptera frugiperda*).

After the desired period of time, the effect in % is determined. 100% means that all caterpillars have been killed; 0% means that none of the caterpillars have been killed.

In this test, for example, the following compounds of the Preparation Examples show, at an application rate of 500 g/ha of a.i. after 7 d, an efficacy of ≧80%: I-a-6, I-a-34, I-b-2, I-b-3, I-c-2, I-c-4.

Example No. 6

*Meloidogyne* Test

MELGIN Spray Treatment

Solvent:
  80 parts by weight of acetone

To produce a suitable preparation of active compound, 1 part by weight of active compound is mixed with the stated amounts of solvent, and the concentrate is diluted with water to the desired concentration.

Containers are filled with sand, solution of active compound, *Meloidogyne incognita* egg/larvae suspension and lettuce seeds. The lettuce seeds germinate and the plants develop. On the roots, galls are formed.

After the desired period of time, the nematicidal activity is determined in % by the formation of galls. 100% means that no galls were found; 0% means that the number of galls on the treated plants corresponds to that of the untreated control.

In this test, for example, the following compounds of the Preparation Examples show an activity of ≧80% at an application rate of 20 ppm:
Ex. No. I-a-49, I-a-50, I-b-25, I-c-22

Example No. 7

*Nephotettix* Test

NEPHCI

Solvent: 7 parts by weight of dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Rice seedlings (*Oryza sativa*) are treated by being dipped into the active compound preparation of the desired concentration and populated with the green rice leafhopper (*Nephotettix cincticeps*) while the leaves are still moist.

After the desired period of time, the kill in % is determined. 100% means that all leafhoppers have been killed; 0% means that none of the leafhoppers have been killed.

In this test, for example, the following compounds of the Preparation Examples show an activity of ≧80% at an application rate of 100 ppm:
Ex. No. I-c-2

Example No. 8

*Boophilus microplus* Test

BOOPMI Injection

Solvent: dimethyl sulphoxide

A suitable preparation of active compound is prepared by mixing 1 part by weight of active compound with the stated amount of solvent and diluting the concentrate with solvent to the desired concentration.

The solution of active compound is injected into the abdomen (*Boophilus microplus*) and the animals are transferred into dishes and stored in a climatized room.

After the desired period of time the effect in % is determined. In this case 100% means that none of the ticks has laid fertile eggs.

In this test, for example, the following compounds of the Preparation Examples show an activity of ≧80% when applied at a rate of 20 μg/animal:
Ex. No. I-a-1, I-a-3, I-a-9, I-a-28, I-a-29, I-a-38, I-a-39, I-b-20, I-b-21, I-c-20

Example No. 9

*Lucilia cuprina* Test

LUCICU

Solvent: dimethyl sulphoxide

To produce a suitable preparation of active compound, 1 part by weight of active compound is mixed with the stated amount of water and the concentrate is diluted with water to the desired concentration.

Containers containing horsemeat treated with the active compound preparation of the desired concentration are populated with *Lucilia cuprina* larvae.

After the desired period of time, the kill in % is determined. 100% means that all larvae have been killed; 0% means that none of the larvae have been killed.

In this test, for example, the following compounds of the Preparation Examples show an activity of ≧80% at an application rate of 100 ppm:
Ex. No. I-a-29, I-a-38, I-b-21

Example 10

Herbicidal Pre-Emergence Action

Seeds of monocotyledonous and dicotyledonous weed and crop plants are placed in sandy lawn in wood fibre pots and covered with soil. The test compounds, formulated in the form of wettable powders (WP) or as emulsion concentrates (EC), are then, as an aqueous suspension with a water application rate of 800 l/ha (converted), with 0.2% of wetting agent added, applied to the surface of the covering soil.

After the treatment, the pots are placed in a greenhouse and kept under good growth conditions for the test plants. The visual assessment of the emergence damage on the test plants is carried out after a trial period of 3 weeks by comparison with the untreated controls (herbicidal effect in percent (%): 100% effect=the plants have died, 0% effect=like control plants).

Herbicidal Post-Emergence Action

Seeds of monocotyledonous and dicotyledonous weed and crop plants are placed in sandy lawn in wood fibre pots, covered with soil and cultivated in a greenhouse under good growth conditions. Two to three weeks after sowing, the test plants are treated at the one-leaf stage. The test compounds, formulated as wettable powders (WP) or as emulsion concentrates (EC), are then, as an aqueous suspension with a water application rate of 800 l/ha (converted), with 0.2% of wetting agent added, sprayed onto the green parts of the plants. After the test plants have been kept in the greenhouse under optimum growth conditions for about 3 weeks, the effect of the preparations is rated visually in comparison to untreated controls (herbicidal effect in percent (%): 100% effect=the plants have died, 0% effect=like control plants).

Applied by the pre-emergence method at 320 g/ha of a.i., the following compounds show an activity of ≧80% against *Lolium multiflorum* and *Setaria viridis*: I-a-2, I-a-22, I-a-25, I-a-26, I-a-27, I-a-29, I-a-38, I-a-39, I-a-46, I-a-49, I-a-50, I-a-51, I-a-52, I-a-54, I-a-57, I-a-59, I-a-60, I-a-61, I-a-62, I-a-63, I-a-64, I-a-65, I-a-66, I-a-67, I-a-68, I-a-70, I-b-13, I-b-15, I-b-17, I-b-21, I-b-22, I-b-24, I-b-25, I-b-26, I-c-16, I-c-18, I-c-22, I-c-26, I-c-29, I-c-30, I-c-31, I-c-32, I-c-33, I-c-34, I-c-35, I-c-36, I-c-37.

Applied by the post-emergence method at 80 g/ha of a.i., the following compounds show an activity of ≧70% against *Echinochloa crus-galli*, *Lolium multiflorum* and *Setaria viridis* and: I-a-24, I-a-26, I-a-37, I-a-46, I-a-49, I-a-50, I-a-51, I-a-54, I-a-58, I-a-59, I-a-60, I-a-61, I-a-63, I-a-64, I-a-65, I-a-66, I-a-67, I-a-68, I-b-25, I-c-32, I-c-37.

Post-Emergence Herbicidal Effect

Seeds of monocotyledonous and dicotyledonous weed plants and crop plants are placed in sandy loam soil in wood fibre pots or in plastic pots and are covered with earth and cultivated in a greenhouse and also, during the vegetation period, outdoors, outside of the greenhouse, under good growth conditions. 2 to 3 weeks after sowing, the trial plants are treated at the one- to three-leaf stage. The test compounds, formulated as wettable powders (WP) or liquids (EC), are sprayed onto the plants and the soil surface in various dosages, with a water application rate of 300 l/ha (converted) and with addition of wetting agent (0.2% to 0.3%). 3 to 4 weeks after the trial plants have been treated, the effect of the products is rated visually in comparison to untreated controls (herbicidal effect in percent: 100% effect=plants have died, 0% effect=like control plants).

Use of Safeners

If the testing is also to look at whether safeners can improve the tolerance of the crop plants for test substances, the following options are used for the application of the safener:
seeds of the crop plants are dressed with the safener substance prior to sowing (the amount of safener is stated as a percentage, based on the seed weight)
crop plants are sprayed with the safener, with a defined application rate per hectare, prior to application of the test substances (typically 1 day before the test substances are applied)
the safener is applied together with the test substance in the form of a tank mix (the amount of safener is reported in g/ha or as a proportion relative to the herbicide).

By comparing the effect of test substances on crop plants which have been treated with safener and without safener it is possible to assess the effect of the safener substance.

Greenhouse Container Trials with Cereals

Mefenpyr 1 Day Prior to Herbicide Application

|  | Application rate g of a.i./ha | 10 days after application Summer wheat observed (%) |
|---|---|---|
| (I-a-49) | 100 | 40 |
|  | 50 | 20 |
|  | 25 | 10 |

-continued

|  | Application rate g of a.i./ha | 10 days after application Summer wheat observed (%) |
|---|---|---|
| (I-a-49) + Mefenpyr | 100 + 50 | 0 |
|  | 50 + 50 | 0 |
|  | 25 + 50 | 0 |

|  | Application rate g of a.i./ha | 28 days after application Summer barley observed (%) | Summer wheat observed (%) |
|---|---|---|---|
| (I-a-50) | 100 | 60 | 70 |
|  | 50 | 50 | 60 |
|  | 25 | 30 | 40 |
|  | 12.5 | 8 | 10 |
| (I-a-50) + Mefenpyr | 100 + 50 | 30 | 20 |
|  | 50 + 50 | 10 | 5 |
|  | 25 + 50 | 5 | 0 |
|  | 12.5 + 50 | 0 | 0 |

|  | Application rate g of a.i./ha | 10 days after application Summer barley observed (%) | Summer wheat observed (%) |
|---|---|---|---|
| (I-b-24) | 100 | 30 | 40 |
|  | 50 | 30 | 40 |
|  | 25 | 20 | 40 |
|  | 12.5 | 10 | 30 |
| (I-b-24) + Mefenpyr | 100 + 50 | 10 | 20 |
|  | 50 + 50 | 8 | 10 |
|  | 25 + 50 | 5 | 5 |
|  | 12.5 + 50 | 5 | 0 |

|  | Application rate g of a.i./ha | 28 days after application Summer wheat observed (%) |
|---|---|---|
| (I-b-24) | 100 | 20 |
|  | 50 | 20 |
| (I-b-24) + Mefenpyr | 100 + 50 | 5 |
|  | 50 + 50 | 5 |

|  | Application rate g of a.i./ha | 10 days after application Summer wheat observed (%) |
|---|---|---|
| (I-b-25) | 100 | 20 |
| (I-b-25) + Mefenpyr | 100 + 50 | 0 |

Example 12

*Heliothis virescens* Test

Treatment of Transgenic Plants

Solvent: 7 parts by weight of acetone
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Soya bean shoots (*Glycine max*) of the cultivar Roundup Ready (trade mark of Monsanto Comp. USA) are treated by being dipped into the preparation of active compound of the desired concentration and are populated with the tobacco bud worm *Heliothis virescens* while the leaves are still moist.

After the desired period of time, the kill of the insects is determined.

Example 13

Critical Concentration Test/Soil Insects

Treatment of Transgenic Plants

Test insect: *Diabrotica balteata*—larvae in the soil
Solvent: 7 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is poured onto the soil. Here, the concentration of the active compound in the preparation is virtually immaterial; only the amount by weight of active compound per volume unit of soil, which is stated in ppm (mg/l), matters. The soil is filled into 0.25 l pots, and these are allowed to stand at 20° C.

Immediately after the preparation, 5 pregerminated maize corns of the cultivar YIELD GUARD (trade mark of Monsanto Comp., USA) are placed into each pot. After 2 days, the appropriate test insects are placed into the treated soil. After a further 7 days, the efficacy of the active compound is determined by counting the maize plants that have emerged (1 plant=20% activity).

Example 14

Boosting of Penetration into the Plant by Ammonium Salts or Phosphonium Salts, and Synergistic Boosting of Penetration into the Plant by Ammonium/Phosphonium Salts in Combination with Penetration Promoters This test measured the penetration of active compounds through enzymatically isolated cuticles of apple leaves.

The leaves used were cut in the fully developed state from apple trees of the Golden Delicious variety. The cuticles were isolated as follows:
- first of all, leaf discs labelled on the underside with dye and formed by punching were filled by means of vacuum infiltration with a pectinase solution (0.2% to 2% strength) buffered to a pH of between 3 and 4,
- sodium azide was then added and
- the leaf discs thus treated were left to stand until the original leaf structure broke down and the non-cellular cuticle underwent detachment.

After that, only those cuticles from the top leaf sides that were free from stomata and hairs were used. They were washed a number of times in alternation with water and with a buffer solution, pH 7. The clean cuticles obtained were, finally, applied to Teflon plaques, smoothed with a gentle jet of air, and dried.

In the next step the cuticular membranes obtained in this way were placed in stainless steel diffusion cells (transport chambers) for the purpose of membrane transport investigations. For these investigations the cuticles were placed centrally using tweezers on the edges of the diffusion cells, which were coated with silicone grease, and sealed with a ring, which was likewise greased. The arrangement had been chosen so that the morphological outer side of the cuticles was directed outwards, in other words facing the air, while the original inner side was facing the inside of the diffusion cell.

The diffusion cells were filled with a 30% strength ethylene glycol/water solution. Penetration was determined by applying 10 μl of the spray liquor of the composition below to the outer side of each of the cuticles. The spray liquor is prepared using local mains water of medium hardness.

After the spray liquors had been applied, the water was evaporated and then the chambers were inverted and placed in thermostated troughs, in which the temperature and humidity over the cuticles was adjustable by means of a gentle stream of air onto the cuticles, with the spray coating (20° C., 60% rh). At regular intervals, samples were taken using an autosampler, and the amount of active compound was determined using HPLC.

The results of the experiment are apparent from the table below. The numbers stated represent average values from 5 to 6 measurements. It can clearly be seen that ammonium sulphate, even on its own, significantly improves the penetration, and that together with RME there is a superadditive (synergistic) effect.

| Active compound | Penetration after 24 h/% | | | |
|---|---|---|---|---|
| | EC | EC + AS (1 g/l) | EC + RME (1 g/l) | EC + RME (1 g/l) + AS (1 g/l) |
| Example I-a-73 0.2 g/l in water/acetone 6:4 | 0.9 | 2.8 | 2.9 | 34.6 |
| Example I-a-49 0.2 g/l in water/acetone 6:4 | 0.24 | 0.6 | 1.4 | 26 |

RME = Rapeseed oil methyl ester (formulated for use as 500 EW, concentration figure in g of active compound/l)
AS = ammonium sulphate
EC = emulsifiable concentrate Example 15

Activity Boost Through Ammonium/Phosphonium Salts

*Myzus persicae* Test

Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with water to the desired concentration. For application with ammonium salts or phosphonium salts these are added in a concentration of 1000 ppm a.i. to the spray liquor.

Bell pepper plants (*Capsicum annuum*) which are heavily infested by the Green peach aphid (*Myzus persicae*) are treated with the active compound preparation of the desired concentration by spraying to runoff point. After the desired period of time, the kill in % is determined. 100% means that all animals have been killed; 0% means that none of the animals have been killed.

TABLE

| Active compound | Active compound ppm | Kill rate/% after 6 days | |
|---|---|---|---|
| | | | +AS (1000 ppm) |
| I-a-32 | 20 | 0 | 85 |
| I-a-39 | 20 | 10 | 40 |

AS = ammonium sulphate

Example 16

*Aphis gossypii* Test

Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration. For application with ammonium salts or phosphonium salts these are added in a concentration of 1000 ppm a.i. to the spray liquor.

Cotton plants (*Gossypium hirsutum*) heavily infested by the cotton aphid (*Aphis gossypii*) are sprayed to runoff with the preparation of active compound at the desired concentration.

After the desired period of time, the kill in % is determined. 100% means that all aphids have been killed; 0% means that none of the aphids have been killed.

TABLE

| Active compound | Active compound ppm | Kill rate/% after 6 days | |
|---|---|---|---|
| | | | +AS (1000 ppm) |
| I-a-9 | 20 | 65 | 85 |
| I-a-29 | 20 | 70 | 85 |
| I-a-29 | 4 | 5 | 70 |

Example 17

Activity Boost Through Ammonium/Phosphonium Salts in Combination with Penetration Promoters

*Myzus persicae* Test

Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with water to the desired concentration. For application with ammonium salts or phosphonium salts and penetration promoters (rapeseed oil methyl ester 500 EW) these are in each case added in a concentration of 1000 ppm to the spray liquor.

Bell pepper plants (*Capsicum annuum*) heavily infested by the green peach aphid (*Myzus persicae*) are sprayed to runoff with the preparation of active compound at the desired concentration. After the desired time, the kill in % is determined. 100% means that all of the animals have been killed; 0% means that no animals have been killed.

TABLE

| Active compound | Active compound/ ppm | +AS (1000 ppm) | +RME (1000 ppm) | +RME + AS (in each case 1000 ppm) |
|---|---|---|---|---|
| | | | Kill rate/% after 6 days | |
| I-a-29 | 20 | 0 | 70 | 95 | 100 |

Example 18

*Aphis gossypii* Test

Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration. For application with ammonium salts or phosphonium salts and penetration promoters (rapeseed oil methyl ester 500 EW) these are in each case added in a concentration of 1000 ppm a.i. to the spray liquor.

Cotton plants (*Gossypium hirsutum*) heavily infested by the cotton aphid (*Aphis gossypii*) are sprayed to runoff with the preparation of active compound at the desired concentration.

After the desired period of time, the kill in % is determined. 100% means that all aphids have been killed; 0% means that none of the aphids have been killed.

TABLE

| Active compound | Active compound/ ppm | +AS (1000 ppm) | +RME (1000 ppm) | +RME + AS (in each case 1000 ppm) |
|---|---|---|---|---|
| | | | Kill rate/% after 6 days | |
| I-a-32 | 4 | 5 | 30 | 70 | 80 |

The invention claimed is:
1. A compound of formula (I)

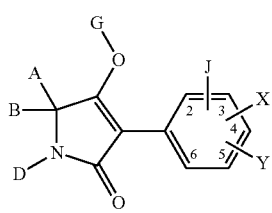

(I)

in which
J represents trifluoromethoxy,
X represents hydrogen, alkyl, halogen, haloalkyl, alkoxy or haloalkoxy,
Y represents hydrogen, alkyl, alkoxy or halogen, with the proviso, that at least one of the radicals J, X and Y is located in the 2-position of the phenyl radical and is not hydrogen, A represents hydrogen, in each case optionally halogen-substituted alkyl, alkenyl, alkoxyalkyl, alkylthioalkyl, saturated or unsaturated, optionally substituted cycloalkyl in which optionally at least one ring atom is replaced by a heteroatom, or in each case optionally halogen-, alkyl-, haloalkyl-, alkoxy-, haloalkoxy-, cyano- or nitro-substituted aryl, arylalkyl or hetaryl, B represents hydrogen, alkyl or alkoxyalkyl, or A and B together with the carbon atom to which they are attached represent a saturated or unsaturated, unsubstituted or substituted cycle which optionally contains at least one heteroatom, D represents hydrogen or an optionally substituted radical from the group consisting of alkyl, alkenyl, alkynyl, alkoxyalkyl, saturated or unsaturated cycloalkyl in which optionally one or more ring members are replaced by heteroatoms, arylalkyl, aryl, hetarylalkyl or hetaryl or A and D together with the atoms to which they are attached represent a saturated or unsaturated cycle which optionally contains at least one heteroatom and which is unsubstituted or substituted in the A, D moiety, G represents hydrogen (a) or represents one of the groups

(b)

(c)

(d)

(e)

E or
(f)

(g)

in which
E represents a metal ion equivalent or an ammonium ion,
L represents oxygen or sulphur,
M represents oxygen or sulphur,
$R^1$ represents in each case optionally halogen-substituted alkyl, alkenyl, alkoxyalkyl, alkylthioalkyl, polyalkoxyalkyl or optionally halogen-, alkyl- or alkoxy-substituted cycloalkyl which may be interrupted by at least one heteroatom, in each case optionally substituted phenyl, phenylalkyl, hetaryl, phenoxyalkyl or hetaryloxyalkyl,
$R^2$ represents in each case optionally halogen-substituted alkyl, alkenyl, alkoxyalkyl, polyalkoxyalkyl or represents in each case optionally substituted cycloalkyl, phenyl or benzyl,
$R^3$, $R^4$ and $R^5$ independently of one another represent in each case optionally halogen-substituted alkyl, alkoxy, alkylamino, dialkylamino, alkylthio, alkenylthio, cycloalkylthio or represent in each case optionally substituted phenyl, benzyl, phenoxy or phenylthio, $R^6$ and $R^7$ independently of one another represent hydrogen, in each case optionally halogen-substituted alkyl, cycloalkyl, alkenyl, alkoxy, alkoxyalkyl, represent optionally substituted phenyl, represent optionally substituted benzyl, or together with the nitrogen atom to which they are attached represent a cycle which is optionally interrupted by oxygen or sulphur.

2. A compound of the formula (I) according to claim 1 in which

J represents trifluoromethoxy,

X represents hydrogen, halogen, $C_1$-$C_6$-alkyl, $C_1$-$C_4$-haloalkyl, $C_1$-$C_6$-alkoxy or $C_1$-$C_4$-haloalkoxy, Y represents hydrogen, $C_1$-$C_6$-alkyl, $C_1$-$C_6$-alkoxy or halogen, with the proviso, that at least one of the radicals J, X and Y is located in the 2-position of the phenyl radical and is not hydrogen, resulting in the phenyl substitution patterns below

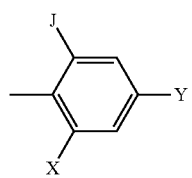
(A)

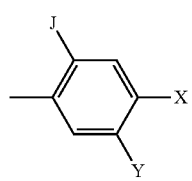
(B)

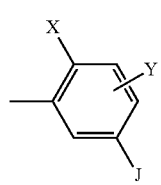
(C)

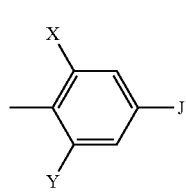
(D)

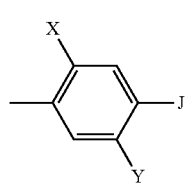
(E)

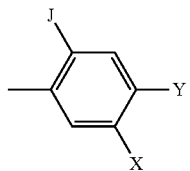
(K)

where in the phenyl substitution patterns (C), (D), (E) and (K) X and Y are both not hydrogen simultaneously, A represents hydrogen or in each case optionally halogen-substituted $C_1$-$C_{12}$-alkyl, $C_3$-$C_8$-alkenyl, $C_1$-$C_{10}$-alkoxy-$C_1$-$C_8$-alkyl, $C_1$-$C_{10}$-alkylthio-$C_1$-$C_6$-alkyl, optionally halogen-, $C_1$-$C_6$-alkyl- or $C_1$-$C_6$-alkoxy-substituted $C_3$-$C_8$-cycloalkyl in which optionally one or two not directly adjacent ring members are replaced by oxygen and/or sulphur or represents in each case optionally halogen-, $C_1$-$C_6$-alkyl-, $C_1$-$C_6$-haloalkyl-, $C_1$-$C_6$-alkoxy-, $C_1$-$C_6$-haloalkoxy-, cyano- or nitro-substituted phenyl, naphthyl, hetaryl having 5 to 6 ring atoms, phenyl-$C_1$-$C_6$-alkyl or naphthyl-$C_1$-$C_6$-alkyl, B represents hydrogen, $C_1$-$C_{12}$-alkyl or $C_1$-$C_8$-alkoxy-$C_1$-$C_6$-alkyl or A, B and the carbon atom to which they are attached represent saturated $C_3$-$C_{10}$-cycloalkyl or unsaturated $C_5$-$C_{10}$-cycloalkyl in which optionally one ring member is replaced by oxygen or sulphur and which are optionally mono- or disubstituted by $C_1$-$C_8$-alkyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl-$C_1$-$C_2$-alkoxy, $C_3$-$C_{10}$-cycloalkyl, $C_1$-$C_8$-haloalkyl, $C_1$-$C_8$-alkoxy, $C_1$-$C_8$-alkylthio, halogen or phenyl or A, B and the carbon atom to which they are attached represent $C_3$-$C_6$-cycloalkyl which is substituted by an alkylenediyl group which is optionally substituted by $C_1$-$C_4$-alkyl and optionally contains one or two not directly adjacent oxygen and/or sulphur atoms, or by an alkylenedioxyl or by an alkylenedithioyl group which, together with the carbon atom to which it is attached, forms a further five- to eight-membered ring or A, B and the carbon atom to which they are attached represent $C_3$-$C_8$-cyclo-alkyl or $C_5$-$C_8$-cycloalkenyl in which two substituents together with the carbon atoms to which they are attached represent in each case optionally $C_1$-$C_6$-alkyl-, $C_1$-$C_6$-alkoxy- or halogen-substituted $C_2$-$C_6$-alkanediyl, $C_2$-$C_6$-alkenediyl or $C_4$-$C_6$-alkanedienediyl in which optionally one methylene group is replaced by oxygen or sulphur, D represents hydrogen, in each case optionally halogen-substituted $C_1$-$C_{12}$-alkyl, $C_3$-$C_8$-alkenyl, $C_3$-$C_8$-alkynyl, $C_1$-$C_{10}$-alkoxy-$C_2$-$C_8$-alkyl, optionally halogen-, $C_1$-$C_4$-alkyl-, $C_1$-$C_4$-alkoxy- or $C_1$-$C_4$-haloalkyl-substituted $C_3$-$C_8$-cycloalkyl in which optionally one ring member is replaced by oxygen or sulphur or in each case optionally halogen-, $C_1$-$C_6$-alkyl-, $C_1$-$C_6$-haloalkyl-, $C_1$-$C_6$-alkoxy-, $C_1$-$C_6$-haloalkoxy-, cyano- or nitro-substituted phenyl, hetaryl having 5 of 6 ring atoms, phenyl-$C_1$-$C_6$-alkyl or hetaryl-$C_1$-$C_6$-alkyl having 5 or 6 ring atoms or A and D together represent in each case optionally substituted $C_3$-$C_6$-alkanediyl or $C_3$-$C_6$-alkenediyl in which optionally one methylene group is replaced by a carbonyl group, oxygen or sulphur, possible substituents being in each case:
halogen, hydroxyl, mercapto or in each case optionally halogen-substituted $C_1$-$C_{10}$-alkyl, $C_1$-$C_6$-alkoxy, $C_1$-$C_6$-alkylthio, $C_3$-$C_7$-cycloalkyl, phenyl or benzyloxy, or a further $C_3$-$C_6$-alkanediyl grouping, $C_3$-$C_6$-alkenediyl grouping or a butadienyl grouping which is optionally substituted by $C_1$-$C_6$-alkyl or in which optionally two adjacent substituents together with the carbon atoms to which they are attached form a further saturated or unsaturated cycle having 5 or 6 ring atoms which may contain oxygen or sulphur or which optionally contains one of the following groups

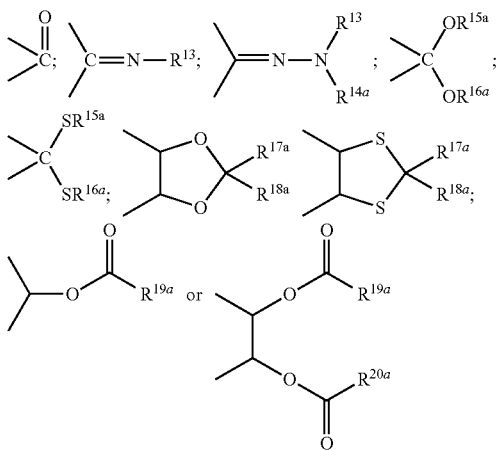

G represents hydrogen (a) or represents one of the groups

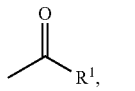 (b)

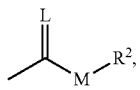 (c)

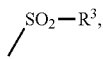 (d)

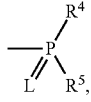 (e)

E, or (f)

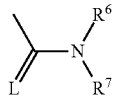 (g)

in which
E represents a metal ion equivalent or an ammonium ion,
L represents oxygen or sulphur and
M represents oxygen or sulphur,
$R^1$ represents in each case optionally halogen-substituted $C_1$-$C_{20}$-alkyl, $C_2$-$C_{20}$-alkenyl, $C_1$-$C_8$-alkoxy-$C_1$-$C_8$-alkyl, $C_1$-$C_8$-alkylthio-$C_1$-$C_8$-alkyl, poly-$C_1$-$C_8$-alkoxy-$C_1$-$C_8$-alkyl or optionally halogen-, $C_1$-$C_6$-alkyl- or $C_1$-$C_6$-alkoxy-substituted $C_3$-$C_8$-cycloalkyl in which optionally one or more not directly adjacent ring members are replaced by oxygen and/or sulphur,
represents optionally halogen-, cyano-, nitro-, $C_1$-$C_6$-alkyl-, $C_1$-$C_6$-alkoxy-, $C_1$-$C_6$-haloalkyl-, $C_1$-$C_6$-haloalkoxy-, $C_1$-$C_6$-alkylthio- or $C_1$-$C_6$-alkylsulphonyl-substituted phenyl,
represents optionally halogen-, nitro-, cyano-, $C_1$-$C_6$-alkyl-, $C_1$-$C_6$-alkoxy-, $C_1$-$C_6$-haloalkyl- or $C_1$-$C_6$-haloalkoxy-substituted phenyl-$C_1$-$C_6$-alkyl,
represents optionally halogen- or $C_1$-$C_6$-alkyl-substituted 5- or 6-membered hetaryl,
represents optionally halogen- or $C_1$-$C_6$-alkyl-substituted phenoxy-$C_1$-$C_6$-alkyl or
represents optionally halogen-, amino- or $C_1$-$C_6$-alkyl-substituted 5- or 6-membered hetaryloxy-$C_1$-$C_6$-alkyl,
$R^2$ represents in each case optionally halogen-substituted $C_1$-$C_{20}$-alkyl, $C_2$-$C_{20}$-alkenyl, $C_1$-$C_8$-alkoxy-$C_2$-$C_8$-alkyl, poly-$C_1$-$C_8$-alkoxy-$C_2$-$C_8$-alkyl,
represents optionally halogen-, $C_1$-$C_6$-alkyl- or $C_1$-$C_6$-alkoxy-substituted $C_3$-$C_8$-cycloalkyl or
represents in each case optionally halogen-, cyano-, nitro-, $C_1$-$C_6$-alkyl-, $C_1$-$C_6$-alkoxy-, $C_1$-$C_6$-haloalkyl- or $C_1$-$C_6$-haloalkoxy-substituted phenyl or benzyl,
$R^3$ represents optionally halogen-substituted $C_1$-$C_8$-alkyl or represents in each case optionally halogen-, $C_1$-$C_6$-alkyl-, $C_1$-$C_6$-alkoxy-, $C_1$-$C_4$-haloalkyl-, $C_1$-$C_4$-haloalkoxy-, cyano- or nitro-substituted phenyl or benzyl,
$R^4$ and $R^5$ independently of one another represent in each case optionally halogen-substituted $C_1$-$C_8$-alkyl, $C_1$-$C_8$-alkoxy, $C_1$-$C_8$-alkylamino, di-($C_1$-$C_8$-alkyl)amino, $C_1$-$C_8$-alkylthio, $C_2$-$C_8$-alkenylthio, $C_3$-$C_7$-cycloalkylthio or represent in each case optionally halogen-, nitro-, cyano-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkyl- or $C_1$-$C_4$-haloalkyl-substituted phenyl, phenoxy or phenyl-thio,
$R^6$ and $R^7$ independently of one another represent hydrogen, represent in each case optionally halogen-substituted $C_1$-$C_8$-alkyl, $C_3$-$C_8$-cycloalkyl, $C_1$-$C_8$-alkoxy, $C_3$-$C_8$-alkenyl, $C_1$-$C_8$-alkoxy-$C_1$-$C_8$-alkyl, represent optionally halogen-, $C_1$-$C_8$-haloalkyl-, $C_1$-$C_8$-alkyl- or $C_1$-$C_8$-alkoxy-substituted phenyl, optionally halogen-, $C_1$-$C_8$-alkyl-, $C_1$-$C_8$-haloalkyl- or $C_1$-$C_8$-alkoxy-substituted benzyl or together represent an optionally $C_1$-$C_4$-alkyl-substituted $C_3$-$C_6$-alkylene radical in which optionally one carbon atom is replaced by oxygen or sulphur,
$R^{13}$ represents hydrogen, represents in each case optionally halogen-substituted $C_1$-$C_8$-alkyl or $C_1$-$C_8$-alkoxy, represents optionally halogen-, $C_1$-$C_4$-alkyl- or $C_1$-$C_4$-alkoxy-substituted $C_3$-$C_8$-cycloalkyl in which optionally one methylene group is replaced by oxygen or sulphur, or represents in each case optionally halogen-, $C_1$-$C_6$-alkyl-, $C_1$-$C_6$-alkoxy-, $C_1$-$C_4$-haloalkyl-, $C_1$-$C_4$-haloalkoxy-, nitro- or cyano-substituted phenyl, phenyl-$C_1$-$C_4$-alkyl or phenyl-$C_1$-$C_4$-alkoxy,
$R^{14a}$ represents hydrogen or $C_1$-$C_8$-alkyl or
$R^{13}$ and $R^{14a}$ together represent $C_4$-$C_6$-alkanediyl,
$R^{15a}$ and $R^{16a}$ are identical or different and represent $C_1$-$C_6$-alkyl or
$R^{15a}$ and $R^{16a}$ together represent a $C_2$-$C_4$-alkanediyl radical which is optionally substituted by $C_1$-$C_6$-alkyl, $C_1$-$C_6$-haloalkyl or by optionally halogen-, $C_1$-$C_6$- alkyl-, $C_1$-$C_4$-haloalkyl-, $C_1$-$C_6$-alkoxy-, $C_1$-$C_4$-haloalkoxy-, nitro- or cyano-substituted phenyl, $R^{17a}$ and $R^{18a}$ independently of one another preferably represent hydrogen, represent optionally halogen-substituted $C_1$-$C_8$-alkyl or represent optionally halogen-, $C_1$-$C_6$-alkyl-, $C_1$-$C_6$-alkoxy-, $C_1$-$C_4$-haloalkyl-, $C_1$-$C_4$-haloalkoxy-, nitro- or cyano-substituted phenyl or $R^{17a}$ and $R^{18a}$ together with the carbon atom to which they are attached represent a carbonyl group or represent optionally halogen-, $C_1$-$C_4$-alkyl- or $C_1$-$C_4$-alkoxy-substituted $C_5$-$C_7$-cycloalkyl in which optionally one methylene group is replaced by oxygen or sulphur, $R^{19a}$ and $R^{20a}$ independently of one another represent $C_1$-$C_{10}$-alkyl, $C_2$-$C_{10}$-alkenyl, $C_1$-$C_{10}$-alkoxy, $C_1$-$C_{10}$-alkylamino, $C_3$-$C_{10}$-alkenylamino, di-($C_1$-$C_{10}$-alkyl)amino or di-($C_3$-$C_{10}$-alkenyl)amino.

3. A compound of the formula (I) according to claim 1 in which

J represents trifluoromethoxy,

X represents hydrogen, fluorine, chlorine, bromine, $C_1$-$C_4$-alkyl, trifluoromethyl or $C_1$-$C_4$-alkoxy, Y represents hydrogen, fluorine, chlorine, bromine, $C_1$-$C_4$-alkoxy or $C_1$-$C_4$-alkyl, with the proviso, that at least one of the radicals J, X and Y is located in the 2-position of the phenyl radical and is not hydrogen, resulting in the phenyl substitution patterns below

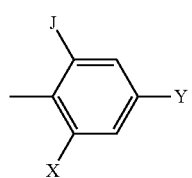
(A)

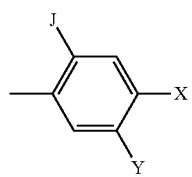
(B)

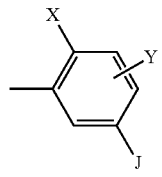
(C)

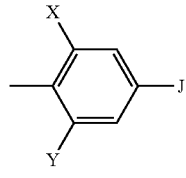
(D)

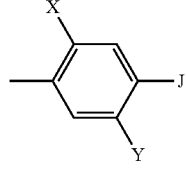
(E)

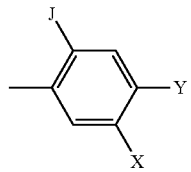
(K)

where in the phenyl substitution patterns (C), (D), (E) and (K) X and Y are both not hydrogen simultaneously, A represents hydrogen, $C_1$-$C_6$-alkyl or $C_1$-$C_4$-alkoxy-$C_1$-$C_2$-alkyl, each of which is optionally mono- to trisubstituted by fluorine or chlorine, represents $C_3$-$C_6$-cycloalkyl which is optionally mono- or disubstituted by $C_1$-$C_2$-alkyl or $C_1$-$C_2$-alkoxy and which may optionally be interrupted by an oxygen atom, represents phenyl or benzyl, each of which is optionally mono- or disubstituted by fluorine, chlorine, bromine, $C_1$-$C_4$-alkyl, $C_1$-$C_2$-haloalkyl, $C_1$-$C_4$-alkoxy, $C_1$-$C_2$-haloalkoxy, cyano or nitro, B represents hydrogen, $C_1$-$C_4$-alkyl or $C_1$-$C_2$-alkoxyl-$C_1$-$C_2$-alkyl or A, B and the carbon atom to which they are attached represent saturated or unsaturated $C_5$-$C_7$-cycloalkyl in which optionally one ring member is replaced by oxygen or sulphur and which is optionally mono- or disubstituted by $C_1$-$C_6$-alkyl, $C_1$-$C_4$-alkoxy-$C_1$-$C_2$-alkyl, $C_1$-$C_4$-alkoxy-$C_1$-$C_2$-alkoxy, $C_3$-$C_6$-cycloalkyl-methoxy, trifluoromethyl or $C_1$-$C_6$-alkoxy, or A, B and the carbon atom to which they are attached $C_5$-$C_6$-cycloalkyl which is substituted by an alkylenediyl group which is optionally substituted by methyl or ethyl and optionally contains one or two not directly adjacent oxygen and/or sulphur atoms, or by an alkylenedioxyl or by an alkylenedithiol group which, together with the carbon atom to which it is attached, forms a further five- to eight-membered ring, or A, B and the carbon atom to which they are attached represent $C_3$-$C_6$-cycloalkyl or $C_5$-$C_6$-cycloalkenyl in which two substituents together with the carbon atoms to which they are attached represent in each case optionally $C_1$-$C_2$-alkyl- or $C_1$-$C_2$-alkoxy-substituted $C_2$-$C_4$-alkanediyl, $C_2$-$C_4$-alkenediyl or butadiendiyl, D represents hydrogen, $C_1$-$C_6$-alkyl, $C_3$-$C_6$-alkenyl or $C_1$-$C_4$-alkoxy-$C_2$-$C_3$-alkyl, each of which is optionally mono- to trisubstituted by fluorine, represents $C_3$-$C_6$-cycloalkyl which is optionally mono- or disubstituted by $C_1$-$C_4$-alkyl, $C_1$-$C_4$-alkoxy or $C_1$-$C_2$-haloalkyl and in which optionally one methylene group is replaced by oxygen, or A and D together represent $C_3$-$C_5$-alkanediyl in which one methylene group may be replaced by a carbonyl group, oxygen or sulphur and which may optionally be mono- or disubstituted, possible substituents being $C_1$-$C_2$-alkyl or $C_1$-$C_2$-alkoxy or A and D together with the atoms to which they are attached represent one of the groups AD-1 to AD-10:

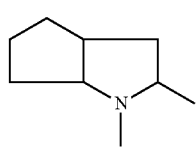
AD-1

-continued

AD-2 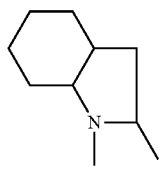

AD-3 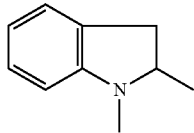

AD-4 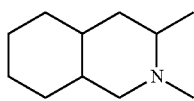

AD-5 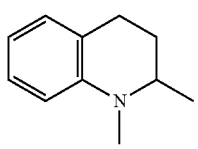

AD-6 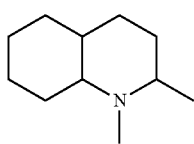

AD-7 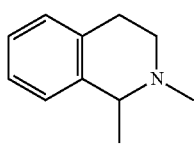

AD-8 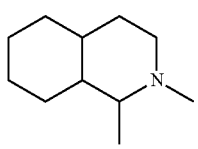

AD-9 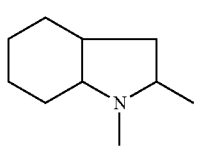

AD-10 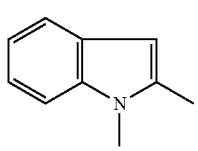

G represents hydrogen (a) or represents one of the groups (b) 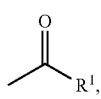

-continued (c) 

(d) 

(e) 

(f) E or (g) 

in which

E represents a metal ion equivalent or an ammonium ion,

L represents oxygen or sulphur and

M represents oxygen or sulphur, $R^1$ represents $C_1$-$C_8$-alkyl, $C_2$-$C_{18}$-alkenyl, $C_1$-$C_4$-alkoxy-$C_1$-$C_2$-alkyl or $C_1$-$C_4$-alkylthio-$C_1$-$C_2$-alkyl, each of which is optionally mono- to trisubstituted by fluorine or chlorine, or $C_3$-$C_6$-cycloalkyl which is optionally mono- or disubstituted by fluorine, chlorine, $C_1$-$C_2$-alkyl or $C_1$-$C_2$-alkoxy and in which optionally one or two not directly adjacent ring members are replaced by oxygen, represents phenyl which is optionally mono- or disubstituted by fluorine, chlorine, bromine, cyano, nitro, $C_1$-$C_4$-alkyl, $C_1$-$C_4$-alkoxy, $C_1$-$C_2$-halo-alkyl or $C_1$-$C_2$-haloalkoxy, $R^2$ represents $C_1$-$C_8$-alkyl, $C_2$-$C_8$-alkenyl or $C_1$-$C_4$-alkoxy-$C_2$-$C_4$-alkyl, each of which is optionally mono- to trisubstituted by fluorine, represents $C_3$-$C_6$-cycloalkyl which is optionally monosubstituted by $C_1$-$C_2$-alkyl or $C_1$-$C_2$-alkoxy or represents phenyl or benzyl, each of which is optionally mono- or disubstituted by fluorine, chlorine, bromine, cyano, nitro, $C_1$-$C_4$-alkyl, $C_1$-$C_3$-alkoxy, trifluoromethyl or trifluoromethoxy, $R^3$ represents $C_1$-$C_6$-alkyl which is optionally mono- to trisubstituted by fluorine or represents phenyl which is optionally monosubstituted by fluorine, chlorine, bromine, $C_1$-$C_4$-alkyl, $C_1$-$C_4$-alkoxy, trifluoromethyl, trifluoromethoxy, cyano or nitro, $R^4$ represents $C_1$-$C_6$-alkyl, $C_1$-$C_6$-alkoxy, $C_1$-$C_6$-alkylamino, di-($C_1$-$C_6$-alkyl)amino, $C_1$-$C_6$-alkylthio, $C_3$-$C_4$-alkenylthio, $C_3$-$C_6$-cycloalkylthio or represents phenyl, phenoxy or phenylthio, each of which is optionally monosubstituted by fluorine, chlorine, bromine, nitro, cyano, $C_1$-$C_3$-alkoxy, $C_1$-$C_3$-haloalkoxy, $C_1$-$C_3$-alkylthio, $C_1$-$C_3$-haloalkylthio, $C_1$-$C_3$-alkyl or trifluoromethyl, $R^5$ represents $C_1$-$C_6$-alkoxy or $C_1$-$C_6$-alkylthio, $R^6$ represents hydrogen, $C_1$-$C_6$-alkyl, $C_3$-$C_6$-cycloalkyl, $C_1$-$C_6$-alkoxy, $C_3$-$C_6$-alkenyl, $C_1$-$C_6$-alkoxy-$C_1$-$C_4$-alkyl, represents phenyl which is optionally monosubstituted by fluorine, chlorine, bromine, trifluoromethyl, $C_1$-$C_4$-alkyl or $C_1$-$C_4$-alkoxy, represents benzyl which is optionally monosubstituted by fluorine, chlorine, bromine, $C_1$-$C_4$-alkyl, trifluoromethyl or $C_1$-$C_4$-alkoxy, $R^7$ represents $C_1$-$C_6$-alkyl, $C_3$-$C_6$-alkenyl or $C_1$-$C_6$-alkoxy-$C_1$-$C_4$-alkyl, $R^6$ and $R^7$ together represent an optionally methyl- or ethyl-substituted $C_4$-$C_5$-alkylene radical in which optionally one methylene group is replaced by oxygen or sulphur.

4. A compound of the formula (I) according to claim 1 in which

J represents trifluoromethoxy,

X represents hydrogen, fluorine, chlorine, bromine, methyl, ethyl, propyl, methoxy or ethoxy, Y represents hydrogen, chlorine, bromine, methyl, ethyl or methoxy, with the proviso, that at least one of the radicals J, X and Y is located in the 2-position of the phenyl radical and is not hydrogen, resulting in the phenyl substitution patterns below

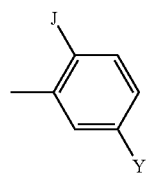
(F)

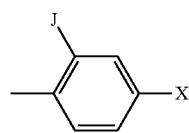
(G)

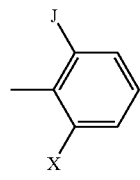
(H)

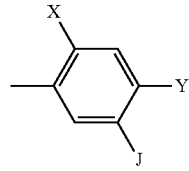
(I)

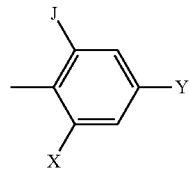
(J)

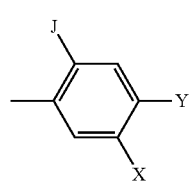
(K)

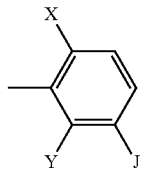
(L)

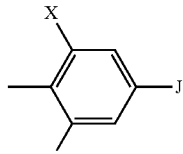
(M)

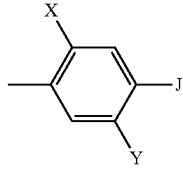
(N)

where in the phenyl substitution patterns (G) and (H), X is not hydrogen, and in the phenyl substitution patterns (J), (K), (L), (M) and (N), X and Y are not hydrogen, A represents hydrogen, $C_1$-$C_4$-alkyl or $C_1$-$C_2$-alkoxy-$C_1$-$C_2$-alkyl, each of which is optionally mono- to trisubstituted by fluorine, represents cyclopropyl, cyclopentyl or cyclohexyl, represents in each case optionally fluorine-, chlorine-, bromine-, methyl-, ethyl-, n-propyl-, isopropyl-, methoxy-, ethoxy-, trifluoromethyl-, trifluoromethoxy-, cyano- or nitro-substituted phenyl or benzyl, B represents hydrogen, methyl or ethyl or A, B and the carbon atom to which they are attached represent saturated $C_5$-$C_6$-cycloalkyl in which optionally one ring member is replaced by oxygen or sulphur and which is optionally monosubstituted by methyl, ethyl, propyl, isopropyl, methoxymethyl, ethoxymethyl, propoxymethyl, trifluoromethyl, methoxy, ethoxy, propoxy, butoxy, methoxyethyl, ethoxyethyl, methoxyethoxy, ethoxyethoxy, cyclopropylmethoxy, cyclopentylmethoxy or cyclohexylmethoxy, or A, B and the carbon atom to which they are attached represent $C_6$-cycloalkyl which is optionally substituted by an alkylenedioxyl group which contains two not directly adjacent oxygen atoms, or A, B and the carbon atom to which they are attached represent $C_5$-$C_6$-cycloalkyl or $C_5$-$C_6$-cycloalkenyl in which two substituents together with the carbon atoms to which they are attached represent $C_2$-$C_4$-alkanediyl or $C_2$-$C_4$-alkenediyl or butadienediyl, D represents hydrogen, $C_1$-$C_4$-alkyl, $C_3$-$C_4$-alkenyl, $C_1$-$C_4$-alkoxy-$C_2$-$C_3$-alkyl, represents cyclopropyl, cyclopentyl or cyclohexyl, each of which is optionally mono- to trisubstituted by fluorine, or A and D together very particularly preferably represent $C_3$-$C_5$-alkanediyl which is optionally monosubstituted by methyl or methoxy and in which optionally one carbon atom is replaced by oxygen or sulphur, or represent the group AD-1, G represents hydrogen (a) or represents one of the groups

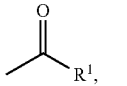 (b)

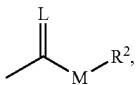 (c)

—SO$_2$—R$^3$ or (d)

E, (f)

in which
L represents oxygen or sulphur,
M represents oxygen or sulphur and
E represents an ammonium ion,
R$^1$ represents C$_1$-C$_6$-alkyl, C$_2$-C$_{17}$-alkenyl, C$_1$-C$_2$-alkoxy-C$_1$-alkyl, C$_1$-C$_2$-alkylthio-C$_1$-alkyl or represents cyclopropyl or cyclohexyl, each of which is optionally monosubstituted by fluorine, chlorine, methyl or methoxy, represents phenyl which is optionally monosubstituted by fluorine, chlorine, bromine, cyano, nitro, methyl, methoxy, trifluoromethyl or trifluoromethoxy,
R$^2$ represents C$_1$-C$_8$-alkyl, C$_2$-C$_6$-alkenyl or C$_1$-C$_4$-alkoxy-C$_2$-C$_3$-alkyl, phenyl or benzyl, each of which is optionally monosubstituted by fluorine,
R$^3$ represents C$_1$-C$_8$-alkyl.

5. A compound of the formula (I) according to claim 1, in which
J represents trifluoromethoxy,
X represents hydrogen, chlorine, bromine, methyl, ethyl, or methoxy,
Y represents hydrogen, chlorine, bromine, methyl or methoxy,
with the proviso, that at least one of the radicals J, X and Y is located in the 2-position of the phenyl radical and is not hydrogen, resulting in the phenyl substitution patterns below

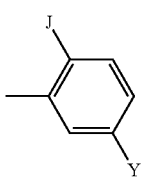 (F)

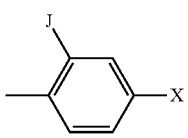 (G)

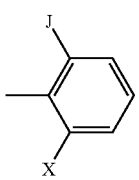 (H)

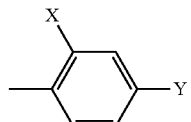 (I)

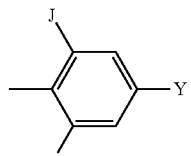 (J)

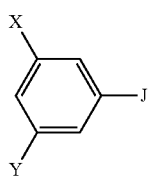 (M)

where in the phenyl substitution patterns (G) and (H), X is not hydrogen, and in the phenyl substitution patterns (J) and (M), X and Y are not hydrogen,
A represents C$_1$-C$_4$-alkyl or cyclopropyl,
B represents hydrogen or methyl,
A, B and the carbon atom to which they are attached represent saturated C$_5$-C$_6$-cycloalkyl in which optionally one ring member is replaced by oxygen and which is optionally monosubstituted by methoxymethyl, methoxy, ethoxy, propoxy or butoxy,
or represent

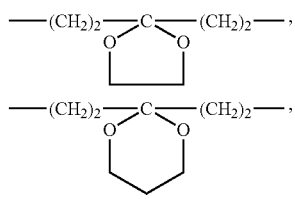

D represents hydrogen or cyclopropyl,
or
A and D together represent C$_3$-C$_5$-alkanediyl,
G represents hydrogen (a) or one of the groups

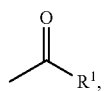 (b)

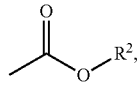 (c)

E, (f)

R$^1$ represents C$_1$-C$_6$-alkyl,
R$^2$ represents C$_1$-C$_8$-alkyl or benzyl.

6. A process for preparing a compound of the formula (I) according to claim 1, characterized in that, (A) in order to obtain a compound of formula (I-a)

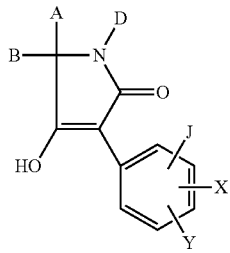
(I-a)

in which
A, B, D, J, X and Y are as defined in claim 1,
an N-acylamino acid ester of formula (II)

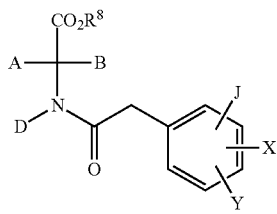
(II)

in which
A, B, D, J, X and Y are as defined in claim 1,
and
$R^8$ represents alkyl,
is condensed intramolecularly in the presence of a diluent and in the presence of a base, (B) in order to obtain a compound of formula (I-b)

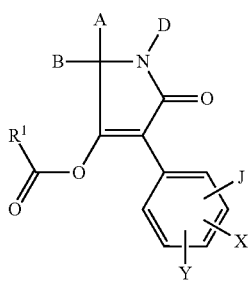
(I-b)

in which A, B, D, J, $R^1$, X, and Y are as defined in claim 1, a compound of the formula (I-a) in which A, B, D, J, X and Y are as defined in claim 1 is in each case reacted (α) with an acid halide of formula (III)

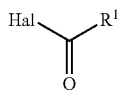
(III)

in which
$R^1$ is as defined in claim 1 and
Hal represents halogen
or (β) with a carboxylic anhydride of formula (IV)

$R^1$—CO—O—CO—$R^1$ (IV)

in which
$R^1$ is as defined in claim 1,
optionally in the presence of a diluent and optionally in the presence of an acid binder;

(C) in order to obtain a compound of formula (I-c)

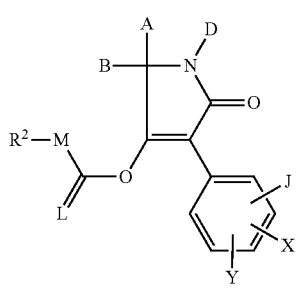
(I-c)

in which A, B, D, J, $R^2$, M, X and Y are as defined in claim 1 and L represents oxygen, a compound of the formula (I-a) in which A, B, D, J, X and Y are as defined in claim 1 is in each case reacted with a chloroformic ester or a chloroformic thioester of formula (V)

$R^2$-M-CO—Cl (V)

in which
$R^2$ and M are as defined in claim 1,
optionally in the presence of a diluent and optionally in the presence of an acid binder;

(D) in order to obtain a compound of formula (I-c) in which A, B, D, J, $R^2$, M, X and Y are as defined in claim 1 and L represents sulphur, a compound of the formula (I-a) in which A, B, D, J, X and Y are as defined in claim 1 is in each case reacted with a chlormonothioformic ester or a chlordithioformic ester of formula (VI)

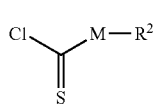
(VI)

in which
M and $R^2$ are as defined in claim 1,
optionally in the presence of a diluent and optionally in the presence of an acid binder
and
(E) in order to obtain a compound of formula (I-d)

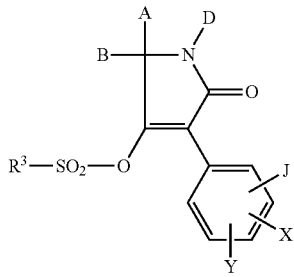
(I-d)

in which A, B, D, J, $R^3$, X and Y are as defined in claim 1, a compound of the formula (I-a) in which A, B, D, J, X and Y are as defined in claim 1 is in each case reacted
with a sulphonyl chloride of formula (VII)

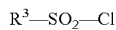
$R^3$—$SO_2$—Cl     (VII)

in which
$R^3$ is as defined in claim 1,
optionally in the presence of a diluent and optionally in the presence of an acid binder,
(F) in order to obtain a compound of formula (I-e)

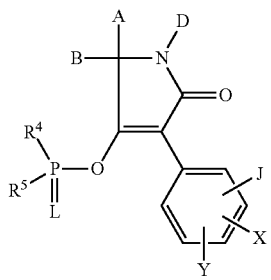
(I-e)

in which A, B, D, J, L, $R^4$, $R^5$, X and Y are as defined in claim 1, a compound of the formula (I-a) in which A, B, D, J, X and Y are as defined in claim 1 is in each case reacted
with a phosphorus compound of formula (VIII)

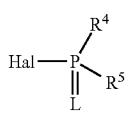
(VIII)

in which
L, $R^4$ and $R^5$ are as defined in claim 1 and
Hal represents halogen,
optionally in the presence of a diluent and optionally in the presence of an acid binder, (G) in order to obtain a compound of formula (I-f)

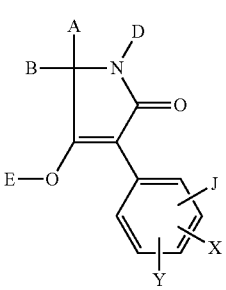
(I-f)

in which A, B, D, E, J, X and Y are as defined in claim 1, a compound of the formula (I-a) in which A, B, D, J, X and Y are as defined in claim 1 is in each case reacted
with a metal compound or an amine of formula (IX) and (X), respectively,

Me(OR$^{10}$)$_t$     (IX)

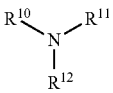
(X)

in which
Me represents a mono- or divalent metal, or represents an ammonium ion

t represents the number 1 or 2 and
$R^{10}$, $R^{11}$, $R^{12}$ independently of one another represent hydrogen or alkyl, optionally in the presence of a diluent,
(H) in order to obtain a compound of formula (I-g)

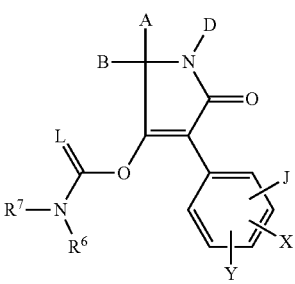
(I-g)

in which A, B, D, J, L, $R^6$, $R^7$, X and Y are as defined in claim 1, a compound of the formula (I-a) in which A, B, D, J, X and Y are as defined in claim 1 is in each case reacted
(α) with an isocyanate or an isothiocyanate of formula (XI)

$R^6$—N═C═L     (XI)

in which
R⁶ and L are as defined in claim 1,
optionally in the presence of a diluent and optionally in the presence of a catalyst or (β) with a carbamoyl chloride or a thiocarbamoyl chloride of formula (XII)

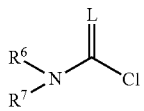

(XII)

in which
L, R⁶ and R⁷ are as defined in claim 1,
optionally in the presence of a diluent and optionally in the presence of an acid binder.

7. A composition for controlling pests, unwanted vegetation, or combinations thereof, comprising at least one compound of the formula (I) according to claim 1.

8. A method for controlling animal pests, unwanted vegetation, or combinations thereof, comprising allowing a compound of the formula (I) according to claim 1 to act on pests, unwanted vegetation, their habitat, or combinations thereof.

9. A process for preparing a composition for controlling pests, unwanted vegetation, or combinations thereof, comprising mixing a compound of the formula (I) according to claim 1 with an extender, a surfactant, or a combination thereof.

10. A composition comprising an effective amount of an active compound combination comprising, as components, (a') at least one trifluoromethoxyphenyl-substituted tetramic acid derivative of the formula (I) in which A, B, D, G, J, X and Y are as defined in claim 1 and (b') at least one crop plant compatibility-improving compound selected from the group consisting of
4-dichloroacetyl-1-oxa-4-azaspiro[4.5]decane (AD-67, MON-4660), 1-dichloroacetylhexahydro-3,3,8a-trimethylpyrrolo[1,2-a]pyrimidin-6(2H)-one (dicyclonon, BAS-145138), 4-dichloroacetyl-3,4-dihydro-3-methyl-2H-1,4-benzoxazine (benoxacor), 1-methylhexyl 5-chloroquinoline-8-oxyacetate (cloquintocet-mexyl), 3-(2-chlorobenzyl)-1-(1-methyl-1-phenylethyl)urea (cumyluron), α-(cyanomethoximino)phenylacetonitrile (cyometrinil), 2,4-dichlorophenoxyacetic acid (2,4-D), 4-(2,4-dichlorophenoxy)butyric acid (2,4-DB), 1-(1-methyl-1-phenylethyl)-3-(4-methylphenyl)urea (daimuron, dymron), 3,6-dichloro-2-methoxybenzoic acid (dicamba), S-1-methyl-1-phenylethyl piperidine-1-thiocarboxylate (dimepiperate), 2,2-dichloro-N-(2-oxo-2-(2-propenylamino)ethyl)-N-(2-propenyl)acetamide (DKA-24), 2,2-dichloro-N,N-di-2-propenylacetamide (dichlormid), 4,6-dichloro-2-phenylpyrimidine (fenclorim), ethyl 1-(2,4-dichlorophenyl)-5-trichloromethyl-1H-1,2,4-triazole-3-carboxylate (fenchlorazole-ethyl), phenylmethyl 2-chloro-4-trifluoromethylthiazole-5-carboxylate (flurazole), 4-chloro-N-(1,3-dioxolan-2-ylmethoxy)-α-trifluoroacetophenone oxime (fluxofenim), 3-dichloroacetyl-5-(2-furanyl)-2,2-dimethyloxazolidine (furilazole, MON-13900), ethyl 4,5-dihydro-5,5-diphenyl-3-isoxazolecarboxylate (isoxadifen-ethyl), 1-(ethoxycarbonyl)ethyl 3,6-dichloro-2-methoxybenzoate (lactidichlor), (4-chloro-o-tolyloxy)acetic acid (MCPA), 2-(4-chloro-o-tolyloxy) propionic acid (mecoprop), diethyl 1-(2,4-dichlorophenyl)-4,5-dihydro-5-methyl-1H-pyrazole-3,5-dicarboxylate (mefenpyr-diethyl), 2-dichloromethyl-2-methyl-1,3-dioxolane (MG-191), 2-propenyl-1-oxa-4-azaspiro[4.5]decane-4-carbodithioate (MG-838), 1,8-naphthalic anhydride, α-(1,3-dioxolan-2-ylmethoximino)phenylacetonitrile (oxabetrinil), 2,2-dichloro-N-(1,3-dioxolan-2-ylmethyl)-N-(2-propenyl) acetamide (PPG-1292), 3-dichloroacetyl-2,2-dimethyloxazolidine (R-28725), 3-dichloroacetyl-2,2,5-trimethyloxazolidine (R-29148), 4-(4-chloro-o-tolyl) butyric acid, 4-(4-chlorophenoxy)butyric acid, diphenylmethoxyacetic acid, methyl diphenylmethoxyacetate, ethyl diphenylmethoxyacetate, methyl 1-(2-chlorophenyl)-5-phenyl-1H-pyrazole-3-carboxylate, ethyl 1-(2,4-dichloro-phenyl)-5-methyl-1H-pyrazole-3-carboxylate, ethyl 1-(2,4-dichlorophenyl)-5-isopropyl-1H-pyrazole-3-carboxylate, ethyl 1-(2,4-dichlorophenyl)-5-(1,1-dimethylethyl)-1H-pyrazole-3-carboxylate, ethyl 1-(2,4-dichlorophenyl)-5-phenyl-1H-pyrazole-3-carboxylate, ethyl 5-(2,4-dichlorobenzyl)-2-isoxazoline-3-carboxylate, ethyl 5-phenyl-2-isoxazoline-3-carboxylate, ethyl 5-(4-fluoro-phenyl)-5-phenyl-2-isoxazoline-3-carboxylate, 1,3-dimethylbut-1-yl 5-chloroquinoline-8-oxyacetate, 4-allyloxybutyl 5-chloroquinoline-8-oxyacetate, 1-allyloxyprop-2-yl 5-chloroquinoline-8-oxyacetate, methyl 5-chloroquinoxaline-8-oxyacetate, ethyl 5-chloroquinoline-8-oxyacetate, allyl 5-chloroquinoxaline-8-oxyacetate, 2-oxoprop-1-yl 5-chloroquinoline-8-oxyacetate, diethyl 5-chloroquinoline-8-oxymalonate, diallyl 5-chloroquinoxaline-8-oxymalonate, diethyl 5-chloroquinoline-8-oxymalonate, 4-carboxychroman-4-ylacetic acid (AC-304415), 4-chlorophenoxyacetic acid, 3,3'-dimethyl-4-methoxybenzophenone, 1-bromo-4-chloromethylsulphonylbenzene, 1-[4-(N-2-methoxybenzoylsulphamoyl)phenyl]-3-methylurea (also known as N-(2-methoxybenzoyl)-4-[(methylaminocarbonyl)amino]benzenesulphonamide), 1-[4-(N-2-methoxybenzoylsulphamoyl)phenyl]-3,3-dimethylurea, 1-[4-(N-4,5-dimethylbenzoylsulphamoyl) phenyl]-3-methylurea, 1-[4-(N-naphthylsulphamoyl) phenyl]-3,3-dimethylurea, N-(2-methoxy-5-methylbenzoyl)-4-(cyclopropylaminocarbonyl) benzenesulphonamide,
a compound of general formula (IIa),

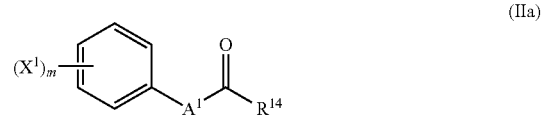

(IIa)

a compound of general formula (IIb),

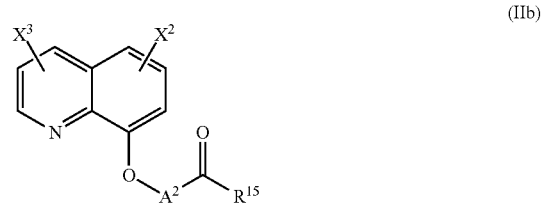

(IIb)

a compound of formula (IIc),

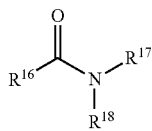
(IIc)

where
m represents a number 0, 1, 2, 3, 4 or 5,
$A^1$ represents one of the divalent heterocyclic groupings shown below

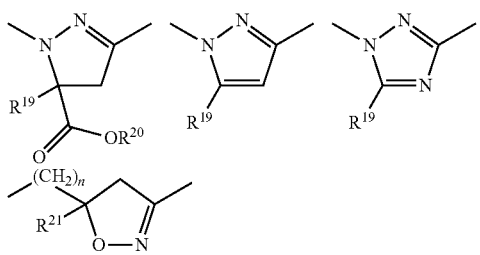

n represents a number 0, 1, 2, 3, 4 or 5,
$A^2$ represents optionally $C_1$-$C_4$-alkyl- and/or $C_1$-$C_4$-alkoxy-carbonyl- and/or $C_1$-$C_4$-alkenyloxycarbonyl-substituted alkanediyl having 1 or 2 carbon atoms,
$R^{14}$ represents hydroxyl, mercapto, amino, $C_1$-$C_6$-alkoxy, $C_1$-$C_6$-alkylthio, $C_1$-$C_6$-alkylamino or di($C_1$-$C_4$-alkyl) amino,
$R^{15}$ represents hydroxyl, mercapto, amino, $C_1$-$C_7$-alkoxy, $C_1$-$C_6$-alkenyloxy, $C_1$-$C_6$-alkenyloxy-$C_1$-$C_6$-alkoxy, $C_1$-$C_6$-alkylthio, $C_1$-$C_6$-alkylamino or di($C_1$-$C_4$-alkyl)-amino,
$R^{16}$ represents optionally fluorine-, chlorine- and/or bromine-substituted $C_1$-$C_4$-alkyl,
$R^{17}$ represents hydrogen, in each case optionally fluorine-, chlorine- and/or bromine-substituted $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or optionally fluorine-, chlorine- and/or bromine- or $C_1$-$C_4$-alkyl-substituted phenyl,
$R^{18}$ represents hydrogen, in each case optionally fluorine-, chlorine- and/or bromine-substituted $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or optionally fluorine-, chlorine- and/or bromine- or $C_1$-$C_4$-alkyl-substituted phenyl, or
$R^{17}$ and $R^{18}$ also together represent $C_3$-$C_6$-alkanediyl or $C_2$-$C_5$-oxaalkanediyl, each of which is optionally substituted by $C_1$-$C_4$-alkyl, phenyl, furyl, a fused benzene ring, or by two substituents which, together with the C atom to which they are attached, form a 5- or 6-membered carbocycle,
$R^{19}$ represents hydrogen, cyano, halogen, or represents in each case optionally fluorine-, chlorine- and/or bromine-substituted $C_1$-$C_4$-alkyl, $C_3$-$C_6$-cycloalkyl or phenyl,
$R^{20}$ represents hydrogen, in each case optionally hydroxyl-, cyano-, halogen- or $C_1$-$C_4$-alkoxy-substituted $C_1$-$C_6$-alkyl, $C_3$-$C_6$-cycloalkyl or tri-($C_1$-$C_4$-alkyl)silyl,
$R^{21}$ represents hydrogen, cyano, halogen, or represents in each case optionally fluorine-, chlorine- and/or bromine-substituted $C_1$-$C_4$-alkyl, $C_3$-$C_6$-cycloalkyl or phenyl,
$X^1$ represents nitro, cyano, halogen, $C_1$-$C_4$-alkyl, $C_1$-$C_4$-haloalkyl, $C_1$-$C_4$-alkoxy or $C_1$-$C_4$-haloalkoxy,
$X^2$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy,
$X^3$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy,
a compound of general formula (IId)

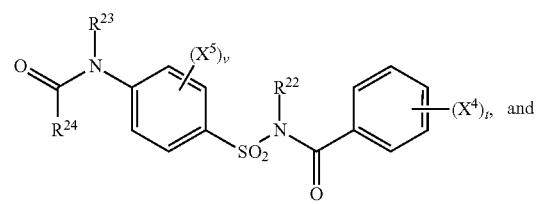

a compound of general formula (IIe)

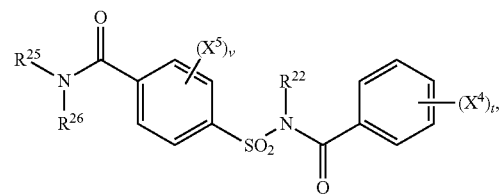

where
t represents a number 0, 1, 2, 3, 4 or 5,
v represents a number 0, 1, 2, 3, 4 or 5,
$R^{22}$ represents hydrogen or $C_1$-$C_4$-alkyl,
$R^{23}$ represents hydrogen or $C_1$-$C_4$-alkyl,
$R^{24}$ represents hydrogen, in each case optionally cyano-, halogen- or $C_1$-$C_4$-alkoxy-substituted $C_1$-$C_6$-alkyl, $C_1$-$C_6$-alkoxy, $C_1$-$C_6$-alkylthio, $C_1$-$C_6$-alkylamino or di($C_1$-$C_4$-alkyl)amino, or in each case optionally cyano-, halogen- or $C_1$-$C_4$-alkyl-substituted $C_3$-$C_6$-cycloalkyl, $C_3$-$C_6$-cycloalkyloxy, $C_3$-$C_6$-cycloalkylthio or $C_3$-$C_6$-cycloalkylamino,
$R^{25}$ represents hydrogen, optionally cyano-, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, or optionally cyano-, halogen- or $C_1$-$C_4$-alkyl-substituted $C_3$-$C_6$-cycloalkyl,
$R^{26}$ represents hydrogen, optionally cyano-, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, optionally cyano-, halogen- or $C_1$-$C_4$-alkyl-substituted $C_3$-$C_6$-cycloalkyl, or optionally nitro-, cyano-, halogen-, $C_1$-$C_4$-alkyl-, $C_1$-$C_4$-haloalkyl-, $C_1$-$C_4$-alkoxy- or $C_1$-$C_4$-haloalkoxy-substituted phenyl, or together with $R^{25}$ represents in each case optionally $C_1$-$C_4$-alkyl-substituted $C_2$-$C_6$-alkanediyl or $C_2$-$C_5$-oxaalkanediyl, $X^4$ represents nitro, cyano, carboxyl, carbamoyl, formyl, sulphamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy, and $X^5$ represents nitro, cyano, carboxyl, carbamoyl, formyl, sulphamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy.

11. A composition according to claim 10 in which the crop plant compatibility-improving compound is selected from the group consisting of cloquintocet-mexyl, fenchlorazole-ethyl, isoxadifen-ethyl, mefenpyr-diethyl, furilazole, fenclorim, cumyluron, dymron,

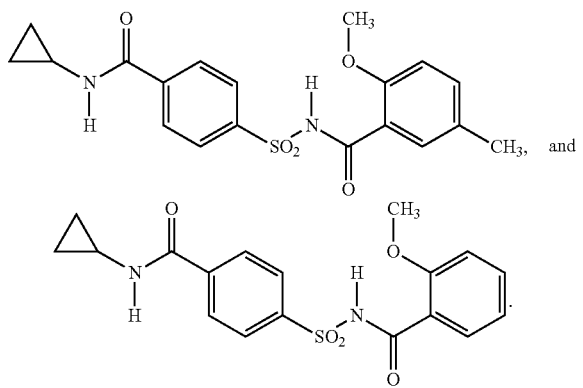

12. A composition according to claim 10, in which the crop plant compatibility-improving compound is cloquintocet-mexyl.

13. A composition according to claim 10, in which the crop plant compatibility-improving compound is mefenpyr-diethyl.

14. A method of controlling unwanted vegetation, comprising allowing a composition according to claim 10 to act on the plants, their surroundings, or combinations thereof.

15. A method of controlling unwanted vegetation, comprising allowing a compound of the formula (I) according to claim 1 and the crop plant compatibility-improving compound selected from the group consisting of 4-dichloroacetyl-1-oxa-4-azaspiro[4.5]decane (AD-67, MON-4660), 1-dichloroacetylhexahydro-3,3,8a-trimethylpyrrolo[1,2-a]pyrimidin-6(2H)-one (dicyclonon BAS-145138), 4-dichloroacetyl-3,4-dihydro-3-methyl-2H-1,4-benzoxazine (benoxacor), 1-methylhexyl 5-chloroquinoline-8-oxyacetate (cloquintocet-mexyl), 3-(2-chlorobenzyl)-1-(1-methyl-1-phenylethyl)urea (cumyluron), α-(cyanomethoximino)phenylacetonitrile (cyometrinil), 2,4-dichlorophenoxyacetic acid (2,4-D), 4-(2,4-dichlorophenoxy)butyric acid (2,4-DB), 1-(1-methyl-1-phenylethyl)-3-(4-methylphenyl)urea (daimuron, dymron), 3,6-dichloro-2-methoxybenzoic acid (dicamba), S-1-methyl-1-phenylethyl piperidine-1-thiocarboxylate (dimepiperate), 2,2-dichloro-N-(2-oxo-2-(2-propenylamino)ethyl)-N-(2-propenyl)acetamide (DKA-24), 2,2-dichloro-N,N-di-2-propenylacetamide (dichlormid), 4,6-dichloro-2-phenylpyrimidine (fenclorim), ethyl 1-(2,4-dichlorophenyl)-5-trichloromethyl-1H-1,2,4-triazole-3-carboxylate (fenchlorazole-ethyl), phenylmethyl 2-chloro-4-trifluoromethylthiazole-5-carboxylate (flurazole), 4-chloro-N-(1,3-dioxolan-2-ylmethoxy)-α-trifluoroacetophenone oxime (fluxofenim), 3-dichloroacetyl-5-(2-furanyl)-2,2-dimethyloxazolidine (furilazole, MON-13900), ethyl 4,5-dihydro-5,5-diphenyl-3-isoxazolecarboxylate (isoxadifen-ethyl), 1-(ethoxycarbonyl)ethyl 3,6-dichloro-2-methoxybenzoate (lactidichlor), (4-chloro-o-tolyloxy)acetic acid (MCPA), 2-(4-chloro-o-tolyloxy)propionic acid (mecoprop), diethyl 1-(2,4-dichlorophenyl)-4,5-dihydro-5-methyl-1H-pyrazole-3,5-dicarboxylate (mefenpyr-diethyl), 2-dichloromethyl-2-methyl-1,3-dioxolane (MG-191), 2-propenyl-1-oxa-4-azaspiro[4.5]decane-4-carbodithioate (MG-838), 1,8-naphthalic anhydride, α-(1,3-dioxolan-2-ylmethoximino)phenylacetonitrile (oxabetrinil), 2,2-dichloro-N-(1,3-dioxolan-2-ylmethyl)-N-(2-propenyl)acetamide (PPG-1292), 3-dichloroacetyl-2,2-dimethyloxazolidine (R-28725), 3-dichloroacetyl-2,2,5-trimethyloxazolidine (R-29148), 4-(4-chloro-o-tolyl)butyric acid, 4-(4-chlorophenoxy)butyric acid, diphenylmethoxyacetic acid, methyl diphenylmethoxyacetate, ethyl diphenylmethoxyacetate, methyl 1-(2-chlorophenyl)-5-phenyl-1H-pyrazole-3-carboxylate, ethyl 1-(2,4-dichlorophenyl)-5-methyl-1H-pyrazole-3-carboxylate, ethyl 1-(2,4-dichlorophenyl)-5-isopropyl-1H-pyrazole-3-carboxylate, ethyl 1-(2,4-dichlorophenyl)-5-(1,1-dimethylethyl)-1H-pyrazole-3-carboxylate, ethyl 1-(2,4-dichlorophenyl)-5-phenyl-1H-pyrazole-3-carboxylate, ethyl 5-(2,4-dichlorobenzyl)-2-isoxazoline-3-carboxylate, ethyl 5-phenyl-2-isoxazoline-3-carboxylate, ethyl 5-(4-fluorophenyl)-5-phenyl-2-isoxazoline-3-carboxylate, 1,3-dimethylbut-1-yl 5-chloroquinoline-8-oxyacetate, 4-allyloxybutyl 5-chloroquinoline-8-oxyacetate, 1-allyloxyprop-2-yl 5-chloroquinoline-8-oxyacetate, methyl 5-chloroquinoxaline-8-oxyacetate, ethyl 5-chloroquinoline-8-oxyacetate, allyl 5-chloroquinoxaline-8-oxyacetate, 2-oxoprop-1-yl 5-chloroquinoline-8-oxyacetate, diethyl 5-chloroquinoline-8-oxymalonate, diallyl 5-chloroquinoxaline-8-oxymalonate, diethyl 5-chloroquinoline-8-oxymalonate, 4-carboxychroman-4-ylacetic acid (AC-304415), 4-chlorophenoxyacetic acid, 3,3'-dimethyl-4-methoxybenzophenone, 1-bromo-4-chloromethylsulphonylbenzene, 1-[4-(N-2-methoxybenzoylsulphamoyl)phenyl]-3-methylurea (also known as N-(2-methoxybenzoyl)-4-[(methylaminocarbonyl)amino]benzenesulphonamide), 1-[4-(N-2-methoxybenzoylsulphamoyl)phenyl]-3,3-dimethylurea, 1-[4-(N-4,5-dimethylbenzoylsulphamoyl)phenyl]-3-methylurea, 1-[4-(N-naphthylsulphamoyl)phenyl]-3,3-dimethylurea, N-(2-methoxy-5-methylbenzoyl)-4-(cyclopropylaminocarbonyl)benzenesulphonamide, a compound of general formula (IIa),

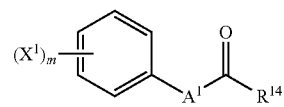

(IIa)

a compound of general formula (IIb),

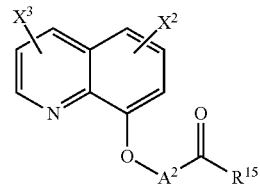

(IIb)

a compound of formula (IIc),

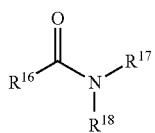

where m represents a number 0, 1, 2, 3, 4 or 5, $A^1$ represents one of the divalent heterocyclic groupings shown below

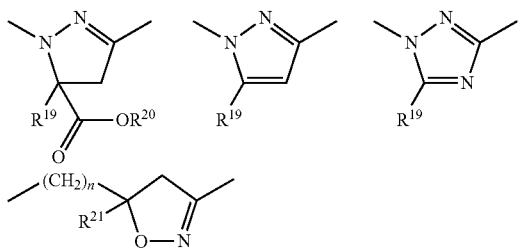

n represents a number 0, 1, 2, 3, 4 or 5, $A^2$ represents optionally $C_1$-$C_4$-alkyl- and/or $C_1$-$C_4$-alkoxy-carbonyl- and/or $C_1$-$C_4$-alkenyloxycarbonyl-substituted alkanediyl having 1 or 2 carbon atoms, $R^{14}$ represents hydroxyl, mercapto, amino, $C_1$-$C_6$-alkoxy, $C_1$-$C_6$-alkylthio, $C_1$-$C_6$-alkylamino or di($C_1$-$C_4$-alkyl)amino, $R^{15}$ represents hydroxyl, mercapto, amino, $C_1$-$C_7$-alkoxy, $C_1$-$C_6$-alkenyloxy, $C_1$-$C_6$-alkenyloxy-$C_1$-$C_6$-alkoxy, $C_1$-$C_6$-alkylthio, $C_1$-$C_6$-alkylamino or di($C_1$-$C_4$-alkyl)-amino, $R^{16}$ represents optionally fluorine-, chlorine- and/or bromine-substituted $R^{17}$ represents hydrogen, in each case optionally fluorine-, chlorine- and/or bromine-substituted $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or optionally fluorine-, chlorine- and/or bromine- or $C_1$-$C_4$-alkyl-substituted phenyl, $R^{18}$ represents hydrogen, in each case optionally fluorine-, chlorine- and/or bromine-substituted $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or optionally fluorine-, chlorine- and/or bromine- or $C_1$-$C_4$-alkyl-substituted phenyl, or $R^{17}$ and $R^{18}$ also together represent $C_3$-$C_6$-alkanediyl or $C_2$-$C_5$-oxaalkanediyl, each of which is optionally substituted by $C_1$-$C_4$-alkyl, phenyl, furyl, a fused benzene ring or by two substituents which, together with the C atom to which they are attached, form a 5- or 6-membered carbocycle, $R^{19}$ represents hydrogen, cyano, halogen, or represents in each case optionally fluorine-, chlorine- and/or bromine-substituted $C_1$-$C_4$-alkyl, $C_3$-$C_6$-cycloalkyl or phenyl, $R^{20}$ represents hydrogen, in each case optionally hydroxyl-, cyano-, halogen- or $C_1$-$C_4$-alkoxy-substituted $C_1$-$C_6$-alkyl, $C_3$-$C_6$-cycloalkyl or tri-($C_1$-$C_4$-alkyl)silyl, $R^{21}$ represents hydrogen, cyano, halogen, or represents in each case optionally fluorine-, chlorine- and/or bromine-substituted $C_1$-$C_4$-alkyl, $C_3$-$C_6$-cycloalkyl or phenyl, $X^1$ represents nitro, cyano, halogen, $C_1$-$C_4$-alkyl, $C_1$-$C_4$-haloalkyl, $C_1$-$C_4$-alkoxy or $C_1$-$C_4$-haloalkoxy, $X^2$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, $X^3$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, a compound of general formula (IId)

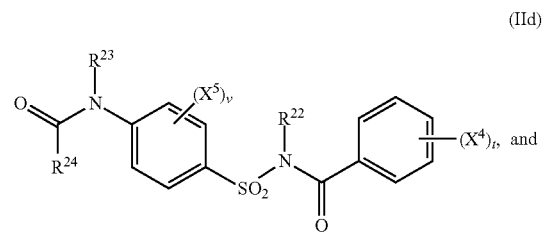

a compound of general formula (IIe)

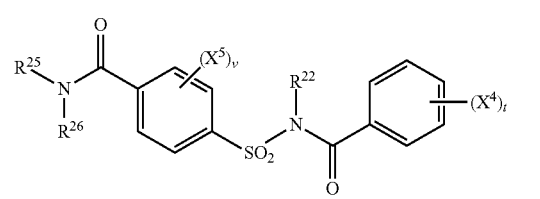

where t represents a number 0, 1, 2, 3, 4 or 5, v represents a number 0, 1, 2, 3, 4 or 5, $R^{22}$ represents hydrogen or $C_1$-$C_4$-alkyl, $R^{23}$ represents hydrogen or $C_1$-$C_4$-alkyl, $R^{24}$ represents hydrogen, in each case optionally cyano-, halogen- or $C_1$-$C_4$-alkoxy-substituted $C_1$-$C_6$-alkyl, $C_1$-$C_6$-alkoxy, $C_1$-$C_6$-alkylthio, $C_1$-$C_6$-alkylamino or di($C_1$-$C_4$-alkyl)amino, or in each case optionally cyano-, halogen- or $C_1$-$C_4$-alkyl-substituted $C_3$-$C_6$-cycloalkyl, $C_3$-$C_6$-cycloalkyloxy, $C_3$-$C_6$-cycloalkylthio or $C_3$-$C_6$-cycloalkylamino, $R^{25}$ represents hydrogen, optionally cyano-, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, or optionally cyano-, halogen- or $C_1$-$C_4$-alkyl-substituted $C_3$-$C_6$-cycloalkyl, $R^{26}$ represents hydrogen, optionally cyano-, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, optionally cyano-, halogen- or $C_1$-$C_4$-alkyl-substituted $C_3$-$C_6$-cycloalkyl, or optionally nitro-, cyano-, halogen-, $C_1$-$C_4$-alkyl-, $C_1$-$C_4$-haloalkyl-, $C_1$-$C_4$-alkoxy- or $C_1$-$C_4$-haloalkoxy-substituted phenyl, or together with $R^{25}$ represents in each case optionally $C_1$-$C_4$-alkyl-substituted $C_2$-$C_6$-alkanediyl or $C_2$-$C_5$-oxaalkanediyl, $X^4$ represents nitro, cyano, carboxyl, carbamoyl, formyl, sulphamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy, and $X^5$ represents nitro, cyano, carboxyl, carbamoyl, formyl, sulphamoyl, hydroxyl, amino, halogen, $C_1$-$C_4$-alkyl, $C_1$-$C_4$-haloalkyl, $C_1$-$C_4$-alkoxy of $C_1$-$C_4$-haloalkoxy to act, separately in close temporal succession, on the plants or their surroundings.

16. A composition, comprising
at least one compound of the formula (I) according to claim 1 and
at least one salt of the formula (III')

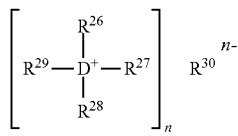

(III')

in which

D represents nitrogen or phosphorus, $R^{26}$, $R^{27}$, $R^{28}$ and $R^{29}$ independently of one another represent hydrogen or in each case optionally substituted $C_1$-$C_8$-alkyl or mono- or polyunsaturated, optionally substituted $C_1$-$C_8$-alkylene, wherein the substituents are selected from the group consisting of halogen, nitro and cyano, n represents 1, 2, 3 or 4, $R^{30}$ represents an organic or inorganic anion.

17. A composition according to claim 16, further comprising at least one penetrant.

18. A method of increasing the action of a pesticide, a herbicide, or a combination thereof, comprising preparing a ready-to-use (spray liquor) composition comprising an active compound of the formula (I) according to claim 1 and a salt of the formula (III')

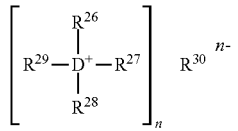

(III')

in which

D represents nitrogen or phosphorus, $R^{26}$, $R^{27}$, $R^{28}$ and $R^{29}$ independently of one another represent hydrogen or in each case optionally substituted $C_1$-$C_8$-alkyl or mono- or polyunsaturated, optionally substituted $C_1$-$C_8$-alkylene, wherein the substituents are selected from the group consisting of halogen, nitro and cyano, n represents 1, 2, 3 or 4, $R^{30}$ represents an organic or inorganic anion.

19. A method according to claim 18, wherein the spray liquor further comprises a penetrant.

20. A composition, comprising
a composition according to claim 10 and
at least one salt of the formula (III')

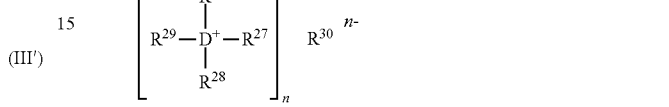

(III')

in which

D represents nitrogen or phosphorus, $R^{26}$, $R^{27}$, $R^{28}$ and $R^{29}$ independently of one another represent hydrogen or in each case optionally substituted $C_1$-$C_8$-alkyl or mono- or polyunsaturated, optionally substituted $C_1$-$C_8$-alkylene, wherein the substituents are selected from the group consisting of halogen, nitro and cyano, n represents 1, 2, 3 or 4, $R^{30}$ represents an organic or inorganic anion.

21. A method of increasing the action of a pesticide, a herbicide, or a combination thereof, comprising preparing a ready-to-use (spray liquor) composition comprising a composition according to claim 10, and a salt of the formula (III')

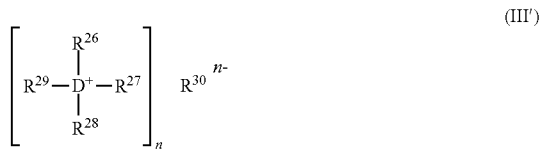

(III')

in which

D represents nitrogen or phosphorus, $R^{26}$, $R^{27}$, $R^{28}$ and $R^{29}$ independently of one another represent hydrogen or in each case optionally substituted $C_1$-$C_8$-alkyl or mono- or polyunsaturated, optionally substituted $C_1$-$C_8$-alkylene, wherein the substituents are selected from the group consisting of halogen, nitro and cyano, n represents 1, 2, 3 or 4, $R^{30}$ represents an organic or inorganic anion.

* * * * *